(12) United States Patent
Haab et al.

(10) Patent No.: US 7,838,634 B2
(45) Date of Patent: Nov. 23, 2010

(54) METHODS FOR MEASURING GLYCAN LEVELS OF PROTEINS

(75) Inventors: Brian B. Haab, Jenison, MI (US); Songming Chen, Grand Rapids, MI (US)

(73) Assignee: Van Andel Research Institute, Grand Rapids, MI (US)

( * ) Notice: Subject to any disclaimer, the term of this patent is extended or adjusted under 35 U.S.C. 154(b) by 0 days.

(21) Appl. No.: 11/375,756

(22) Filed: Mar. 15, 2006

(65) Prior Publication Data

US 2007/0178538 A1 Aug. 2, 2007

Related U.S. Application Data

(60) Provisional application No. 60/671,829, filed on Apr. 15, 2005.

(51) Int. Cl.
*C07K 16/00* (2006.01)
*G01N 33/53* (2006.01)

(52) U.S. Cl. ..................... 530/387.1; 435/7.1
(58) Field of Classification Search ............... 530/387.1
See application file for complete search history.

(56) References Cited

U.S. PATENT DOCUMENTS

| | | | | |
|---|---|---|---|---|
| 4,389,392 | A * | 6/1983 | Adachi ......................... | 436/501 |
| 5,329,028 | A * | 7/1994 | Ashkenazi et al. .......... | 548/548 |
| 2002/0137104 | A1* | 9/2002 | Cosma ....................... | 435/7.9 |
| 2002/0164824 | A1* | 11/2002 | Xiao et al. ................... | 436/524 |
| 2003/0153014 | A1* | 8/2003 | Shen et al. .................... | 435/7.9 |
| 2004/0023306 | A1 | 2/2004 | Aebersold et al. | |
| 2004/0063624 | A1* | 4/2004 | Kage et al. ..................... | 514/8 |

FOREIGN PATENT DOCUMENTS

| | | |
|---|---|---|
| WO | 0237106 A2 | 5/2002 |
| WO | 03060522 A1 | 7/2003 |
| WO | WO 03087821 * | 10/2003 |

OTHER PUBLICATIONS

Keusch et al., Clin. Chim. Acta, 1996, 252: 147-158.*
Routh et al., J. Neuroscience Methods, 1997, 71:163-168.*
Jung et al., Analyst, 2008, 133:697-701.*
Taussig et al., Targets, 2003, 2(4): 169-176.*

Parker, N. et al. A new enzyme-linked lectin/mucin antibody sandwich assay (CAM 17.1/WGA) assessed in combination with CA 19-9 and peanut lectin binding assay for the diagnosis of pancreatic cancer. *Cancer* 70, 1062-8 (1992).
Blixt, O. et al, Printed covalent glycan array for ligand profiling of diverse glycan binding proteins. *Proc Natl Acad Sci U S A* 101, 17033-17038 (2004).
Haab, B.B., et al. Protein microarrays for highly parallel detection and quantification of specific proteins and antibodies in complex solutions. *Genome Biol* 264, 33-45 (2004).
Kuno, A. et al. Evanescent-field fluorescence-assisted lectin microarray: a new strategy for glycan profiling. *Nat Methods* 2, 851-6 (2005).
Brian B. Haab, et al., "839.4 Antibody microarray analysis of blood serum from cancer patients," Experimental Biology 2003: Meeting Abstracts, FASEB Journal, p. 1, (Apr. 4, 2003).
Heping Zhou, et al., "Two-color, rolling-circle amplification on antibody microarrays for sensitive, multiplexed serum-protein measurements," Genome Biology, Article R28, Open Access, vol. 5 ( No. 4), pp. 1-12, (Mar. 30, 2004).
Sudeepa Bhattacharyya, et al., "Diagnosis of Pancreatic Cancer Using Serum Proteomic Profiling," Neoplasia, vol. 6 (No. 5), p. 674-686, (2004).
Birte Schulenberg, et al., "Mapping glycosylation changes related to cancer using the Multiplexed Proteomics technology: a protein differential display approach," Journal of Chromatography B 793, Elsevier p. 127-139, (2003).
Darren Hamelinck, et al., "Optimized Normalization for Antibody Microarrays and Application to Serum-Proten Profiling," Molecular & Cellular Proteomics 4.6, The American Society for Biochemistry and Molecular Biology, p. 773-784, (Mar. 25, 2005).
Jeremy C. Miller, et al., "Antibody microarray profiling of human prostate cancer sera: Antibody screening and identification of potential biomarkers," Proteomics, Wiley-VCH Verlag GmbH & Co. KGaA, Weinheim, p. 56-63, (2003).
Chen S et al., Antibody-lectin microarrays reveal altered glycosylation on secreted proteins in pancreatic cancer patients. Proceeding of the Annual Association for Cancer Research 47:337-338 (Apr. 2006).
Haab B et al., RCA-Enhanced Protein Detection Arrays. Methods in Molecular Biology 328: 15-29 (2006).
Rosenfeld R et al., U-c Fingerprint: Glycoprotein Analysis Based on A Lectin Array. Glycobiology 13 (No. 11): 845 (Nov. 2003).
PCT/US2006013557, European Search Report, May 9, 2008.

* cited by examiner

*Primary Examiner*—Larry R Helms
*Assistant Examiner*—Hong Sang
(74) *Attorney, Agent, or Firm*—Price, Heneveld, Cooper, DeWitt & Litton, LLP

(57) ABSTRACT

The invention includes a high-through-put method of screening for a biomarker indicative of a disease, including the identification of a glycan alteration in a protein of a diseased patient. Further, the invention includes methods utilizing a microarray to measure the glycan level of a protein.

9 Claims, 19 Drawing Sheets

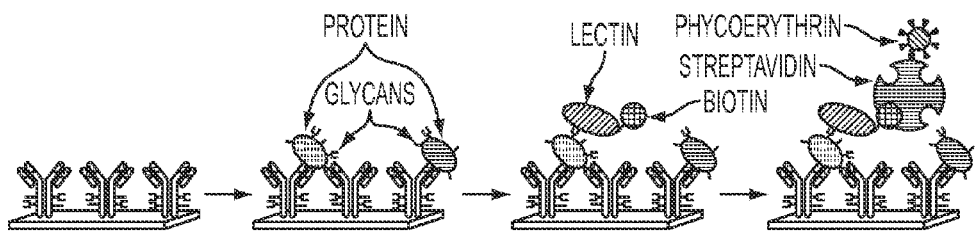
FIG. 11A
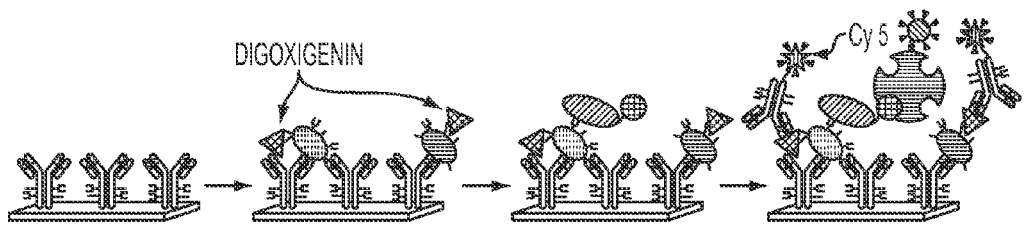
FIG. 11B
|  | NO SCRUM | | UNLABELED SCRUM | | LABELED SCRUM | |
|---|---|---|---|---|---|---|
|  | 543nm | 633nm | 543nm | 633nm | 543nm | 633nm |
| Anti-IgM | | | | | | |
| Anti-Alpha-I-antitrypsin | | | | | | |
| Anti-PIVKA II | | | | | | |
| Anti-MUC1 | | | | | | |
| Anti-Alpha 2 Macroglobulin | | | | | | |
| Anti-von Willebrand factor | | | | | | |
FIG. 11C

METHODS FOR MEASURING GLYCAN LEVELS OF PROTEINS

CROSS-REFERENCE TO RELATED APPLICATION

This application claims the benefit of provisional application Ser. No. 60/671,829 filed Apr. 15, 2005, entitled DCP BIOMARKER FOR PANCREATIC CANCER, the entire contents of which are incorporated herein in their entirety.

FIELD OF THE INVENTION

This invention relates to the field of molecular biology and medicine and specifically to assays for measuring levels of protein modifications.

BACKGROUND OF THE INVENTION

Methods to detect cancers more accurately or at earlier stages could lead to better outcomes for many cancer patients, including patents with pancreatic cancer. The success of this goal is facilitated by technologies that allow the rapid profiling and characterization of candidate biomarkers. Many technologies for that purpose are in development, each with unique optimal applications and advantages and disadvantages. Affinity-based methods, using antibodies or other affinity reagents, are preferred in applications where reproducible, specific and relatively high-throughput protein detection is required. The value of affinity-based methods has been enhanced through the use of microarrays, which allow multiplexed and high-throughput protein analysis in low sample volumes.

Pancreatic cancer is typically diagnosed at a late stage. The late stage detection combined with few treatment options lead to five year survival rates of less than 5%. Yeo, C. J., Cameron, J. L., Lillemoe, K. D., Sitzmann, J. V., Hruban, R. H., Goodman, S. N., Dooley, W. C., Coleman, J., and Pitt, H. A. Pancreaticoduodenectomy for cancer of the head of the pancreas. 201 patients. Ann Surg, 221: 721-731; discussion 731-723, 1995.

Blood-based diagnostic tests for pancreatic would be especially valuable because of the potential for routine and inexpensive screening. Several serum markers previously have been investigated for pancreatic cancer diagnostics. The CA 19-9 antigen—a carbohydrate blood group antigen—is elevated in 50-75% of pancreatic cancer cases and is typically used to confirm diagnosis or to monitor a patient's progress after surgery. Riker, A., Libutti, S. K., and Bartlett, D. L. Advances in the early detection, diagnosis, and staging of pancreatic cancer. Surgical Oncology, 6: 157-169, 1998. CA 19-9 is not used for early screening since it is not present in patients with certain blood types and is often elevated in benign disease.

Other carbohydrate antigens are associated with pancreatic cancer, such as SPAN-1 (Frena, A. SPan-1 and exocrine pancreatic carcinoma. The clinical role of a new tumor marker. Int J Biol Markers, 16: 189-197, 2001); DUPAN-2 (Kawa, S., Oguchi, H., Kobayashi, T., Tokoo, M., Furuta, S., Kanai, M., and Homma, T. Elevated serum levels of Dupan-2 in pancreatic cancer patients negative for Lewis blood group phenotype. Br J Cancer, 64: 899-902, 1991); CEA; CA-50; 90K (Gentiloni, N., Caradonna, P., Costamagna, B., E'Ostilio, N., Perri, V., Mutignani, M., Febbraro, S., Tinari, N., Iacobelli, S., and Natoli, C. Pancreatic juice 90K and serum CA 19-9 combined determination can discriminate between pancreatic cancer and chronic pancreatitis. Amer. J. Gastroenterology, 90: 1069-1072, 1995); CA 195 (Hyoty, M., Hyoty, H., Aaran, R. K., Airo, I., and Nordback, I. Tumour antigens CA 195 and CA 19-9 in pancreatic juice and serum for the diagnosis of pancreatic carcinoma. Eur J Surg, 158: 173-179, 1992); TUM2-PK (Oremek, G. M., Eigenbrodt, E., Radle, J., Zeuzem, S., and Seiffert, U. B. Value of the serum levels of the tumor marker TUM2-PK in pancreatic cancer. Anticancer Res, 17: 3031-3033, 1997); and CA 242 (Pasanen, P. A., Eskelinen, M., Partanen, K., Pikkarainen, P., Penttila, I., and Alhava, E. Multivariate analysis of six serum tumor markers (CEA, CA 50, CA 242, TPA, TPS, TATI) and conventional laboratory tests in the diagnosis of hepatopancreatobiliary malignancy. Anticancer Res, 15: 2731-2737, 1995).

Certain changes that occur in the sera of pancreatic cancer patients reflect the high level of inflammation associated with the disease. Pro-inflammatory cytokines, such as IL-6 and IL-8 (Wigmore, S. J., Fearon, K. C., Sangster, K., Maingay, J. P., Garden, O. J., and Ross, J. A. Cytokine regulation of constitutive production of interleukin-8 and -6 by human pancreatic cancer cell lines and serum cytokine concentrations in patients with pancreatic cancer. Int J Oncol, 21: 881-886, 2002), and the acute phase reactant C-reactive protein (CRP) are usually elevated in the sera of pancreatic cancer patients. Fearon, K. C., Barber, M. D., Falconer, J. S., McMillan, D. C., Ross, J. A., and Preston, T. Pancreatic cancer as a model: inflammatory mediators, acute-phase response, and cancer cachexia. World J Surg, 23: 584-588, 1999. Numerous other proteins have been evaluated as serum biomarkers for pancreatic cancer. The performance of tests based on single markers so far has not been good enough to be recommended for clinical application.

Prior studies were performed measuring one protein at a time, using sample and reagent volumes that in most cases prohibited large-scale studies of multiple candidate markers. The measurement of many putative cancer-associated serum proteins together, as enabled by antibody microarrays, has valuable uses. Multiple candidate markers are efficiently screened, allowing a broad characterization of the types of alterations present in cancer sera, and multiple measurements can be used in combination to potentially improve the diagnostic accuracy. Multiple, independent markers may be grouped together to improve diagnostic performance if the markers contribute complementary, non-overlapping discrimination information. The challenge for pancreatic cancer diagnostics is to find the particular protein alterations or combinations of protein alterations that usually occur early in cancer development and that do not occur in benign conditions.

The application of antibody and protein microarray methods to cancer research has been demonstrated in studies on proteins in sera, cell culture, and resected tissue samples. Miller, J. C., Zhou, H., Kwekel, J., Cavallo, R., Burke, J., Butler, E. B., Teh, B. S., and Haab, B. B. Antibody microarray profiling of human prostate cancer sera: antibody screening and identification of potential biomarkers. Proteomics, 3: 56-63, 2003; Huang, R.-P., Huang, R., Fan, Y., and Lin, Y. Simultaneous detection of multiple cytokines from conditioned media and patient's sera by an antibody-based protein array system. Anal. Biochem., 294: 55-62, 2001; Huang, R., Lin, Y., Shi, Q., Flowers, L., Ramachandran, S., Horowitz, I. R., Parthasarathy, S., and Huang, R. P. Enhanced protein profiling arrays with ELISA-based amplification for high-throughput molecular changes of tumor patients' plasma. Clin Cancer Res, 10: 598-609, 2004; Zhou, H., Bouwman, K., Schotanus, M., Verweij, C., Marrero, J. A., Dillon, D., Costa, J., Lizardi, P. M., and Haab, B. B. Two-color, rolling-circle amplification on antibody microarrays for sensitive, multiplexed serum-protein measurements. Genome Biology, 5: R28, 2004; Hamelinck, D., Zhou, H., Li, L., Verweij, C., Dillon, D., Feng, Z., Costa, J., and Haab, B. B. Optimized normalization for antibody microarrays and application to serum-protein profiling. Mol Cell Proteomics, 2005; Sreekumar, A., Nyati, M. K., Varambally, S., Barrette, T. R., Ghosh, D., Lawrence, T. S., and Chinnaiyan, A. M. Profiling of cancer cells using protein microarrays: discovery of novel radiation-regulated proteins. Cancer Research, 61: 7585-7593, 2001; Lin, Y., Huang, R., Cao, X., Wang, S. M., Shi, Q., and Huang, R. P. Detection of multiple cytokines by protein arrays from cell lysate and tissue lysate. Clin Chem Lab Med, 41: 139-145, 2003; Knezevic, V., Leethanakul, C., Bichsel, V. E., Worth, J. M., Prabhu, V. V., Gutkind, J. S., Liotta, L. A., Munson, P. J., Petricoin, E. F. I., and Krizman, D. B. Proteomic profiling of the cancer microenvironment by antibody arrays. Proteomics, 1: 1271-1278, 2001; Tannapfel, A., Anhalt, K., Hausermann, P., Sommerer, F., Benicke, M., Uhlmann, D., Witzigmann, H., Hauss, J., and Wittekind, C. Identification of novel proteins associated with hepatocellular carcinomas using protein microarrays. J Pathol, 201: 238-249, 2003; Hudelist, G., Pacher-Zavisin, M., Singer, C. F., Holper, T., Kubista, E., Schreiber, M., Manavi, M., Bilban, M., and Czerwenka, K. Use of high-throughput protein array for profiling of differentially expressed proteins in normal and malignant breast tissue. Breast Cancer Res Treat, 86: 281-291, 2004.

Alterations to Post-translationally-modified Proteins

Many proteins are modified through glycosylation, or the attachment of carbohydrate chains at specific locations. The structures of these chains are precisely regulated and often play a major role in protein fimction. Glycosylation is an important determinant of protein function, and changes in glycosylation are thought to play roles in certain disease processes, including cancer. Thus, the ability to efficiently profile and measure variations in glycosylation on multiple proteins and in multiple samples is valuable to identify disease-associated glycans alterations and new diagnostic markers. Specifically, the ability to efficiently profile the variation in glycosylation could lead to the identification of disease-associated glycan alterations and new diagnostic biomarkers.

The current methods for analyzing glycans are either cumbersome or very low throughput and not reproducible enough for diagnostics research. Traditionally, glycan structure is studied by enzymatic or chemical cleavage of carbohydrate groups, followed by gel or chromatography analysis and perhaps mass spectrometry analysis. While these methods are useful for determining glycan structures, they are not suitable for studies requiring reproducible measurements over many different samples or proteins, or for determining variation between populations of samples.

Affinity chromatography methods have been used to measure abundances of glycans. Useful affinity reagents for carbohydrate research are lectins—plant and animal proteins with natural carbohydrate binding functionality. Lectins have been used in a variety of formats such as affinity chromatography to isolate glycoproteins and modified ELISAs. Lectins and antibodies against carbohydrate epitopes have been used to identify cancer-associated glycosylation, although those methods do not identify which proteins are carrying the epitopes. Affinity chromatography methods could be coupled to immunoprecipitation methods to measure glycans on specific proteins.

As discussed below, the inventor has developed a high throughput affinity-based method that is practical for multiplexed studies. The inventor has applied the method of the present invention to the study of changes in glycan levels on serum proteins in pancreatic cancer patients.

SUMMARY OF THE INVENTION

The present invention includes a high-throughput method of screening for a biomarker indicative of a disease including: providing serum samples from diseased patients who are afflicted with the disease, providing serum samples from healthy patients who are not afflicted with the disease, determining whether a glycan alteration in a protein in the diseased patient serum samples is present at a higher level than in the protein in the healthy patient serum samples, and if the diseased patient serum samples have said higher level, identifying the glycan alteration in the protein as a biomarker indicative of a disease.

The present invention further includes a method of measuring the glycan level of a protein including: providing a biological sample from a patient; providing a group of antibodies that bind specifically to capture proteins in the sample; spotting the group of antibodies at particular addresses on a microarray; labeling the serum proteins in the sample with a first tag; incubating the sample on the microarray such that the serum proteins in the sample are bound to the antibodies on the microarray; washing off unbound serum proteins from the microarray; providing a glycan binding protein labeled with a second tag; incubating the labeled glycan binding protein on the microarray such that the labeled glycan binding protein binds to a glycan on the serum proteins that are bound to the antibodies on the microarray; washing off the unbound labeled glycan binding protein; and detecting the levels of the first tag and the second tag at the particular addresses of the microarray. This method also may include any of the following: the first tag is selected from a group consisting of biotin and digoxigenin; the glycan binding protein is selected from a group consisting of lectins and antibodies raised against particular glycan groups; the detecting step further including two-color rolling circle amplification; and the detecting step further including resonance-light scattering.

The above-described method of measuring the glycan level of a protein also may include the step of determining the relative signal from the glycan binding protein and the serum proteins bound to the antibodies of the microarray. Moreover, this method of the present invention may include the step of chemically blocking the antibodies on the microarray so that they do not bind to the labeled glycan binding protein, and this blocking step may be performed before the spotting step. Further, the biological sample may be blood Additionally, the present invention includes a second method of measuring the glycan level of a protein, including: providing a biological sample from a patient; providing a group of antibodies that bind specifically to serum proteins in the sample; spotting the group of antibodies at particular addresses on a microarray; incubating the sample on the microarray such that serum proteins in the sample are bound to the antibodies on the microarray; washing off unbound serum proteins from the microarray; providing a first glycan binding protein tagged with a first tag and a second glycan binding protein tagged with a second tag; incubating said first tagged glycan binding protein and said second tagged glycan binding protein on the microarray; washing off unbound first tagged glycan binding protein and unbound second tagged glycan binding protein; and detecting the levels of the first and second tags at particular addresses on the microarray. This method also may include any of the following: the first and second glycan binding proteins are selected from a group consisting of lectins and antibodies raised against particular glycan groups; the detecting step further including two-color rolling circle amplification; and the detecting step further including resonance-light scattering.

The second method of measuring the glycan level of a protein also may include the step of determining the relative signal from the first tag and the second tag at the particular addresses in the microarray. Additionally, this method of also may include the step of chemically blocking the antibodies on the microarray so that they do not bind the first or second glycan binding proteins, and this blocking step may be performed before the spotting step. Moreover, this method may include the step of chemically blocking the first tagged glycan binding protein and the second tagged glycan binding protein so that the first tagged glycan binding protein and the second tagged glycan binding protein do not bind to each other.

BRIEF DESCRIPTION OF THE DRAWING

FIGS. 11A-C show detection of glycans on antibody arrays. FIG. 11A shows a schematic drawing of one-color glycan detection. FIG. 11B shows a schematic drawing of two-color detection of glycans and proteins, using digoxigenin-labeled proteins. FIG. 11C shows scanned images of antibody arrays incubated with no serum, unlabeled serum, or digoxigenin-labeled serum.

FIG. 12A shows the chemical structures used to modify glycans on the spotted antibodies. FIG. 12B is a schematic drawing of blocking lectin binding to spotted antibodies. FIG. 12C is scanned images of antibody arrays, as follows: biotinylated AAL was incubated and detected on antibody arrays that were unblocked and incubated with PBS buffer (top left), unblocked and incubated with serum (top right), blocked and incubated with PBS buffer (bottom left), and blocked and incubated with serum (bottom right). FIG. 12D shows the ratios of AAL binding with serum incubation to without serum incubation after blocking (dark squares) and without blocking (open circles) are shown for each antibody.

FIG. 13A shows data for the lectin WGA pre-incubated with varying molar ratios of either N-,N-,diacetyl chitobiose (circles) or sucrose (squares), and FIG. 13B shows equivalent data from the lectin AAL pre-incubated with varying molar ratios of L-fucose (open circles) or sucrose (squares).

FIG. 14A shows the results of twenty-three control samples (white bars) and 23 cancer samples (dark bars) labeled with digoxigenin, incubated on antibody arrays, and detected with biotinylated AAL followed by streptavidin-phycoerythrin and Cy5-labeled anti-digoxigenin. FIG. 14B shows a Western blot analysis of seven to eight samples each from the cancer (lanes marked with C) and healthy (lanes marked with H) patients that were separated by gel electrophoresis, blotted, and probed with an antibody against haptoglobin (Hp), an antibody against alpha-2-macroglobulin (a2Mb), or AAL, as indicated.

FIG. 15A shows representative images of arrays using various (indicated) samples and detection antibodies. FIG. 15B is a graph showing the distribution of the levels of control samples (white bars) and carrier samples (dark bars). FIG. 15C is a scatter plot comparison of the levels detected at each capture antibody by either the anti-protein antibodies (y-axis) or the anti-CA19-9 antibody (x-axis) for each control patient serum sample (dark triangle) and each caner patient serum sample (open circles).

DETAILED DESCRIPTION OF THE PREFERRED EMBODIMENTS

Figure 1A:
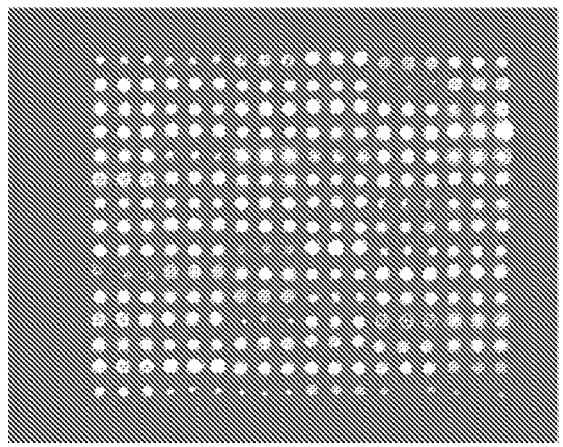
FIGS. 1A-D are scanned images of microarrays.
Figure 1B:
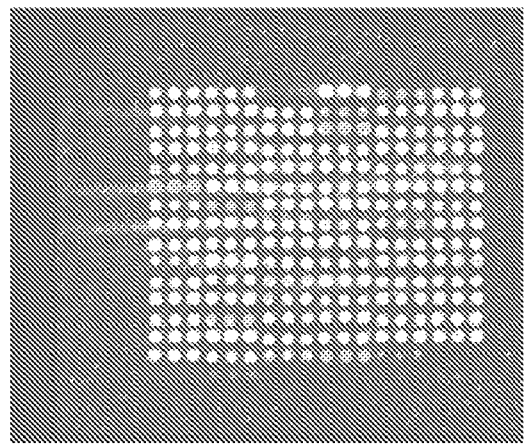
Figure 1C:
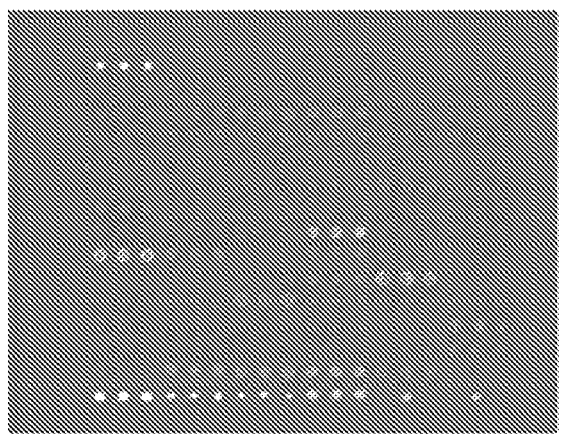
Figure 1D:
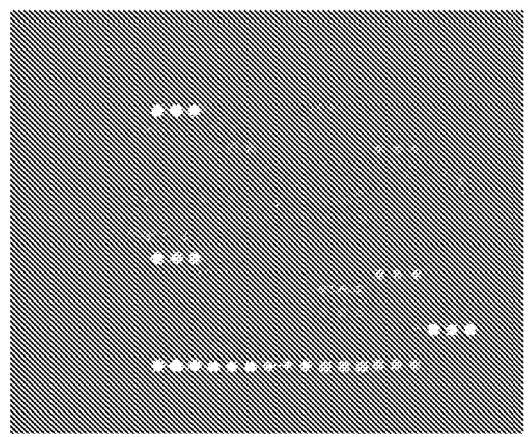

The preferred embodiments of the present invention may be understood more readily by reference to the following detailed description of preferred embodiments included hereafter.

Definitions

As used in the present application, "a" can mean one or more, depending on the context with which is it used; and "biological sample" means any fluid or other material derived from the body of a normal or diseased subject, such as blood, serum, plasma, lymph, urine, saliva, tears, cerebrospinal fluid, milk, amniotic fluid, bile, ascites fluid, pus, and the like. Also included within the meaning of the term "biological sample" is an organ or tissue extract and culture fluid in which any cells or tissue preparation from a subject has been incubated.

The present invention utilizes antibody microarray technology and applies it to the discovery of serum biomarkers for pancreatic cancer. Underlying this invention are the components involved in the application of antibody microarrays to biomarker research and the strategy used to profile serum protein abundances in serum samples from pancreatic cancer patients, patients with benign pancreatic disease, and healthy control subjects. The present invention probes the variation in multiple types of proteins in the sera and the use of the multiple measurements in combination for sample classification. More specifically, the present invention utilizes antibody microarrays to probe for, and determine the relative concentration of target proteins in a tissue sample of pancreatic cancer.

Microarrays are orderly arrangements of spatially resolved samples or probes (in the present invention, antibodies of known specificity to a particular protein).

The underlying concept of antibody microarray depends on binding between proteins and antibodies specific to proteins. Microarray technology adds automation to the process of resolving proteins of particular identity present in an analyte sample by labeling, preferably with fluorescent labels and subsequent binding to a specific antibody immobilized to a solid support in microarray format. An experiment with a single antibody microarray chip can provide simultaneous information on protein levels of many genes. Antibody microarray experiments employ common solid supports such as glass slides, upon which antibodies are deposited at specific locations (addresses).

Antibody microarray analysis generally involves injecting a fluorescently tagged sample of proteins into a chamber on a microarray slide to bind with antibodies having specific affinity for those proteins (and subsequent laser excitation at the interface of the array surface and the tagged sample; collection of fluorescence emissions by a lens; optical filtration of the fluorescence emissions; fluorescence detection; and quantification of intensity).

Antibodies used in connection with the present invention are commercially available or may be synthesized by standard methods known in the art.

High concentrations of certain protein products are indicative of pancreatic cancer. Such proteins are targets for early diagnostic assays of pancreatic cancer. The proteins can be detected by some assay means, e.g., immunoassay, in some accessible body fluid or tissue. For example, enzyme-linked immunosorbent assays (ELISAs) can be used to detect target protein concentrations or levels. ELISAs rely on antibodies coupled to an easily-assayed enzyme. ELISA can be used to detect the presence of proteins that are recognized by an antibody. A basic ELISA assay is a multiple-step procedure: 1) applying a sample or antigen to the microliter plate wells; 2) blocking all unbound sites to prevent false positive results; 3) adding antibody to the wells; 4) adding anti-mouse IgG conjugated to an enzyme; 5) reacting a substrate with the enzyme to produce a colored product, thus indicating a positive reaction. There are many variations of basic ELISAs.

The present invention contemplates a diagnostic kit for pancreatic cancer which identifies the presence of a tumor, and distinguishes it from benign conditions. For example, in combination with other markers, DCP could be used as an early stage screen for high-risk subjects or low-risk subjects; and as an MLD plate for determination of effective tumor treatment.

Diagnostic targets are especially useful if they can be detected in a biological sample before the cancer presents as a tumor, preferably, a protein or peptide ligand or, more preferably, an antibody is used to detect presence and levels of the target protein.

Suitable detectable labels include radioactive, fluorescent, fluorogenic, chromogenic, or other chemical labels. Useful radio labels, which are detected by gamma counter, scintillation counter, or auto radiography include $^{3}$H, $^{125}$I, $^{131}$I, $^{35}$S, and $^{14}$C.

Common fluorescent labels include fluorescein, rhodamine, dansyl, phycoerythrin, phycocyanin, allophycocyanin, o phthaldehyde, and fluoroescamine. The fluorophoor, such as the dansyl group, must be excited by light of a particular wavelength to fluoresce. The protein can also be labeled for detection using fluorescence-emitting metals such as $^{152}$Eu, or others of the lanthanide series.

An application of the present invention is screening of high-risk subjects—those with a family history of pancreatic cancer, or patients with other risk factors such as chronic pancreatitis, obesity, heavy smoking, and possibly diabetes. The prevalence of the disease, and therefore the positive predictive value of the test, would be higher in such a population. There are at least two possible tests: one to distinguish pancreatic disease from no pancreatic disease, and if that test is positive, another to distinguish malignant from benign disease. A positive result in both tests would dictate evaluation by a computed tomography (CT) scan or a more invasive modality such as endoscopic ultrasound (EUS) or endoscopic retrograde cholangiopancreatography (ERCP).

Further, the use and detection of various combinations of the biomarkers can provide more accurate and definitive detection of pancreatic cancer. The measurement of the biomarkers (e.g., DCP) in the blood serum or plasma could be used as a means to detect or more accurately diagnose or stage pancreatic cancer.

More specifically, as described in greater detail below, the inventor used antibody microarrays to probe the associations of multiple serum proteins with pancreatic cancer and to explore the use of combined measurements for sample classification. Serum samples from pancreatic cancer patients (n=61), patients with benign pancreatic disease (n=31), and healthy control subjects (n=50) were probed in replicate experiment sets by two-color, rolling-circle amplification on microarrays containing 92 antibodies and control proteins. The antibodies that had reproducibly different binding levels between the patient classes revealed different types of alterations, reflecting inflammation (high C-reactive protein, alpha-1-antitrypsin and serum amyloid A), immune response (high IgA), leakage of cell breakdown products (low plasma gelsolin), and possibly altered glycosylation and glucose regulation (high PIVKA-II). The accuracy of the most significant antibody microarray measurements was confirmed through immunoblot and antigen dilution experiments. Sample classification algorithms were formed using three different multiparametric methods. A logistic regression with forward selection method distinguished the cancer samples from the healthy control samples with a 90% and 93% sensitivity and a 90% and 94% specificity in duplicate experiment sets. The cancer samples were distinguished from the benign disease samples with a 95% and 92% sensitivity and a 88% and 74% specificity in duplicate experiment sets. The classification accuracies using each multiparametric method were significantly improved over those achieved using individual antibodies. Thus, this invention provides insights into the nature of the serum-protein alterations in pancreatic cancer patients and further validated the potential for improved sample classification accuracy using multiplexed measurements.

Four sets of antibody microarray profiling were performed on serum samples from pancreatic cancer patients and controls. In the first two experiment sets (sets one & two), 105 samples were used from four classes: healthy subjects (n=33), pancreatic adenocarcinoma patients (n=32), patients with benign pancreatic diseases (n=18), and patients with other gastro-intestinal malignancies (n=22). In the second two experiment sets (sets three & four), 142 samples were used from three classes: healthy subjects (n=50), pancreatic adenocarcinoma patients (n=61), and patients with benign pancreatic diseases (n=31). In each experiment set, a Two-Color, Rolling-Circle Amplification (TC-RCA) assay was used. The biotin-labeled proteins of each serum sample were mixed with digoxigenin-labeled proteins of a reference pool, made up of either all the samples or half the samples pooled together. The sample-reference mixes were incubated on antibody microarrays containing 88-90 antibodies and controls, and the relative binding of biotin-labeled proteins to digoxigenin-labeled proteins was detected at each antibody spot using TC-RCA. Table 1 presents the antibodies used in the studies along with a summary of performance characteristics.

TABLE 1

| Name | Company | Cat. # | Experiments Used | Experiments 1 & 2 | | | | | Experiments 3 & 4 | | | | |
|---|---|---|---|---|---|---|---|---|---|---|---|---|---|
| | | | | Avg. CV | Correlation | Corr. Overlap | Sample S/B 543 | Control S/B 543 | Avg. CV | Correlation | Corr. Overlap | Sample S/B 543 | Control S/B 543 |
| anti-α-fetoprotein (ab #1) | Biotrend | 4F16 | 2, 3, 4 | | | | 43.25 | 1.65 | 0.11 | 0.95 | 138 | 29.12 | 0.41 |
| anti-α-fetoprotein (ab #2) | Sigma | A8452 | 1, 2, 3, 4 | 0.16 | 0.73 | 89 | 26.99 | 4.76 | 0.16 | 0.79 | 138 | 50.10 | 17.36 |
| anti-α-1 antichymotrypsin | Fitzgerald | 10-A08 | 1, 2, 3, 4 | 0.19 | 0.67 | 88 | 20.04 | 0.09 | | | | 66.71 | 79.68 |
| anti-α-2 antiplasmin | Cedarlanes | CL20005AP | 1, 2, 3, 4 | 0.18 | 0.83 | 89 | 45.69 | 0.28 | 0.14 | 0.88 | 138 | 52.28 | 0.12 |
| anti-Albumin | Fitzgerald | 10-A75 | 1, 2, 3, 4 | 0.16 | 0.69 | 88 | 27.26 | 0.28 | 0.18 | 0.52 | 138 | 52.75 | 3.87 |
| anti-Alkaline phosphatase | Biotrend | 0300-0430 | 1, 2, 3, 4 | 0.12 | 0.83 | 89 | 22.61 | 0.13 | 0.13 | 0.95 | 136 | 51.97 | 1.00 |
| anti-Alpha 2-macroglobulin | Sigma | M1893 | 1, 2, 3, 4 | 0.13 | 0.89 | 89 | 98.66 | 0.58 | 0.11 | 0.90 | 138 | 69.72 | 0.27 |
| anti-Alpha-1-antitrypsin (ab #1) | Biotrend | 0640-5507 | 1, 2, 3, 4 | 0.14 | 0.80 | 87 | 24.83 | 0.20 | 0.14 | 0.83 | 137 | 58.01 | 1.30 |
| anti-Alpha-1-antitrypsin (ab #2) | GenWay | A10066F | 1, 2, 3, 4 | 0.23 | 0.58 | 89 | 17.53 | 4.97 | 0.15 | 0.84 | 138 | 42.91 | 0.80 |
| anti-Angiostatin | Oncogene Research | GF47 | 1, 2 | 0.33 | 0.66 | 14 | 22.22 | 0.06 | | | | | |
| anti-β2-Microglobulin | US Biological | M3890-05X | 1, 2, 3, 4 | 0.21 | 0.66 | 89 | 43.43 | 2.14 | | | | 54.45 | 85.30 |
| anti-CA 125 (ovarian cancer antigen) | US Biological | C0050-01 | 1, 2, 3, 4 | 0.15 | 0.50 | 64 | 7.70 | 0.38 | 0.15 | 0.75 | 138 | 24.85 | 0.11 |
| anti-CA 15-3 (breast cancer antigen MUC1) | US Biological | C0050-23 | 1, 2, 3, 4 | 0.11 | 0.82 | 78 | 9.66 | 0.08 | 0.11 | 0.90 | 138 | 21.33 | 0.04 |
| anti-CA 19-9 (cancer antigen Sialyl Lewis A) (ab #1) | US Biological | C0075-07 | 1, 2, 3, 4 | 0.16 | 0.66 | 89 | 20.05 | 0.12 | 0.12 | 0.87 | 135 | 27.88 | 0.60 |
| anti-CA 19-9 (cancer antigen Sialyl Lewis A) (ab #2) | US Biological | C0075-27 | 4 | | | | | | | | | 37.31 | 0.59 |
| anti-Catalase | AbCam | ab1877 | 1, 2, 3, 4 | 0.14 | 0.93 | 89 | 117.99 | 0.37 | 0.12 | 0.92 | 138 | 55.66 | 0.31 |
| anti-Cathepsin D | R&D Systems | AF1014 | 1, 2, 3, 4 | 0.16 | 0.95 | 89 | 36.62 | 0.10 | 0.11 | 0.98 | 137 | 43.03 | 0.23 |
| anti-Caveolin-1 | Sigma | C3237 | 1, 2, 3, 4 | 0.14 | 0.91 | 89 | 27.14 | 0.10 | 0.17 | 0.89 | 138 | 37.35 | 1.13 |
| anti-CD26 (dipeptidyl peptidase IV) | US Biological | C2277-10X | 1, 2, 3, 4 | 0.14 | 0.65 | 89 | 29.10 | 0.25 | 0.16 | 0.81 | 138 | 45.85 | 3.97 |
| anti-CEA (carcinoembryonic antigen) | US Biological | C1299-94 | 1, 2, 3, 4 | 0.14 | 0.75 | 89 | 25.50 | 0.11 | 0.11 | 0.89 | 138 | 30.13 | 0.63 |
| anti-Ceruloplasmin | Sigma | C0911 | 1, 2, 3, 4 | 0.23 | 0.89 | 89 | 43.84 | 0.10 | 0.11 | 0.97 | 134 | 25.82 | 0.02 |
| anti-Chorioric gonadotropin | AbCam | ab9502 | 1, 2, 3, 4 | 0.14 | 0.83 | 89 | 14.97 | 0.11 | 0.16 | 0.87 | 130 | 22.03 | 1.36 |
| anti-CKBB (creatin kinase BB is oenzyme) | US Biological | C7910-16 | 1, 2, 3, 4 | | | | 39.40 | 28.54 | 0.19 | 0.90 | 136 | 24.56 | 0.73 |
| anti-Complement C3 | Sigma | C7761 | 1, 2, 3, 4 | 0.12 | 0.82 | 89 | 76.29 | 0.28 | 0.10 | 0.88 | 138 | 49.51 | 0.42 |
| anti-Complement C5 | US Biological | C7850-24 | 1, 2, 3, 4 | 0.12 | 0.83 | 89 | 107.40 | 0.61 | 0.12 | 0.89 | 138 | 53.71 | 0.19 |
| anti-CRP (C reactive protein) (ab #1) | Sigma | C1688 | 1, 2, 3, 4 | 0.16 | 0.82 | 89 | 47.51 | 0.17 | 0.13 | 0.87 | 138 | 36.05 | 0.29 |
| anti-CRP (C reactive protein) (ab #2) | US Biological | C7907-10 | 1, 2, 3, 4 | 0.22 | 0.96 | 71 | 38.86 | 0.43 | 0.18 | 0.98 | 107 | 45.50 | 0.50 |
| anti-Ferritin | US Biological | F4015-17 | 1, 2, 3, 4 | 0.22 | 0.90 | 88 | 50.87 | 0.46 | 0.14 | 0.97 | 131 | 37.88 | 3.61 |
| anti-Gelsolin | Sigma | G4896 | 1, 2, 3, 4 | 0.17 | 0.85 | 89 | 38.73 | 0.10 | 0.15 | 0.82 | 124 | 18.25 | 0.05 |
| anti-GST (glutathione S transferase) | US Biological | G8135-05 | 1, 2, 3, 4 | 0.19 | 0.93 | 89 | 32.95 | 0.09 | 0.18 | 0.91 | 136 | 40.35 | 0.12 |
| anti-Haptoglobin | Biotrend | 4890-0004 | 1, 2, 3, 4 | 0.12 | 0.92 | 82 | 20.94 | 0.11 | 0.17 | 0.86 | 137 | 38.68 | 1.45 |
| anti-HC II (heparin cofactor II) | Cedarlanes | CL20070AP | 1, 2, 3, 4 | 0.27 | 0.78 | 89 | 63.52 | 0.14 | 0.21 | 0.84 | 138 | 52.31 | 0.10 |

TABLE 1-continued

| Name | Company | Cat. # | Experiments Used | Experiments 1 & 2 ||||| Experiments 3 & 4 |||||
|---|---|---|---|---|---|---|---|---|---|---|---|---|---|
| | | | | Avg. CV | Corre-lation | Corr. Over-lap | Sample S/B 543 | Control S/B 543 | Avg. CV | Corre-lation | Corr. Over-lap | Sample S/B 543 | Control S/B 543 |
| anti-Hemoglobin | Bethyl | E80-135(kit component) | 1, 2, 3, 4 | 0.18 | 0.90 | 88 | 70.48 | 0.75 | 0.12 | 0.94 | 137 | 51.81 | 0.12 |
| anti-HGF (hepatocyte growth factor) | R&D Systems | MAB294 | 1, 2, 3, 4 | 0.14 | 0.78 | 87 | 16.78 | 0.09 | 0.13 | 0.86 | 138 | 43.72 | 1.82 |
| anti-IgA | Bethyl | E80-102(kit component) | 1, 2, 3, 4 | 0.14 | 0.85 | 88 | 109.74 | 1.88 | 0.15 | 0.82 | 136 | 90.69 | 0.31 |
| anti-IG FBP-3 (insulin-like growth factor binding protein) | R&D Systems | MAB305 | 1, 2, 3, 4 | 0.15 | 0.81 | 72 | 9.05 | 0.08 | 0.10 | 0.92 | 134 | 26.31 | 0.44 |
| anti-IG F-I (insulin-like growth factor) | R&D Systems | AF-291-NA | 1, 2, 3, 4 | 0.17 | 0.92 | 87 | 28.05 | 0.13 | 0.32 | 0.89 | 136 | 35.61 | 0.16 |
| anti-IgG1 | Zymed Laboratories | 05-3300 | 1, 2, 3, 4 | 0.11 | 0.89 | 89 | 69.42 | 0.30 | 0.11 | 0.91 | 138 | 85.58 | 0.37 |
| anti-IgG-Fc | Bethyl | E80-104(kit component) | 1, 2, 3, 4 | 0.12 | 0.82 | 89 | 96.94 | 1.60 | 0.14 | 0.81 | 138 | 116.30 | 1.64 |
| anti-IgM | Jackson Immuno-research | 109-005-043 | 1, 2, 3, 4 | 0.20 | 0.75 | 89 | 46.90 | 0.16 | 0.15 | 0.90 | 138 | 90.48 | 22.38 |
| anti-IL-1α (ab #1) | Research Diagnostics | RDI-IL1AabrP | 1, 2, 3, 4 | 0.23 | 0.63 | 62 | 8.90 | 0.03 | 0.16 | 0.88 | 137 | 26.64 | 0.19 |
| anti-IL-1α (ab #2) | GenWay | A22493 | 1, 2, 3, 4 | 0.16 | 0.94 | 88 | 31.01 | 0.34 | 0.21 | 0.91 | 138 | 31.22 | 0.14 |
| anti-IL-1β | Research Diagnostics | RDI-IL1BabrP | 1, 2, 3, 4 | | | 0 | 0.91 | 0.03 | 0.21 | 0.77 | 92 | 8.56 | 0.02 |
| anti-IL-2 | R&D Systems | MAB202 | 1, 2, 3, 4 | 0.13 | 0.83 | 87 | 15.06 | 0.07 | 0.10 | 0.92 | 138 | 26.50 | 0.18 |
| anti-IL-2Rα | R&D Systems | MAB223 | 1, 2, 3, 4 | 0.14 | 0.73 | 59 | 6.79 | 0.06 | 0.10 | 0.92 | 128 | 24.25 | 0.41 |
| anti-IL-6 (ab #1) | Sigma | 17901 | 1, 2, 3, 4 | 0.32 | 0.63 | 86 | 28.45 | 0.07 | 0.15 | 0.72 | 92 | 16.76 | 0.29 |
| anti-IL-6 (ab #2) | R&D Systems | MAB206 | 1, 2, 3, 4 | 0.15 | 0.74 | 73 | 9.54 | 0.08 | 0.11 | 0.90 | 126 | 21.36 | 0.42 |
| anti-IL-6 sR | R&D Systems | AF-227-NA | 1, 2, 3, 4 | 0.34 | 0.36 | 18 | 4.89 | 0.03 | 0.10 | 0.89 | 138 | 40.33 | 0.40 |
| anti-IL-8 (ab #1) | R&D Systems | AB-208-NA | 1, 2, 3, 4 | 0.17 | 0.93 | 87 | 27.40 | 0.20 | 0.20 | 0.71 | 137 | 31.00 | 0.97 |
| anti-IL-8 (ab #2) | GenWay | A21030F | 1, 2, 3, 4 | 0.17 | 0.91 | 86 | 22.10 | 0.12 | 0.17 | 0.94 | 136 | 28.37 | 0.05 |
| anti-IL-10 (ab #1) | R&D Systems | MAB217 | 1, 2, 3, 4 | 0.19 | 0.70 | 83 | 11.80 | 0.05 | 0.14 | 0.82 | 138 | 41.39 | 0.92 |
| anti-IL-10 (ab #2) | GenWay | A21031F | 1, 2, 3, 4 | 0.15 | 0.94 | 89 | 29.65 | 0.43 | 0.18 | 0.94 | 102 | 20.97 | 0.11 |
| anti-KRT18 (keratin, type I cytoskelatal 18) | GenWay | A22753 | 1, 2, 3, 4 | 0.19 | 0.92 | 89 | 32.35 | 0.25 | 0.17 | 0.94 | 138 | 30.62 | 0.87 |
| anti-Laminin (ab #1) | Sigma | L 8271 | 1, 2, 3, 4 | 0.22 | 0.92 | 89 | 43.26 | 0.75 | 0.11 | 0.93 | 138 | 38.49 | 0.04 |
| anti-Laminin (ab #2) | GenWay | A20044F | 1, 2, 3, 4 | 0.15 | 0.95 | 89 | 30.86 | 0.09 | 0.16 | 0.90 | 138 | 37.99 | 0.18 |
| anti-Lipase | US Biological | L2496-02 | 1, 2, 3, 4 | 0.14 | 0.77 | 87 | 11.47 | 0.12 | 0.18 | 0.90 | 138 | 35.04 | 0.49 |
| anti-M2-PK-(pyruvate kinase type M2) | Scehbo | S-1 | 1, 2, 3, 4 | 1.02 | | 1 | 5.24 | 0.08 | 0.19 | 0.80 | 127 | 19.77 | 0.80 |
| anti-MCP-1 (monocyte chemoatractant protein) | Genex Biosciences Inc. | GEA6043-2 | 1, 2, 3, 4 | 0.16 | 0.89 | 89 | 105.34 | 0.91 | 0.12 | 0.93 | 138 | 50.75 | 0.28 |
| anti-MPM2(Ser/Thr, Pro phosphorylated mitotic protein) | US Biological | M4685 | 1, 2, 3, 4 | 0.19 | 0.61 | 88 | 15.95 | 0.05 | 0.18 | 0.67 | 138 | 36.53 | 0.26 |
| anti-Ornithine decarb oxylase | Neomarkers | MS-464-P1ABX | 1, 2, 3, 4 | 0.19 | 0.75 | 79 | 13.08 | 0.29 | 0.13 | 0.83 | 138 | 46.81 | 0.92 |
| anti-PAI-1 (plasminogen activator inhibitor type-1) | Cedarlanes | CL20140A | 1, 2, 3, 4 | 0.18 | 0.89 | 89 | 57.96 | 0.38 | 0.16 | 0.96 | 136 | 38.5 | 0.25 |
| anti-PIVKA-II (protein induced vitamin K antagonist) | Crystal Chem Inc. | 08040 | 1, 2, 3, 4 | 0.18 | 0.60 | 89 | 23.37 | 0.20 | 0.18 | 0.93 | 138 | 40.45 | 0.82 |
| anti-Plasminogen | US Biological | P4256-27A | 1, 2, 3, 4 | 0.17 | 0.93 | 88 | 41.94 | 0.11 | 0.16 | 0.81 | 138 | 40.61 | 1.04 |
| anti-Serum amyloid A | AbCam | ab687 | 1, 2, 3, 4 | | | 0 | 5.69 | 0.02 | 0.20 | 0.88 | 138 | 28.34 | 0.09 |

TABLE 1-continued

| | | | | Experiments 1 & 2 | | | | | Experiments 3 & 4 | | | |
| --- | --- | --- | --- | --- | --- | --- | --- | --- | --- | --- | --- | --- |
| Name | Company | Cat. # | Experiments Used | Avg. CV | Correlation | Corr. Overlap | Sample S/B 543 | Control S/B 543 | Avg. CV | Correlation | Corr. Overlap | Sample S/B 543 | Control S/B 543 |
| anti-sTNFR (soluble tumor necrosis factor receptor 1) | US Biological | T9162 | 1, 2, 3, 4 | 0.24 | 0.59 | 58 | 6.11 | 0.03 | 0.19 | 0.82 | 133 | 18.70 | 0.05 |
| anti-Thioredoxin | Medical & Biological Laboratories | M063-3 | 1, 2, 3, 4 | 0.26 | 0.49 | 80 | 11.28 | 0.03 | 0.17 | 0.75 | 138 | 45.15 | 1.75 |
| anti-TIMP-1 (tissue inhibitor of matrix metalloproteinases-1) | BIOMOL | SA-373 | 1, 2, 3, 4 | 0.25 | 0.61 | 69 | 9.26 | 0.06 | 0.15 | 0.90 | 138 | 30.73 | 0.53 |
| anti-TNFα | Oncogene Research | GF31 | 1, 2, 3, 4 | 0.33 | 0.67 | 32 | 8.24 | 0.12 | 0.16 | 0.77 | 138 | 40.08 | 0.67 |
| anti-Transferrin | Bethyl | E80-128(kit component) | 3, 4 | | | | | | 0.14 | 0.76 | 138 | 71.30 | 0.15 |
| anti-Troponin I | Chemicon Intl. Inc. | MAB1691 | 1, 2, 3, 4 | 0.15 | 0.81 | 89 | 22.04 | 0.17 | 0.13 | 0.89 | 138 | 42.64 | 1.3 |
| anti-TSP-1 (thrombospondin-1) | Neomarkers | MS-419-P1ABX | 1, 2, 3, 4 | 0.11 | 0.85 | 81 | 1298 | 0.12 | 0.11 | 0.88 | 138 | 20.54 | −0.01 |

As a quality control measure to confirm proper collection and treatment of the data, independently-collected ELISA measurements from IgM and hemoglobin were compared to the microarray measurements. The correlations for IgM were 0.74, 0.69, 0.74 and 0.76 for sets one through four, respectively, and the correlations for hemoglobin were 0.79, 0.84, 0.76 and 0.83 for sets one through four, respectively, which were sufficient confirmation of data quality.

Sets one & two used a hydrogel that was activated with N-hydroxysuccinimide functional groups to provide covalent linkage of the spotted proteins and antibodies. Sets three & four used glass microscope slides that were each coated with an ultra-thin layer of nitrocellulose. Representative scans of the microarrays show some differences between the two surfaces (FIG. 1A-D).

FIG. 1 shows arrays from sets one & two, performed on hydrogels in (A) and (C), and arrays from sets three & four, performed on nitrocellulose in (B) and (D). The arrays were incubated either with labeled serum (A & B) or unlabeled serum (C & D), which served as negative controls. The spacing between the spots is 300 µm in A & C and 240 µm in B & D. The antibodies and proteins were spotted in triplicate. The top left triplet and the bottom row were control spots: digoxigenin-labeled and biotin-labeled BSA. The microarray scanner settings and the image brightness and contrast settings were optimally chosen for each surface type, with slight differences between the settings for A & C and the settings for B & D.

Both surfaces showed good signal-to-background ratios. The hydrogel surface often showed abnormal spot morphologies—incomplete spots or rings around the spots. Very small spots also were sometimes present, as shown in FIG. 1A. Negative controls were performed on each surface (FIGS. 1C and 1D), in which arrays that had been incubated with unlabeled serum samples were processed normally (see the "Control S/B 543" columns in Table 2). Two antibodies, anti-β2 microglobulin and anti-alpha-1-antichymotrypsin, showed strong signals in both color channels in each negative control experiment, presumably due to interactions between these antibodies and the detection antibodies. These two antibodies were removed from subsequent analyses.

Reproducibility between replicate experiments is critical to the effectiveness of protein profiling experiments and can be used as a means to filter out unreliable antibodies. Miller, J. C., Zhou, H., Kwekel, J., Cavallo, R., Burke, J., Butler, E. B., Teh, B. S., and Haab, B. B. Antibody microarray profiling of human prostate cancer sera: antibody screening and identification of potential biomarkers. Proteomics, 3: 56-63, 2003. The reproducibility of each antibody was assessed by calculating both the average coefficient of variation (CV) and the correlation between duplicate experiment sets, for sets one & two and for sets three & four (Table 2, columns 5 and 10 for the CVs, columns 6 and 11 for the correlations). The median CV was lower in sets three & four than in sets one & two (0.148 and 0.162, respectively, p=0.008). The CVs are distributed from 12-22% for experiments three & four, whereas they generally range from 12-28% (with some high outliers) for experiments one & two (FIG. 2A).

Figure 2A:
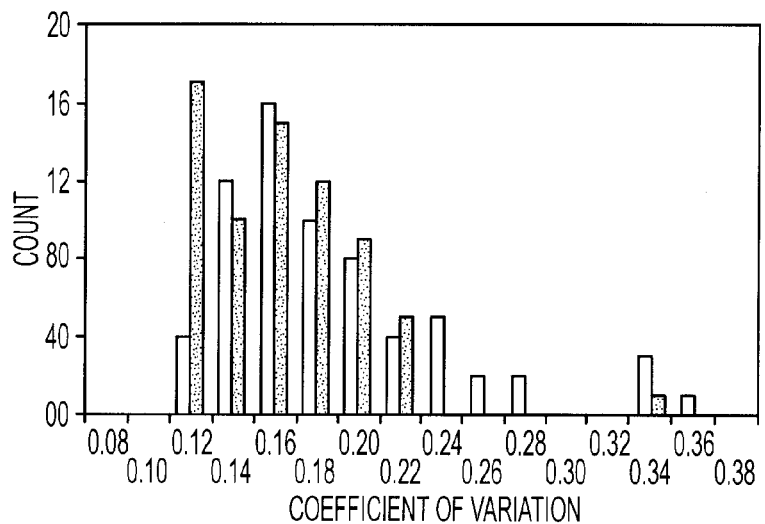
FIGS. 2A-C are histograms showing antibody performance and comparison of surface types.
Figure 2B:
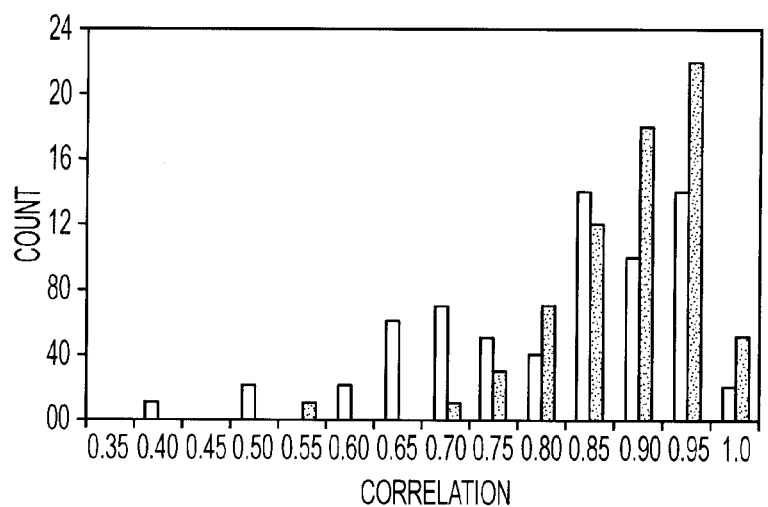
Figure 2C:
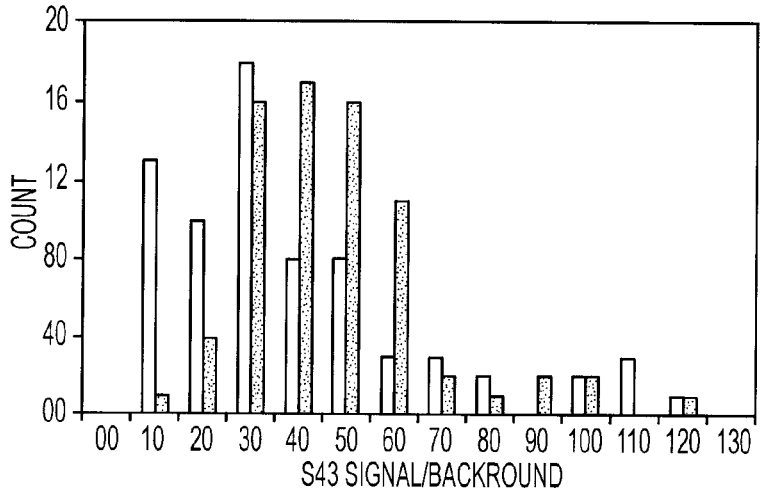

FIG. 2A-C generally shows histograms of antibody performance and comparisons of surface types. Each histogram is a plot of the number of antibodies (vertical axis) that have an average value within the given bin range (horizontal axis). The light bars refer to experiment sets one & two (hydrogel surfaces), and the dark bars refer to experiment sets three & four (thin nitrocellulose surfaces). FIG. 2A shows the coefficient of variation (CV) for each antibody between replicate data in experiment sets one & two or between experiment sets three & four. The CVs were averaged over all the arrays in an experiment set, resulting in a single average for each antibody in each experiment sets. FIG. 2B, for each antibody, shows correlations between all the measurements in sets one & two or between all the measurements in sets three & four. FIG. 2C, for each antibody, shows the ratios of the background-subtracted signals to the backgrounds on every array, and the geometric mean of the S/Bs over all the arrays was calculated, for both experiment sets one & two and three & four.

A similar trend was seen in the correlations between replicate sets (Table 1, columns 6 and 11), which were higher in sets three & four than in sets one & two (medians 0.887 and 0.822, respectively, p<0.001). The distributions ranged from 0.7 to nearly 1 for sets three & four and from 0.6 to nearly 1 for sets one & two, with low-correlation outliers for each (FIG. 2B). The surfaces also were compared according to the signal strengths of fluorescence for each of the antibodies, relative to the background levels from the surface surrounding the antibody spots (Table 1, columns 8 and 13). The distribution of signal-to-background ratios (S/B) were weighted to higher values in the nitrocellulose experiments in comparison to the hydrogel experiments (FIG. 2C), but not significantly so (medians 38 and 27, respectively, p=0.12). The individual antibodies can be considered independent assays, and a consistent trend over many different antibodies gives added significance to the observations.

The inventor next identified antibodies with significantly different binding patterns between the patient classes. For this and subsequent analyses the inventor used experiment sets three & four, based on the results of the analyses above. Sixty-nine antibodies were used in these analyses, after removal of control antibodies and proteins (ten), antibodies that failed gel-based quality control (nine), and antibodies that showed binding in the negative control experiments (two). All 69 of the antibodies passed a reproducibility criterion, based on a 99% confidence threshold in the correlation between sets three & four. Several antibodies showed binding levels that were statistically different (p<0.05) between each of the patient classes in both experiment sets three and four (Table 3). The p-value for both set 3 and set 4 are given in Table 2 for the indicated comparisons.

CA15-3 were consistently higher, and anti-serum amyloid A was consistently lower, in cancer relative to benign disease. The anti-CA19-9 (ab #2) antibody was used only in set 4 (not shown in Table 2). This antibody was higher in cancer relative to normal (p<0.001) and relative to benign disease (p<0.001). These analyses show the extensive differences between the disease classes and the healthy class, in addition to the considerable similarity between the cancer and benign classes. Correlation in the binding profiles of the samples and the antibodies can be examined in cluster image maps (Eisen, M. B., Spellman, P. T., Brown, P. O., and Botstein, D. Cluster analysis and display of genome-wide expression patterns. Proc. Natl. Acad. Sci. USA, 95: 14863-14868, 1998) for all the antibodies and for only the antibodies that are different between the patient classes.

TABLE 3

| Method 1 | Method 2 | Method 3 |
|---|---|---|
| Healthy vs. Cancer | | |
| anti-CRP (ab #2) | anti-$\alpha$-2 antiplasmin | anti-Alpha-1-antitrypsin (ab #2) |
| anti-Gelsolin | anti-Alpha-1-antitrypsin (ab #1) | anti-CRP (ab #2) |
| anti-IgA | anti-Alpha-1-antitrypsin (ab #2) | anti-Gelsolin |
| anti-IL-1$\beta$ | anti-Cathepsin D | |
| anti-IL-6 (ab #1) | anti-Complement C5 | |
| anti-PIVKA-II | anti-CRP (ab #2) | |
| anti-Plasminogen | anti-Gelsolin | |

TABLE 2

| Healthy vs. Cancer | | Healthy vs. Benign | | Cancer vs. Benign | |
|---|---|---|---|---|---|
| Higher in Cancer | p-value | Higher in Benign | p-value | Higher in Cancer | p-value |
| anti-CRP (ab #2) | <0.001, <0.001 | anti-Alpha-1-antitrypsin (ab #2) | <0.001, <0.001 | anti-PIVKA-II | 0.005, 0.031 |
| anti-PIVKA-II | <0.001, <0.001 | anti-serum amyloid A | <0.001, <0.001 | anti-CA15-3 | 0.024, 0.05 |
| anti-Alpha-1-antitrypsin (ab #2) | 0.004, <0.001 | anti-CRP (ab #2) | <0.001, <0.001 | | |
| anti-IgA | 0.014, <0.001 | anti-alkaline phosphatase | 0.006, 0.007 | | |
| anti-Alpha-1-antitrypsin (ab #1) | 0.021, <0.001 | | | | |
| anti-Cathepsin D | 0.009, 0.014 | | | | |
| anti-alkaline phosphatase | 0.007, 0.02 | | | | |
| Lower in Cancer | p-value | Lower in Benign | p-value | Lower in Cancer | p-value |
| anti-Gelsolin | <0.001, <0.001 | anti-Plasminogen | <0.001, 0.001 | anti-serum amyloid A | 0.006, 0.002 |
| anti-TNF$\alpha$ | <0.001, <0.001 | anti-MPM2 | <0.001, 0.004 | | |
| anti-MPM2 | 0.003, 0.002 | anti-M2-PK | 0.009, <0.001 | | |
| anti-IL-6 sR | 0.005, <0.001 | anti-IL-6 sR | 0.011, 0.002 | | |
| anti-IL-8 (ab #1) | 0.003, 0.004 | anti-IL-8 (ab #1) | 0.01, 0.002 | | |
| anti-Transferin | 0.001, 0.006 | anti-$\alpha$-2 antiplasmin | 0.009, 0.005 | | |
| anti-Troponin T | 0.016, 0.013 | anti-PAI-1 | 0.012, 0.006 | | |
| anti-Thioredoxin | 0.034, <0.001 | anti-CA15-3 | 0.01, 0.012 | | |
| anti-$\alpha$-2 antiplasmin | 0.028, 0.011 | anti-Gelsolin | 0.026, 0.001 | | |
| anti-IGF-I | 0.025, 0.045 | anti-CA125 | 0.02, 0.018 | | |
| | | anti-$\alpha$-fetoprotein (ab #2) | 0.018, 0.029 | | |
| | | anti-CEA | 0.007, 0.043 | | |
| | | anti-Transferrin | 0.03, 0.023 | | |
| | | anti-CRP (ab #1) | 0.021, 0.036 | | |
| | | anti-TNF$\alpha$ | 0.049, 0.023 | | |

A smaller number of antibodies (not shown in Table 2) were significant in either set three or set four, but not both: ten, nine, and five antibodies in the cancer-healthy, benign-healthy, and cancer-benign comparisons, respectively. These antibodies may have statistically different binding levels between the groups, but the differences were not strong enough to pass the p<0.05 threshold in both sets. Many differences were shared between the cancer-healthy and the benign-healthy comparisons. Fewer antibodies distinguished the cancer and benign classes: only anti-PIVKA-II and anti- TABLE 3-continued

| Method 1 | Method 2 | Method 3 |
|---|---|---|
| anti-Troponin T | anti-Haptoglobin | |
| | anti-IgA | |
| | anti-IL-6 (ab #1) | |
| | anti-PIVKA-II | |
| | anti-Plasminogen | |
| | anti-Troponin T | |

TABLE 3-continued

| Method 1 | Method 2 | Method 3 |
|---|---|---|
| Healthy vs. Benign | | |
| anti-Alkaline phosphatase | anti-α-2 antiplasmin | anti-CRP (ab #2) |
| anti-CRP (ab #2) | anti-CRP (ab #2) | anti-Plasminogen |
| anti-PAI-1 | anti-IgA | |
| anti-Plasminogen | anti-Plasminogen | |
| anti-Serum amyloid A | anti-TIMP-1 | |
| Cancer vs. Benign | | |
| None | anti-Serum amyloid A | anti-CRP (ab #1) |
| | | anti-Serum amyloid A |

Figure 8:
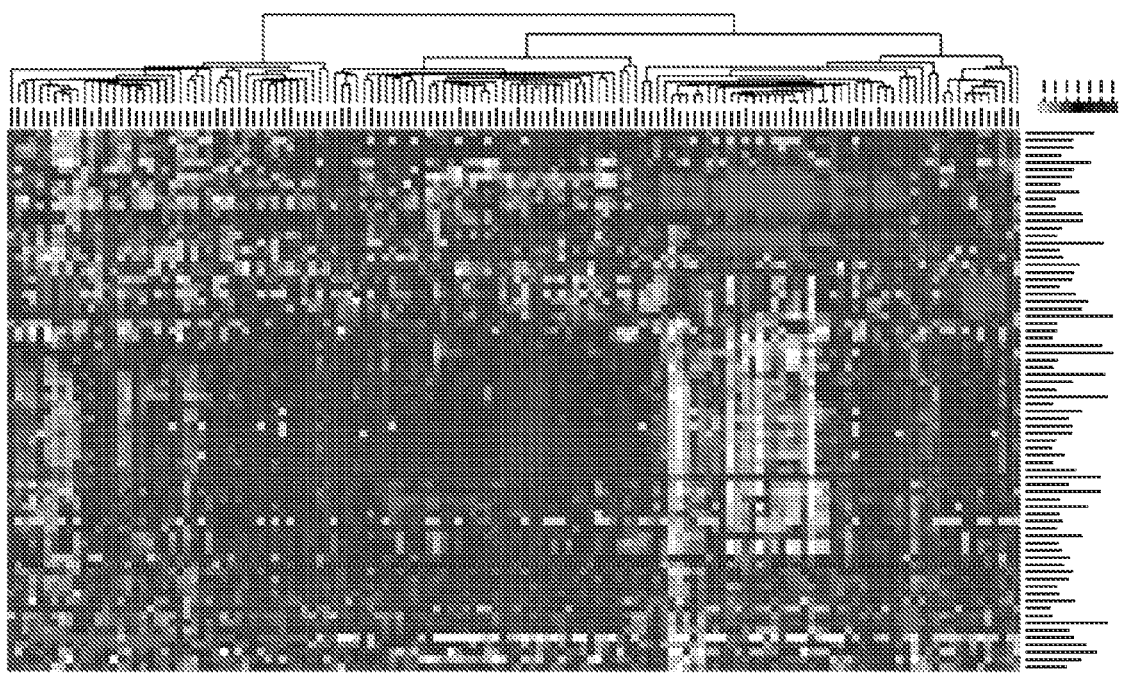
FIGS. 8 and 9A-C are cluster image maps for all the antibodies and for the antibodies that are different between the patient classes.

FIG. 8 shows two-way hierarchical clustering of the microarray data from set 4. Microarray data from 138 serum samples (horizontal axis) and 71 reproducible antibodies (vertical axis) were logged and median centered prior to clustering. Independently-collected ELISA measurements are included for the proteins IgM and hemoglobin. The total protein concentration of each serum sample was also included in the cluster.

Figure 9A:
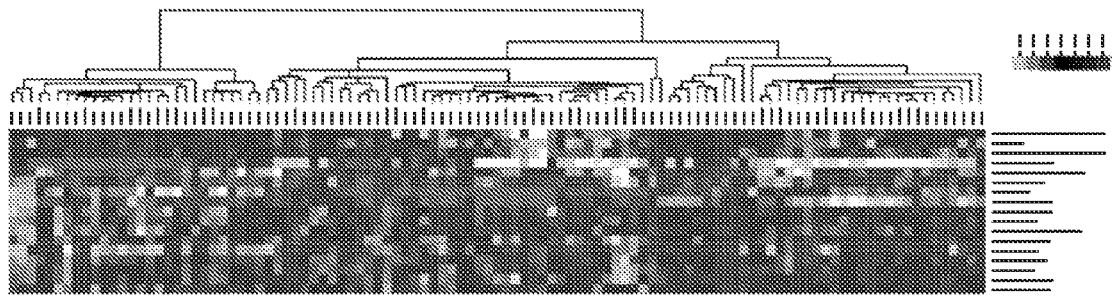
Figure 9B:
Figure 9C:
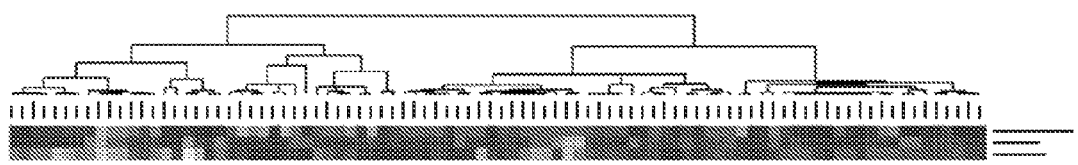

FIG. 9A-C shows two-way hierarchical clustering of antibody response that discriminates between patient classes in both experiment set 3 and experiment set 4 with $p<0.05$. Higher antibody response in cancer patients versus healthy controls, benign patients versus healthy controls, and cancer patients versus benign patients are indicated for FIGS. 9A, 9B, and 9C, respectively.

The inventor examined other relationships between the samples. The benign-class samples consisted of 15 samples from chronic pancreatitis patients and 15 samples from acute pancreatitis patients. Anti-CRP (ab #2) and anti-serum amyloid A were higher in acute pancreatitis in both sets three ($p=0.005$ and 0.04, respectively) and four ($p=0.009$ and 0.003, respectively), and anti-alpha2 macroglobulin was higher in chronic pancreatitis in sets three & four ($p=0.06$ and 0.02, respectively). Thus, using these antibodies, acute and chronic pancreatitis samples are very similar except for major acute phase reactants. Precise staging information was available on the cancer samples from ENH, and the samples were grouped by stage I and II ($n=13$) and stage III and IV ($n=23$). Four antibodies (anti-troponin T, anti-CD26, anti-IL-10, and anti-IL1α) had binding levels lower in the early stage patients, and none were higher, in both sets three & four. Some antibodies were elevated relative to healthy only in early stage cancer (anti-cathepsin D) or only in late stage cancer (anti-alpha-1-antitrypsin (ab #2), anti-von Willebrand factor, and anti-IgA). Thus variation in certain protein levels may occur in association with cancer stage.

As outlined recently (Ransohoff, D. F. Bias as a threat to the validity of cancer molecular-marker research. Nat Rev Cancer, 5: 142-149, 2005), the design of experiments comparing groups of specimens must be carefully examined to identify potential sources of bias that could produce misleading results. Ideally, the patient classes should have equivalent demographic characteristics, the samples should be acquired and handled using precisely the same protocols, and the experimental processing of the samples should be randomized. The samples were treated equivalently once assembled at the VARI, but sources of bias could have been introduced prior to their being assembled. A demographic analysis of the samples showed that the gender distributions were statistically similar between the classes, but the healthy control subjects were younger than both other classes, and the benign class was younger than the cancer class (Table 6 herein below).

To gain more insight into the potential role of age in introducing systematic variation, the inventor divided samples from the same class and same site by age—separating the top third from the bottom third—and performed a t-test analysis between the groups. The control samples from WM, the cancer samples from ENH, and the benign samples from ENH were examined, using data from both sets three & four. The mean and standard deviation ages of the older and younger subjects in each group were 53.8+/−6.6 and 27.1+/−3.4 (controls); 81.6+/−3.8 and 60.9+/−5.3 (cancer); and 73.4+/−6.1 and 37.0+/−10.5 (benign). Each group had only one antibody with a significant difference ($p<0.05$) in both experiment sets between the samples from the older and younger patients. Anti-ceruloplasmin was higher in the younger control subjects, anti-plasminogen was higher in the younger cancer subjects, and anti-alpha2-macroglobulin was higher in the older patients with benign disease. Of these antibodies, only anti-plasminogen was present in Table 3. This analysis does not conclusively rule out the influence of age, but for the antibodies used in these experiments, age differences between the classes do not seem to be a major source of potential bias in the comparisons.

Most of the samples were collected from ENH, but additional samples from the pancreatic cancer and healthy control classes were collected from WM and UM, respectively. The inclusion of cancer and control samples from different sites could potentially introduce bias, perhaps due to effects caused by differences in collection and handling procedures. To examine this issue further, the inventor compared the binding profiles between samples that were of the same patient class but from different sites. In the comparison of the cancer samples from ENH and WM, only one antibody showed a statistical difference ($p<0.05$) in mean protein binding. This antibody (anti-haptoglobin) did not appear in Table 3. Five antibodies had statistically different binding levels between the control samples from ENH and the control samples from UM in both experiment sets three & four. The trend was not consistent—two were higher in the ENH samples and three were lower. None of these antibodies appeared in Table 3. Also, no significant differences in serum total protein concentrations existed between the controls from the different sites or the cancer samples from the different sites. Therefore systematic variation between the samples collected at different sites also seems to have not played a large role in defining the observed differences between the sample classes.

Figure 3:
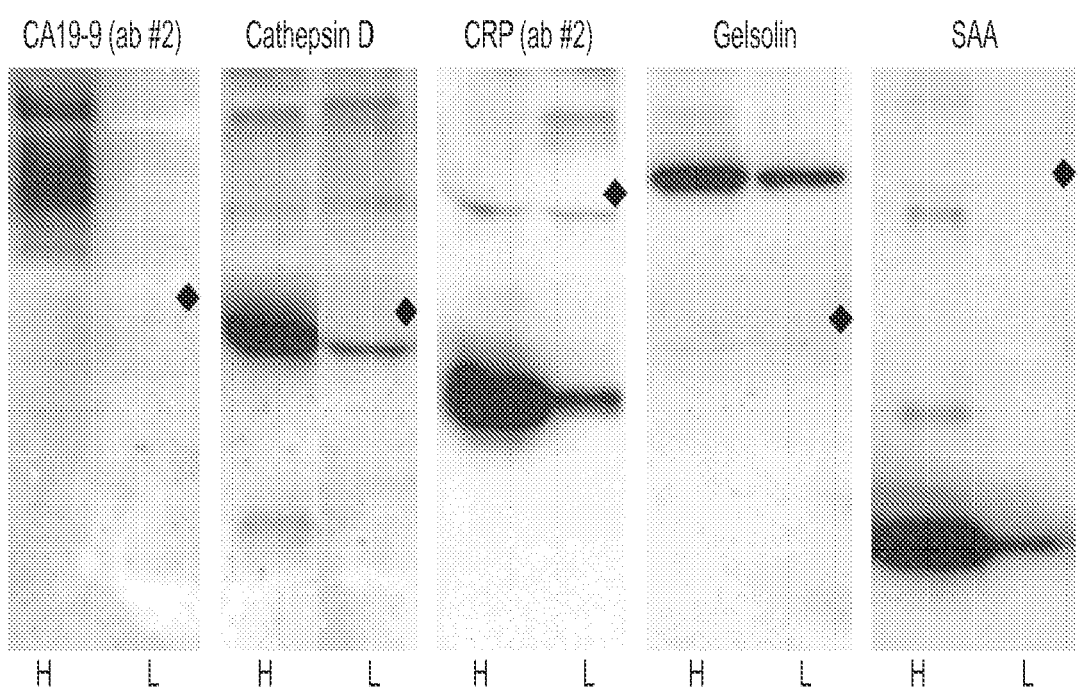
FIG. 3 shows a Western blot analysis characterizing selected antibodies.

The validation and characterization of the binding properties of the antibodies is critical to the interpretation and use of the antibody microarray profiles. Nine antibodies were selected for western blot analysis from those with the highest significance in Table 3, especially those higher in the cancer or benign classes. For each antibody, serum samples were chosen according to the binding level in the microarray data: two-to-four samples that showed high binding and two-to-four samples that showed low binding to that antibody. Representative lanes from the immunoblots revealed the level of concordance with the microarray data (FIG. 3). FIG. 3 depicts a characterization of selected antibodies using Western blot analysis. Fifty µg of serum proteins from patients exhibiting high (H) microarray reactivity or low (L) microarray reactivity for the indicated antibody were electrophoresed on polyacrylamide gels. The separated proteins were transferred to nitrocellulose and the antigens were detected with 10 µg/ml of biotinylated antibody followed by peroxidase-conjugated streptavidin and chemiluminescent development. The diamond in each blot indicates the position of the 50 kDa molecular weight marker. Results shown are representative of four patient samples run in at least two different experiments.

For the antibodies shown in FIG. 3, the trends observed in the microarray data were observed in the immunoblot, and the bands appeared at molecular weights consistent with each antibody's target, with minimal additional bands.

The blot of anti-PIVKA-II also confirmed the trends in the microarray data. The blots of anti-plasminogen and anti-alkaline phosphatase failed to showed bands at the expected molecular weights, perhaps due to a failure of the antibody to recognize the denatured target. The blot of anti-alpha-1-antitypsin (ab #1) showed the correct size band, but the differences between the high and low serum samples were too subtle to verify on the blot.

Other antibodies were tested by probing their response to dilutions of purified cognate antigens. Purified proteins corresponding to the analytes of ten of the antibodies were spiked in to either human serum or BSA at various concentrations. These mixes were labeled, mixed with a differentially-labeled reference solution, and analyzed on antibody microarrays. The correspondence between the observed changes in signal intensity at each antibody and the expected changes, based on the known analyte concentrations, indicates the accuracy of the antibody binding (FIG. 4).

Figure 4A:
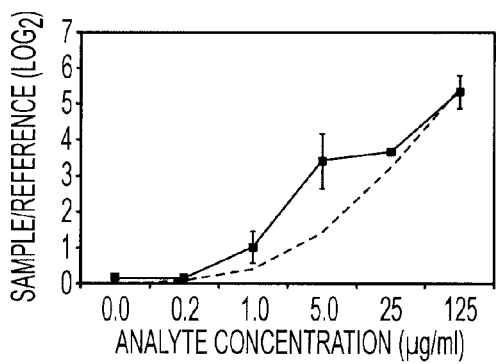
FIG. 4A-H are graphs showing antibody binding validation using analyte dilutions.
Figure 4B:
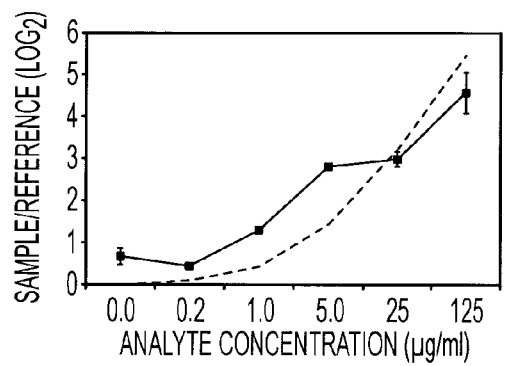
Figure 4C:
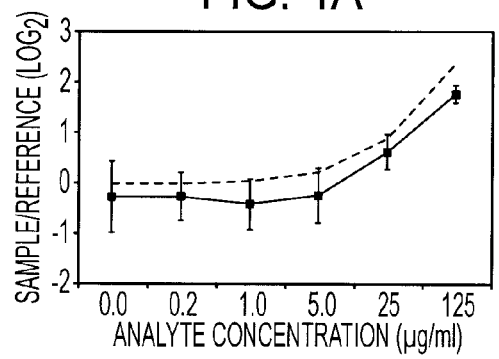
Figure 4D:
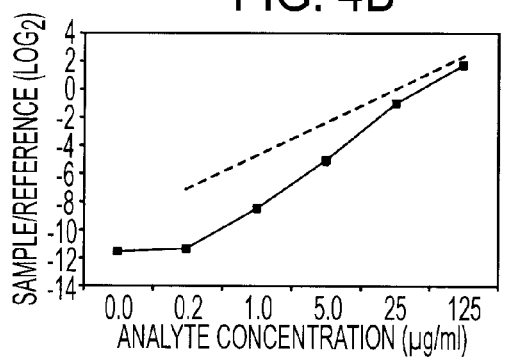
Figure 4E:
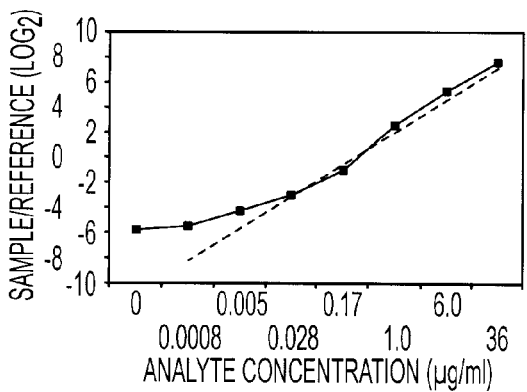
Figure 4F:
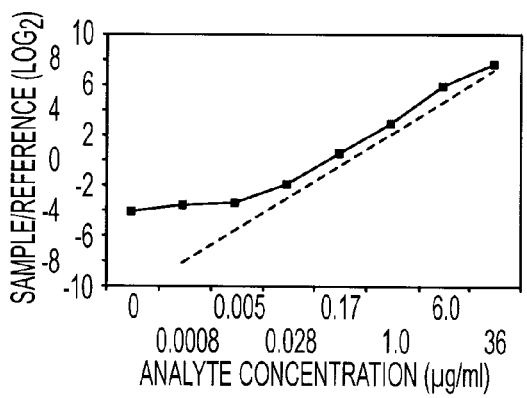
Figure 4G:
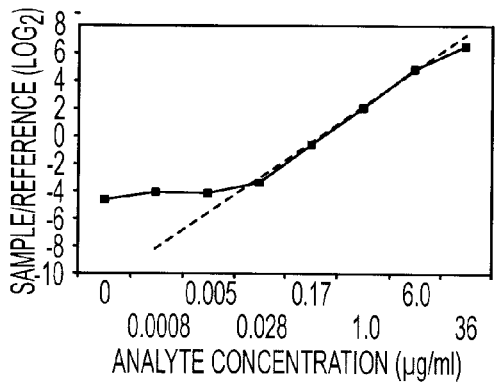
Figure 4H:
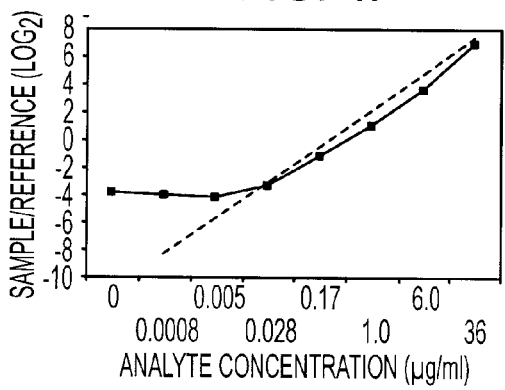

FIG. 4A-C shows antibody binding validation using analyte dilutions. The ratio ($\log_2$) of sample-specific fluorescence to reference-specific fluorescence at a given antibody was plotted with respect to the concentration of the respective analyte. FIG. 4A shows Anti-CEA measuring purified CEA spiked into human serum. FIG. 4B shows Anti-lipase measuring purified lipase spiked into human serum. FIG. 4C shows Anti-complement C3 measuring purified complement C3 spiked into human serum. FIG. 4D shows Anti-complement C3 measuring purified complement C3 spiked into a BSA solution. FIG. 4E shows Anti-CRP (ab #2) measuring recombinant CRP spiked into a BSA solution. FIG. 4F shows Anti-hemoglobin measuring purified hemoglobin spiked into a BSA solution. FIG. 4G shows Anti-IgG-Fc measuring purified IgG spiked into a BSA solution. FIG. 4H shows Anti-IgM measuring purified IgM spiked into a BSA solution. FIGS. 4A-D show the mean of duplicate experiments, and the error bars are the standard deviations between the duplicates. The dashed lines are the known ratios of sample:reference analyte concentrations. For the analytes spiked into serum (FIGS. 4A-C), the endogenous serum concentration of that analyte was estimated, and the sample:reference ratio was calculated by $(C_E+C_S)/C_E$, where $C_E$ is the endogenous concentration and $C_S$ is the spiked-in concentration of the analyte.

Each of the antibodies of FIG. 4 showed binding that varied in accordance with the changes in analyte concentrations. When analytes were spiked into serum (FIG. 4A-C), the binding response of the antibody was curved, reflecting the endogenous levels of that analyte in the serum, and when the analytes were spiked into BSA (FIG. 4D-H), the binding response was linear. Complement C3 was diluted into both serum (FIG. 4C) and BSA (FIG. 4D). Anti-cathepsin D also showed a linear reponse with analyte concentration (not shown). Anti-plasminogen only showed a response at high analyte concentrations, and anti-alpha-1-antitypsin (ab #1) did not show binding of the analyte (not shown). These studies confirm binding of the cognate analytes, but do not necessarily confirm specific binding on the microarray, especially if endogenous serum concentrations are below what was measured here. For example, CEA is normally present in the serum at concentrations around 10 ng/ml, below the range of the dilution series.

Thus the inventor positively confirmed the binding trends of seven of the nine antibodies tested by western blot and eight of the ten antibodies tested by antigen dilutions. Eight antibodies that discriminated the patient groups (anti-CA 19-9 (ab #2), anti-cathepsin D, anti-CRP (ab #2), anti-gelsolin, anti-serum amyloid A, anti-PIVKA-II, and anti-alpha-1-antitrypsin (ab #1)) were validated, and the accuracy of two others, anti-IgA and anti-transferrin, had been confirmed previously by comparisons to ELISA measurements (Hamelinck, D., Zhou, H., Li, L., Verweij, C., Dillon, D., Feng, Z., Costa, J., and Haab, B. B. Optimized normalization for antibody microarrays and application to serum-protein profiling. Mol Cell Proteomics, 2005).

An advantage of multiplexed analysis is that one may examine coordinated patterns of expression and explore algorithms for combining "weak" individual classifiers into a "powerful" combined classifier, which may increase the accuracy of sample classification. Three methods were tested for the classification: a boosting decision tree, boosting logistic regression, and logistic regression with forward selection (methods 1-3, respectively). Classifiers were made using each method to distinguish cancer from healthy, benign from healthy, and cancer from benign, using data from 77 antibodies in experiment sets three & four.

The average sensitivities, specificities and error rates from the cross validations were compared for each method (Table 4).

TABLE 4

| | Set 3 | | | | | Set 4 | | | |
|---|---|---|---|---|---|---|---|---|---|
| Method | Sensitivity | Specificity | Error | Number of Antibodies | Method | Sensitivity | Specificity | Error | Number of Antibodies |
| | Healthy vs. Cancer | | | | | Healthy vs. Cancer | | | |
| 1 | 0.813 | 0.920 | 0.139 | 25 | 1 | 0.863 | 0.895 | 0.121 | 14 |
| 2 | 0.880 | 0.895 | 0.113 | 28 | 2 | 0.950 | 0.895 | 0.074 | 20 |
| 3 | 0.900 | 0.896 | 0.102 | 10 | 3 | 0.933 | 0.938 | 0.065 | 6 |
| | Healthy vs. Benign | | | | | Healthy vs. Benign | | | |
| 1 | 0.842 | 0.890 | 0.129 | 6 | 1 | 0.717 | 0.895 | 0.178 | 14 |
| 2 | 0.808 | 0.920 | 0.127 | 13 | 2 | 0.758 | 0.940 | 0.135 | 17 |
| 3 | 0.967 | 1.000 | 0.013 | 6 | 3 | 0.970 | 0.979 | 0.025 | 8 |

TABLE 4-continued

| | Set 3 | | | | | Set 4 | | | |
|---|---|---|---|---|---|---|---|---|---|
| Method | Sensitivity | Specificity | Error | Number of Antibodies | Method | Sensitivity | Specificity | Error | Number of Antibodies |
| | Cancer vs. Benign | | | | | Cancer vs. Benign | | | |
| 1 | 0.650 | 0.600 | 0.366 | 2 | 1 | 0.543 | 0.900 | 0.332 | 1 |
| 2 | 0.883 | 0.483 | 0.258 | 4 | 2 | 0.830 | 0.483 | 0.290 | 2 |
| 3 | 0.949 | 0.800 | 0.101 | 11 | 3 | 0.916 | 0.742 | 0.145 | 8 |

The results were highly reproducible between sets three & four. All three methods were effective in distinguishing cancer from healthy and benign disease from healthy, with method 3 producing the lowest error rates in each comparison. For the distinction of cancer from benign disease, methods 1 and 2 gave about a 30% error rate, and method 3 produced about a 10% and 14% error rate in sets three and four, respectively. The relative members of antibodies used by each method were consistent between sets three & four, with method 3 using the fewest antibodies for the cancer-healthy and the benign-healthy comparisons and the most antibodies for the cancer-benign comparison.

The slight variability between sets three & four in the antibodies on the arrays may have affected the makeup of the classifiers. For example, anti-CA 19-9 (ab #2) was used only in set four, and the resulting classifiers shared only about half of the same antibodies between sets three and four (Table 1 presents the common antibodies used in sets three & four). However, the classifiers were robust to these changes, as they performed equally well in both sets. Further, the performance was not diminished when a classifier from one set was applied to the other set (not shown). The antibodies used by all three methods are likely to be the most important for the classifications (Table 5).

TABLE 5

| Cancer vs. Healthy | Benign vs. Healthy | Cancer vs. Benign |
|---|---|---|
| | Used by all methods, Set 3 | |
| anti-Amylase | anti-CRP (ab #2) | anti-PIVKA-II |
| anti-CRP (ab #2) | anti-Plasminogen | anti-Serum amyloid A |
| anti-Gelsolin | | |
| anti-Plasminogen | | |
| | Used by all methods, Set 4 | |
| anti-Alpha-1-antitrypsin (ab #2) | anti-CA19-9 (ab #2) | anti-CA19-9 (ab #2) |
| anti-CA19-9 (ab #2) | anti-CRP (ab #2) | |
| anti-CRP (ab #2) | anti-Gelsolin | |
| anti-Gelsolin | anti-M2-PK | |
| | anti-Plasminogen | |

These antibodies all appeared in Table 3 except for anti-amylase and anti-CA 19-9 (ab #2) for the benign-healthy comparison. Therefore, in general the most important antibodies for the classifiers have significant differences between the samples classes.

Figures 5A, 5B, 5C:
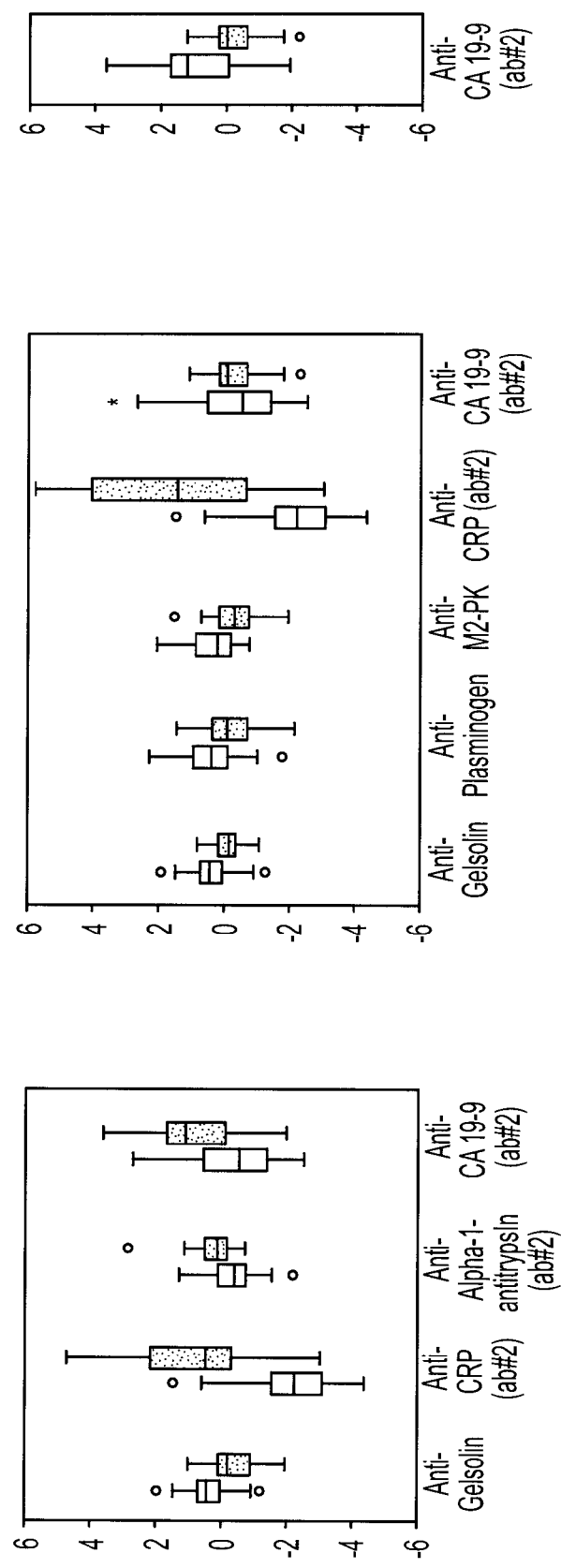
FIG. 5A-C shows distributions of measurements for antibodies contributing to the classifications.

The distributions of the measurements for the antibodies used by all three methods in set four showed the extent of the differences between the sample classes for the individual antibodies (FIG. 5). FIG. 5A-C shows distributions of measurements for antibodies contributing to the classifications. Antibodies that were used by all three classification methods are shown, using data from experiment set four. FIG. 5A shows healthy controls (light boxes) and pancreatic cancer (dark boxes). FIG. 5B shows healthy controls (light boxes) and benign disease (dark boxes). FIG. 5C shows pancreatic cancer (light boxes) and benign disease (dark boxes). The boxes give the upper and lower quartiles of the measurements with respect to the median value (horizontal line in each box). The lines give the ranges of the measurements, excluding outliers, which are represented by circles. The asterisk indicates the measurements were not statistically different ($p<0.05$) between the two classes. These distributions show that the accuracy of the distinctions between the sample classes was improved using multiple antibodies as compared to using single antibodies. For example, in the comparison of cancer to healthy, the most significant individual antibodies were anti-CRP (ab #2) and anti-CA 19-9 (ab #2), which at a fixed specificity of 90% had sensitivities of 74% and 55%, respectively, less than the values achieved using multiple antibodies (Table 4). The best individual antibody in the comparison of cancer to benign disease was CA 19-9 (ab #2) at 90% specificity and 59% sensitivity, again less than the performance of combined antibodies.

Biomarkers

Because of the low prevalence of pancreatic cancer, large collections of complete and carefully controlled samples for pancreatic cancer biomarker research are rare. By necessity the samples studied were assembled from three different sites. While the findings cannot conclusively be determined to be free from bias, analysis of the effects of age and acquisition site on the microarray profiles seemed to indicate that the observed differences between the sample classes did not arise artifactually from these sources. Further, many of the trends were consistent with previous research, as described below, lending further support to the validity of the comparisons.

The binding specificities of antibodies must be confirmed before conclusions can be made about changes in the levels of the target proteins. The inventor selected antibodies for confirmation after first screening many antibodies and identifying reproducible measurements that gave statistically valuable information. This strategy is complementary to that of first characterizing the specificities and sensitivities of all antibodies prior to running experiments. The pre-validation approach is useful when pursuing specific targets and hypotheses, but the post-validation approach is better for screening and discovery, since many antibodies may be efficiently tested.

The inventor has demonstrated two complementary methods, immunoblots and dilutions of purified antigens, to further characterize antibody performance. Immunoblots give a good picture of binding specificities in complex samples and are useful when purified antigens are not readily available, although the results may not perfectly correspond to the microarray results, since samples are denatured in the immunoblot assay and are native in the microarray assay. Denaturation may cause additional or weaker binding of some antibodies. Antigen dilutions give useful information on antibody binding characteristics, although purified antigen may not be readily available for every antibody. The antibodies tested here by that method generally showed a response that validated the binding of the intended target. In one case, with anti-alpha-1-antitrypsin (ab #1), the dilution experiment failed to produce results, but the immunoblot confirmed binding to the proper size band. The high rate of success of the inventor's validations (70-80%) may reflect the robustness of the microarray assay but also may be due to the non-random selection of the antibodies for validation. The inventor chose antibodies that showed reproducible binding patterns and changes between samples, which probably are more likely to be binding the correct target, although not necessarily exclusively. Other methods may give additional, complementary information that will be useful for further antibody characterization and validation, such as mass-spectrometry analysis of proteins bound to immunoprecipitated antibodies.

The data of the present invention are useful to evaluate the benefit of using multiple antibodies for sample classification and for identifying the antibodies that are most important in defining signatures for the sample classes. The benefit of using multiple antibodies for the classifications was shown in the improvement in the classification accuracy relative to the use of single antibodies. The low error rate in the distinction of the cancer class from the healthy class and the benign class from the healthy class reflect the major changes occurring in the blood of both types of disease. The distinction of cancer from benign disease is more difficult, as those two classes can have many similar clinical, pathological and molecular manifestations. Pancreatic cancer is often associated with pancreatitis, and the diagnosis of cancer in the presence of pancreatitis often presents a challenge for physicians. Therefore the ability to accurately diagnose the two classes using a molecular blood test is especially valuable. The classification by the logistic regression with forward selection method (method 3)—an error rate of only 10% and 14% in sets three & four, respectively—was improved over the performance of the individual antibodies and showed it may be useful to distinguish benign from malignant disease using biomarkers. The choice of which antibodies to use to distinguish malignant disease from benign cancer will be based on the results from this invention. Promising new markers include macrophage inhibitory cytokine 1 (Koopmann, J., Buckhaults, P., Brown, D. A., Zahurak, M. L., Sato, N., Fukushima, N., Sokoll, L. J., Chan, D. W., Yeo, C. J., Hruban, R. H., Breit, S. N., Kinzler, K. W., Vogelstein, B., and Goggins, M. Serum macrophage inhibitory cytokine 1 as a marker of pancreatic and other periampullary cancers. Clin Cancer Res, 10: 2386-2392, 2004) and osteopontin (Koopmann, J., Fedarko, N. S., Jain, A., Maitra, A., Iacobuzio-Donahue, C., Rahman, A., Hruban, R. H., Yeo, C. J., and Goggins, M. Evaluation of osteopontin as biomarker for pancreatic adenocarcinoma. Cancer Epidemiol Biomarkers Prev, 13: 487-491, 2004).

The validated differences observed between the samples classes included both previously-observed and newly-observed trends. CA 19-9 is a well-known pancreatic cancer marker, defined by a monoclonal antibody recognizing the sialylated Lewis$_a$ blood group antigen. Reports on the performance of CA 19-9 have varied broadly. A meta analysis of CA 19-9 serum studies found a mean sensitivity and specificity for pancreatic cancer range of 81% and 91%, respectively (Steinberg, W. The clinical utility of the CA 19-9 tumor-associated antigen. Am J Gastroenterol, 85: 350-355, 1990). The observed specificity and sensitivity for pancreatic cancer using CA 19-9 alone were lower than those observations, perhaps due to a lack of optimization of this assay for that particular analyte. Several of the observed alterations represent an acute phase response, which is typically associated with advanced pancreatic cancer (Barber, M. D., Ross, J. A., Preston, T., Shenkin, A., and Fearon, K. C. Fish oil-enriched nutritional supplement attenuates progression of the acute-phase response in weight-losing patients with advanced pancreatic cancer. J Nutr, 129: 1120-1125, 1999), and would include the elevated CRP, serum amyloid A and alpha-1-antitrypsin and the decreased transferrin levels. The elevated IgA in the serum may be due to increased secretion and leakage from the pancreatic juice, in which elevated IgA has been associated with cancer (Goodale, R. L., Condie, R. M., Dressel, T. D., Taylor, T. N., and Gajl-Peczalska, K. A study of secretory proteins, cytology and tumor site in pancreatic cancer. Ann Surg, 189: 340-344, 1979).

Cathepsin D could be involved in the cancer cell invasion process (Tedone, T., Correale, M., Barbarossa, G., Casavola, V., Paradiso, A., and Reshkin, S. J. Release of the aspartyl protease cathepsin D is associated with and facilitates human breast cancer cell invasion. Faseb J, 11: 785-792, 1997), and its level in serum previously has been associated with prostate cancer (Miyake, H., Hara, I., and Eto, H. Prediction of the extent of prostate cancer by the combined use of systematic biopsy and serum level of cathepsin D. Int J Urol, 10: 196-200, 2003); hepatocellular carcinoma (Tumminello, F. M., Leto, G., Pizzolanti, G., Candiloro, V., Crescimanno, M., Crosta, L., Flandina, C., Montalto, G., Soresi, M., Carroccio, A., Bascone, F., Ruggeri, I., Ippolito, S., and Gebbia, N. Cathepsin D, B and L circulating levels as prognostic markers of malignant progression. Anticancer Res, 16: 2315-2319, 1996); and in benign but not malignant pancreatic disease (Tumminello, F. M., Leto, G., Pizzolanti, G., Candiloro, V., Crescimanno, M., Crosta, L., Flandina, C., Montalto, G., Soresi, M., Carroccio, A., Bascone, F., Ruggeri, I., Ippolito, S., and Gebbia, N. Cathepsin D, B and L circulating levels as prognostic markers of malignant progression. Anticancer Res, 16: 2315-2319, 1996; and Leto, G., Tumminello, F. M., Pizzolanti, G., Montalto, G., Soresi, M., Carroccio, A., Ippolito, S., and Gebbia, N. Lysosomal aspartic and cysteine proteinases serum levels in patients with pancreatic cancer or pancreatitis. Pancreas, 14: 22-27, 1997), in contrast to this study. Its association with cancer was only moderate, as it did not distinguish the cancer class from the benign class.

Gelsolin in the plasma has an actin scavenging function, and its level in the serum can be reduced in response to acute tissue injury (Ito, H., Kambe, H., Kimura, Y., Nakamura, H., Hayashi, E., Kishimoto, T., Kishimoto, S., and Yamamoto, H. Depression of plasma gelsolin level during acute liver injury. Gastroenterology, 102: 1686-1692, 1992), presumably due to an increased binding and clearance of shed actin. Its altered level, which has not before been associated with pancreatic cancer or pancreatitis, may indicate a higher-than-normal amount of cell breakdown products in the blood. That observation would be consistent with the nature of fibrosis in pancreatic cancer, which is similar to a continual cell breakdown and wound healing process.

Another notable observation was the decrease in several antibodies defined by carbohydrate epitopes, such as anti-CEA, anti-CA 15-3, anti M2-PK, and anti-CA 125, seen in association with benign disease. The specificities of these measurements have not been validated, but their consistency suggests some alteration in glycoproteins associated with benign disease. These results show a wide variety of alterations in the sera of cancer patients, reflecting inflammation, immune responses, fibrosis, and perhaps altered glycosylation and glucose regulation.

PIVKA-II Biomarker

An unexpected finding was the elevation of protein-induced vitamin K antagonist II (PIVKA-II) in association with pancreatic cancer. PIVKA-II (also known as des-carboxy prothrombin or DCP) is a non-functional version of prothrombin produced by a failure of the vitamin-K-dependent addition of carboxylic acid to the gamma carbon of certain glutamic acid residues. Its blood level is elevated in association with hepatocellular carcinoma (Weitz, I. C. and Liebman, H. A. Des-gamma-carboxy (abnormal) prothrombin and hepatocellular carcinoma: a critical review. Hepatology, 18: 990-997, 1993) and in response to vitamin K deficiency (Ferland, G., Sadowski, J. A., and O'Brien, M. E. Dietary induced subclinical vitamin K deficiency in normal human subjects. J Clin Invest, 91: 1761-1768, 1993), but it was not before known to be associated with pancreatic cancer. Vitamin-K-dependent alterations have been associated with glucose tolerance (Sakamoto, N., Wakabayashi, I., and Sakamoto, K. Low vitamin K intake effects on glucose tolerance in rats. Int J Vitam Nutr Res, 69: 27-31, 1999), and the alpha cells of the pancreas have the ability to produce prothrombin (Stenberg, L. M., Nilsson, E., Ljungberg, O., Stenflo, J., and Brown, M. A. Synthesis of gamma-carboxylated polypeptides by alpha-cells of the pancreatic islets. Biochem Biophys Res Commun, 283: 454-459, 2001), so this observation could relate to alterations in glucose regulation that are commonly seen in pancreatic cancer patients.

As used by the inventor, two antibodies for detecting PIVKA-II included Anti-Protein Induced Vitamin K Antagonist made by Crystal Chem Inc., (Catalog No. 08040, Clone No. PIM-55), and Anti-PIVKA-II, made by USBio (Catalog No. P4210-50, Clone No. 8.F.228).

Figure 6:
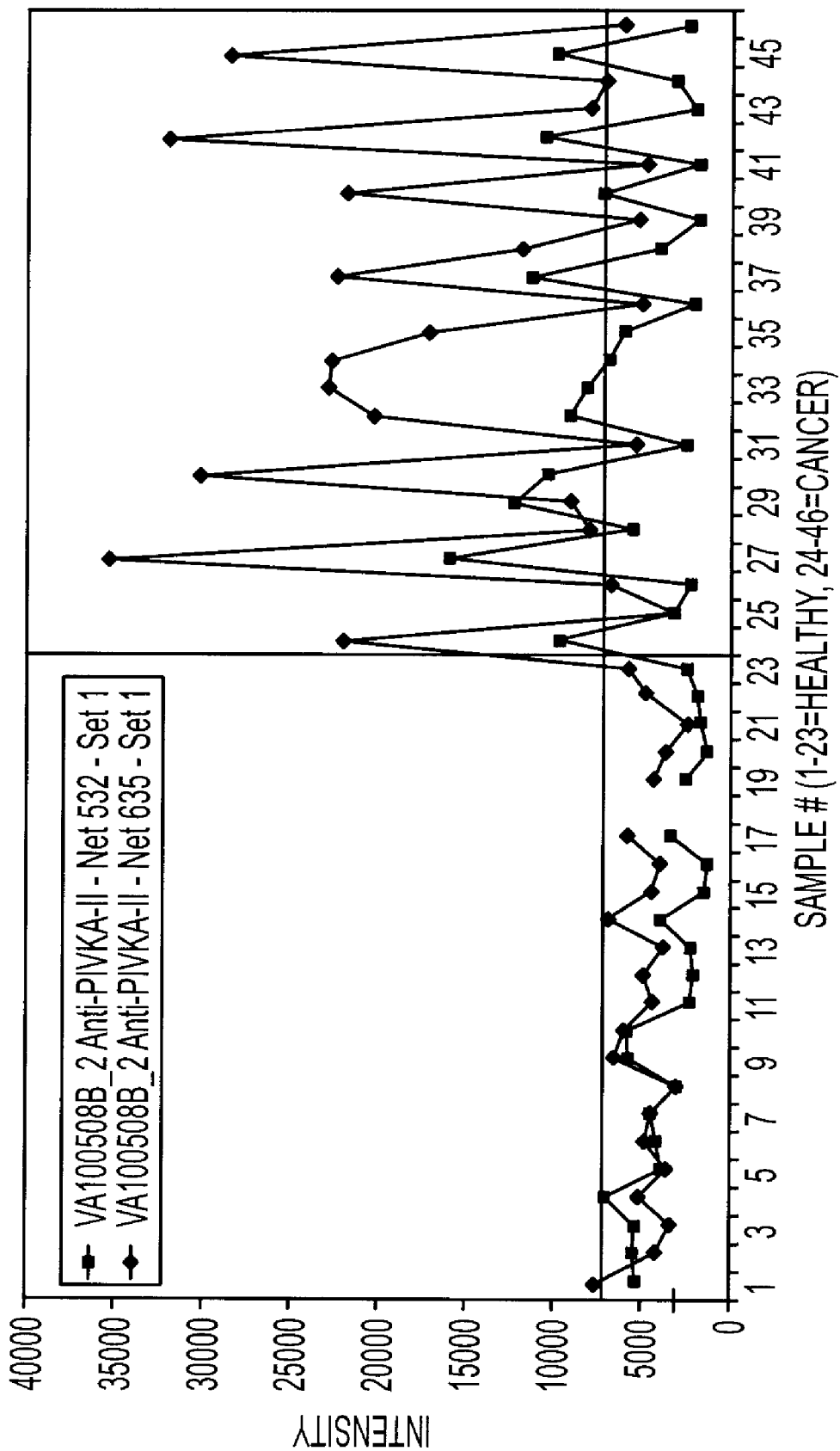
FIGS. 6 and 7 are graphs showing the results of an antibody microarray in healthy patients and patients with pancreatic cancer measured both by DCP level and level of glycosylation of DCP.
Figure 7:
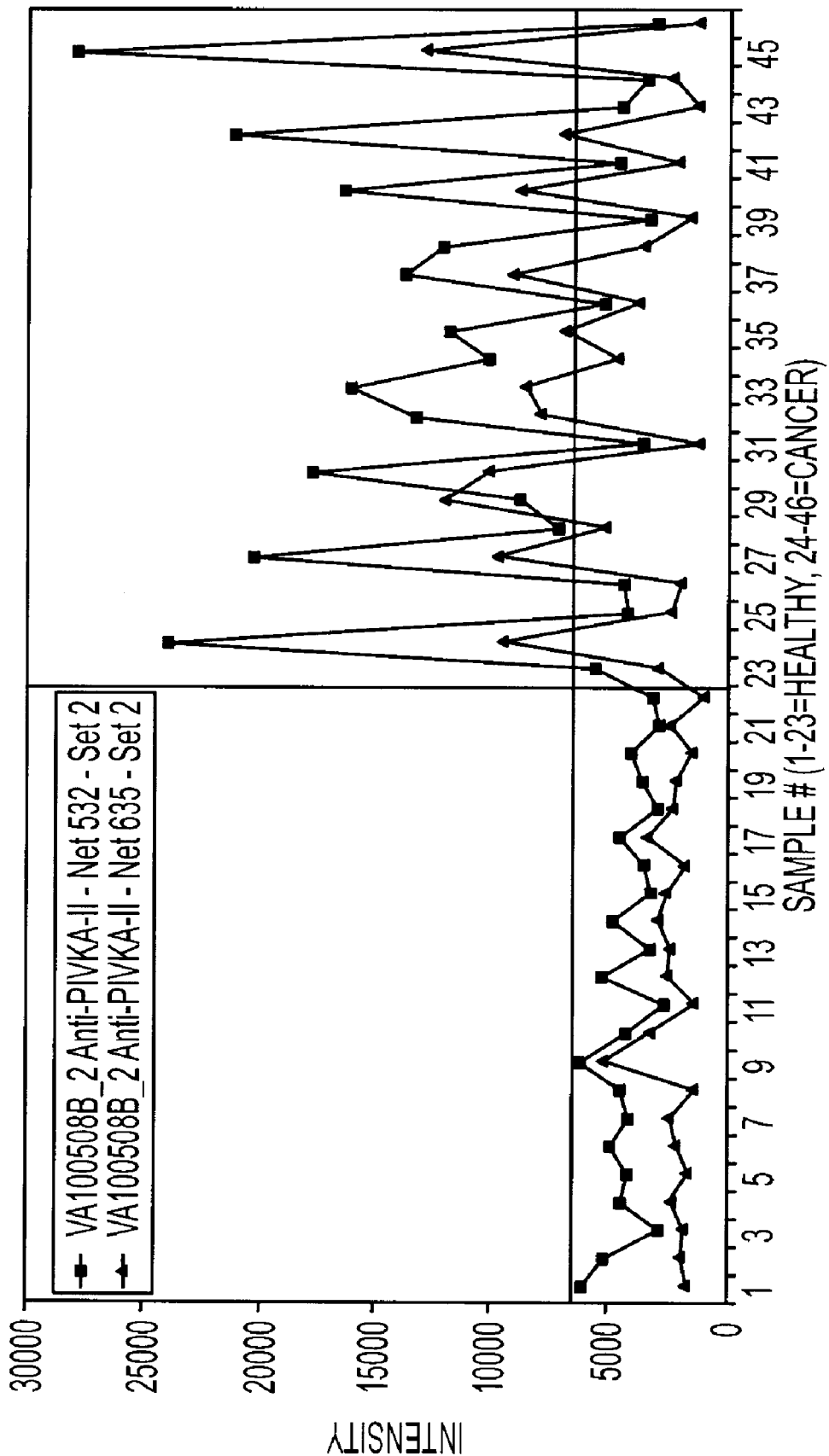

Levels of DCP in serum (or other biomarkers of the present invention) are considered to be "high" when the level exceeds a threshold of three standard deviations above the mean of the levels in a healthy control population. As shown in FIGS. 6 and 7, comparing healthy to pancreatic cancer samples, total DCP is high in pancreatic cancer compared to healthy individuals. In addition, as shown in FIGS. 6 and 7, comparing healthy individuals to cancer patients, glycosylation levels of DCP were significantly higher in cancer versus healthy (more pronounced than shown with respect to total protein).

Method for Detecting Glycosylation Levels on Multiple, Specific Proteins

Here, the inventor presents the use of labeled glycan-binding proteins for multiplexed detection of the levels of specific glycans on multiple proteins captured by antibody microarrays. The inventor also has discovered a means to efficiently and conveniently measure the levels of particular glycan structures or groups on many different specific proteins using low sample volumes. Since antibody arrays of the present invention can be performed in a high-throughput fashion, the present method has the advantage of obtaining data from large sets of samples, so that the variation in glycan levels across many samples on many proteins can be profiled. By using different glycan-binding proteins (e.g., lectins or antibodies) for detection of glycosylated proteins captured on microarrays, the variation in different glycan structures can be probed (e.g., the patterns of different glycan structures compared). The present invention is useful for determining the proteins that contain particular structures.

As discussed below, the profiling of glycan variation, using the lectins AAL and WGA, over serum samples from pancreatic cancer patients and control subjects showed multiple proteins with potential cancer-associated glycan elevations or reductions. The patterns of reactivity from the two lectins were very different from each other, indicating distinct mechanisms of regulation for those glycans. Parallel glycan-detection and sandwich assays showed that glycans reactive with the CA19-9 monoclonal antibody were elevated on the proteins carcinoembryonic antigen and MUC1 in sera from pancreatic cancer patients, which could influence the binding and fumctional properties of those proteins. As demonstrated by these data, antibody arrays with glycan detection are highly effective for profiling variation in specific glycans on multiple proteins and should be useful in diverse areas of glycobiology research.

Lectins are the preferred glycan binding proteins used in the method of the invention. Lectins include carbohydrate-binding proteins from many sources regardless of their ability to agglutinate cells. Lectins have been found in many organisms, including, plants, viruses, microorganisms and animals. Most known lectins are multimeric, with non-covalently associated subunits, and this multimeric structure gives lectins their ability to agglutinate cells or form precipitates with glycoconjugates similar to antigen-antibody interactions. A common characteristic of lectins is that they bind to specifically defined carbohydrate structures. Because of this specificity that each lectin has for a particular carbohydrate structure, even oligosaccharides with identical sugar compositions can be distinguished. Some lectins bind only structures with mannose or glucose residues, while others recognize only galactose residues. Some lectins bind only if a particular sugar is in a terminal non-reducing position in the oligosaccharide, while others bind sugars within the oligosaccharide chain. Further, some lectins do not discriminate when binding to a and b anomers, while other lectins require the correct anomeric structure and a specific sequence of sugars. Thus, the binding affinity between a lectin and its receptor may vary greatly in view of seemingly small changes in the carbohydrate structure of the receptor.

Lectins have been valuable glycan affinity reagents in experimental formats such as affinity chromatography and electrophoresis (van Dijk, W., Havenaar, E. C. & Brinkman-van der Linden, E. C. Alpha 1-acid glycoprotein (orosomucoid): pathophysiological changes in glycosylation in relation to its function. *Glycoconj J* 12, 227-33 (1995)), detection of blots of separated glycoproteins (Okuyama, N. et al. Fucosylated haptoglobin is a novel marker for pancreatic cancer: A detailed analysis of the oligosaccharide structure and a possible mechanism for fucosylation. *Int J Cancer* (2005)), and in the capture or detection of proteins in microtiter plates to quantify glycans on specific proteins (Thompson, S., Stappenbeck, R. & Turner, G. A. A multiwell lectin-binding assay using lotus tetragonolobus for measuring different glycosylated forms of haptoglobin. *Clin Chim Acta* 180, 277-84 (1989); Parker, N. et al. A new enzyme-linked lectin/mucin antibody sandwich assay (CAM 17.1/WGA) assessed in combination with CA 19-9 and peanut lectin binding assay for the diagnosis of pancreatic cancer. *Cancer* 70, 1062-8 (1992)). Antibodies also have been developed to target and study particular carbohydrates, such as the cancer-associate Thomsen-Friedenreich antigens (Kjeldsen, T. et al. Preparation and characterization of monoclonal antibodies directed to the tumor-associated O-linked sialosyl-2-6 alpha-N-acetylgalactosaminyl (sialosyl-Tn) epitope. *Cancer Res* 48, 2214-20 (1988); Santos-Silva, F. et al. Thomsen-Friedenreich antigen expression in gastric carcinomas is associated with MUC1 mucin VNTR polymorphism. *Glycobiology* 15, 511-7 (2005)) or the Lewis blood group structures (Lucka, L. et al. Identification of Lewis x structures of the cell adhesion molecule CEACAM1 from human granulocytes. *Glycobiology* 15, 87-100 (2005)). Cancer-associated glycosylation has been identified using lectins on proteins such as alpha-fetoprotein (Aoyagi, Y. et al. The fucosylation index of serum alpha-fetoprotein as useful prognostic factor in patients with hepatocellular carcinoma in special reference to chronological changes. *Hepatol Res* 23, 287 (2002); Shimizu, K. et al. Comparison of carbohydrate structures of serum alpha-fetoprotein by sequential glycosidase digestion and lectin affinity electrophoresis. *Clin Chim Acta* 254, 23-40 (1996)), haptoglobin (Okuyama, N. et al. Fucosylated haptoglobin is a novel marker for pancreatic cancer: A detailed analysis of the oligosaccharide structure and a possible mechanism for fucosylation. *Int J Cancer* (2005); Thompson, S., Cantwell, B. M., Cornell, C. & Turner, G. A. Abnormally-fucosylated haptoglobin: a cancer marker for tumour burden but not gross liver metastasis. *Br J Cancer* 64, 386-90 (1991)), alpha-1-acid glycoprotein (van Dijk, W., Havenaar, E. C. & Brinkman-van der Linden, E. C. Alpha 1-acid glycoprotein (orosomucoid): pathophysiological changes in glycosylation in relation to its function. *Glycoconj J* 12, 227-33 (1995)), and alpha-1-antitrypsin (Thompson, S., Guthrie, D. & Turner, G. A. Fucosylated forms of alpha-1-antitrypsin that predict unresponsiveness to chemotherapy in ovarian cancer. *Br J Cancer* 58, 589-93 (1988)). Lectin-affinity and immuno-affinity electrophoresis and blotting methods were used to isolate particular proteins and quantify specific glycan groups on those proteins.

Figure 10A:
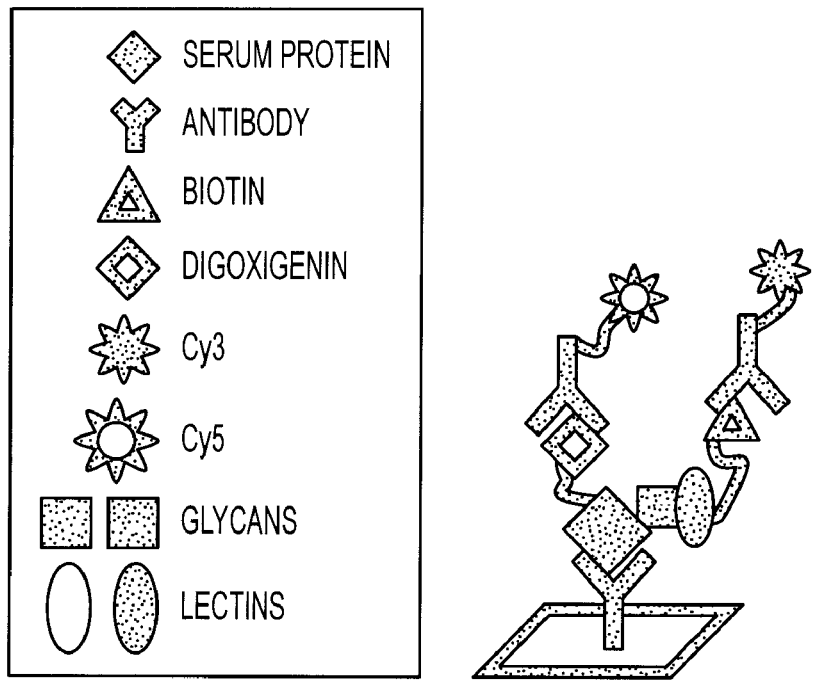
FIGS. 10A-B are schematic drawings depicting two methods of measuring glycan groups on specific proteins.
Figure 10B:
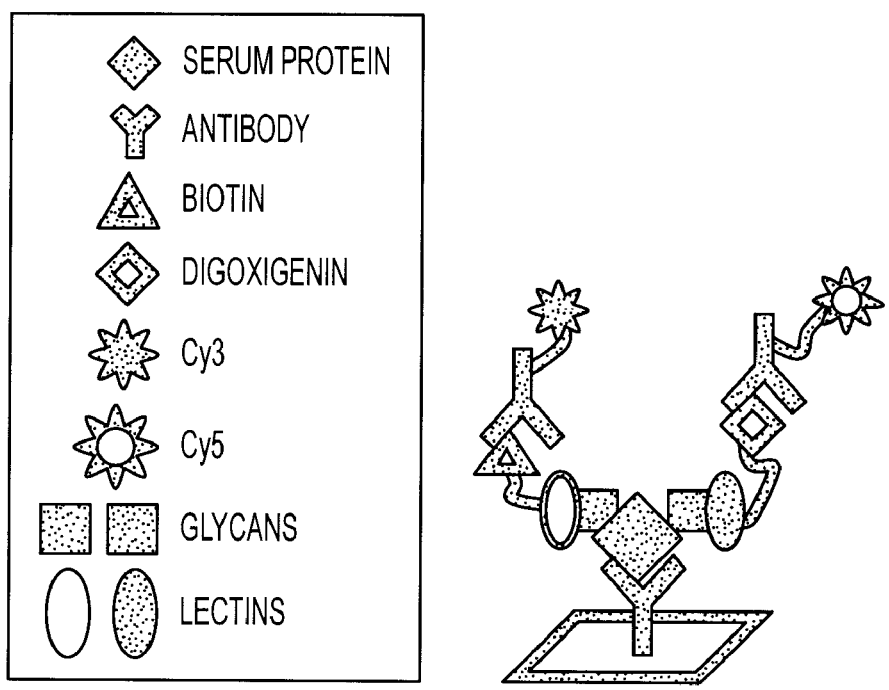

The inventor identifies two preferred embodiments of this invention: a one-color method for measuring glycan only, and a two-color method for measuring both glycan and protein levels. FIGS. 10A and 10B schematically depict the two formats. FIG. 10A shows lectin binding on labeled proteins, detected in two colors. FIG. 10B shows two lectins binding two different glycans, detected in two colors. Both methods use antibody microarrays. In the first method, the proteins from a biological sample, such as serum or tissue extracts, are labeled with a tag such as biotin or digoxigenin and incubated on an antibody microarray. Proteins that are recognized by an antibody on the array are captured by that antibody (i.e., proteins known as "serum" proteins). After washing off unbound proteins, a glycan-binding-protein (GBP) is incubated on the array. A GBP is a molecule that recognizes specific glycans. Examples are lectins or antibodies raised against particular glycan groups. The GBP is labeled with a tag that is different from the one used to label the proteins captured by the antibodies on the microarray. The GBP will bind to glycan groups on the proteins that are captured by the antibody microarray, in proportion to the amount of the glycan present. After unbound GBP is washed off, the tags on the bound proteins and bound GBPs are detected using technology such as two-color rolling circle amplification or resonance-light scattering. The relative signal from the GBP and captured proteins reflects the amount of glycan per protein. Other tags and methods of tag detection are known in the art and can be applied to the present invention.

In another preferred embodiment of the invention, an unlabelled biological sample (e.g., serum) is incubated on an antibody microarray, and the proteins are captured by the immobilized antibodies according to their specificities. After unbound proteins are washed off, two different GBPs are incubated on the array, each targeting a different glycan and each labeled with a different tag from the other (e.g., biotin and digoxigenin). Unbound GBPs are washed off, and the tags are detected as described in the first embodiment. The relative signal from the two tags reflects the relative signal of the two glycan groups on each protein and additional modification of the present invention could include the detection of more than two different tags on the microarray. With the ability to detect more than two tags (e.g., using three-color or four-color detection) additional GBPs, each labeled with a different tag, could be used in the same experiment.

Using the present invention, glycans on multiple proteins can be measured in one experiment, using low sample volumes, so that efficient screening and profiling of changes in glycosylation is possible. Samples can be run in high throughput, which is important for biomarker research. Also, the experiments are highly reproducible, another critical factor in characterizing clinical samples. All of these advantages will be valuable for biological and diagnostics research. Further, the present invention could be used as a tool for research on specific glycans on certain proteins. The components required also could be assembled in a kit. If a specific glycosylation alteration associated with a disease is discovered that is useful for diagnostics, the present invention could be used as a clinical assay, also preferably in a kit. Preferably, the methods of the present invention are useful as applied to the study of changes in glycosylation on specific serum proteins in relation to cancer.

In addition, the inventor measured both glycan and protein levels using parallel arrays detected either with lectins or with sandwich detection antibodies. The parallel detection of both glycan and protein was important to observe the relationships between those two levels. The ability to efficiently process many samples led to the identification of several potential cancer-related glycan and protein alterations. High-throughput sample processing also allowed the comparisons of profiles from different lectins and the observation of differential regulation of different glycan structures.

Figure 12A:
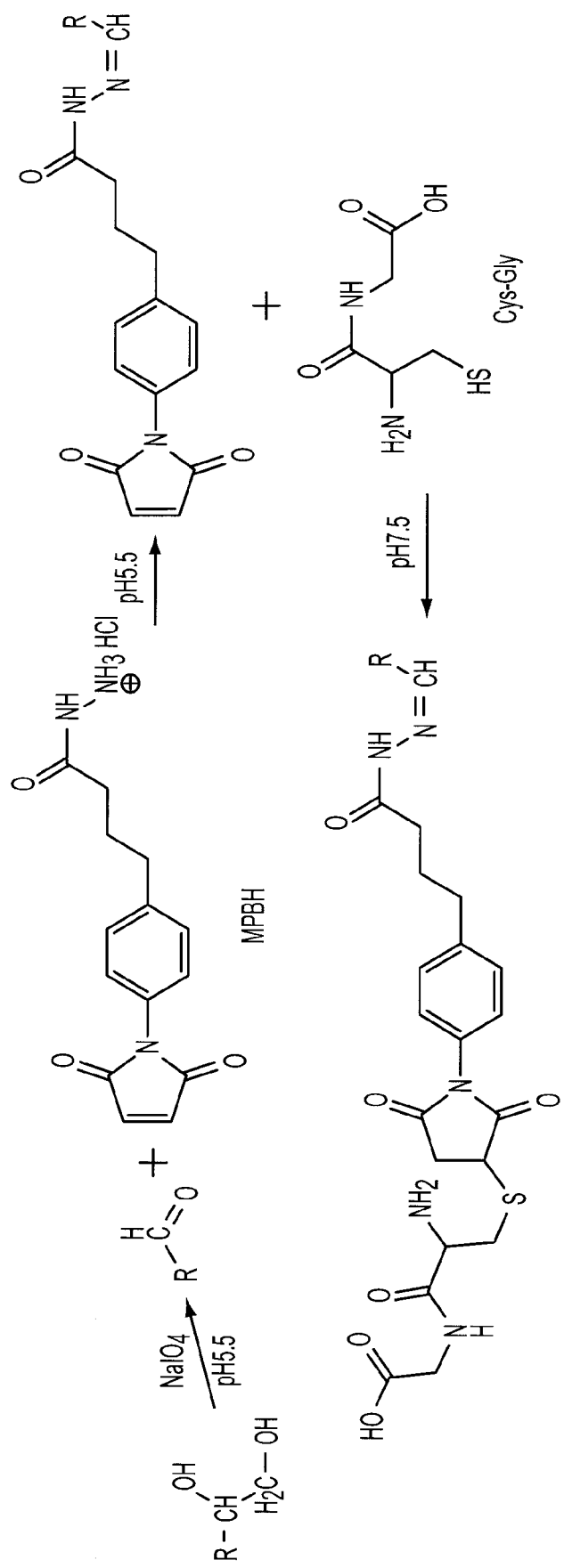
FIGS. 12A-D show blocking non-specific GBP binding to capture antibodies.
Figure 12B:
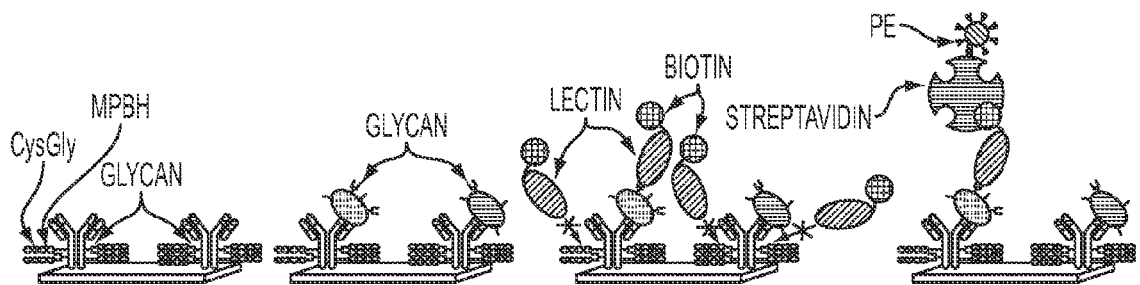

Since antibodies have carbohydrate groups, it occasionally happens that a given GBP will bind to the glycan group on the captured antibody on the microarray, rather than bind to the glycan on the captured protein. This effect would limit the ability to detect glycan changes using certain antibody-lectin combinations. To allow the use of any antibody-lectin pair, the inventor developed a method to block GBP binding to glycan groups on the spotted antibodies. The method employs oxidation (e.g., with NaIO4) of the carbohydrate groups on the spotted antibodies followed by derivatization with a hydrazide-maleimide biflnctional crosslinking reagent, followed by attachment of a cysteine-glycine dipeptide to the maleimide group (FIG. 12A). The oxidation opens saccharide rings at cis-alcohol positions. One of the alcohols is oxidized to an aldehyde group. It is with that group that the hydrazide reacts. All antibody carbohydrate chains contain saccharide groups with cis-alcohols. The Cys-Gly dipeptide adds bulk to the derivatization of the carbohydrates to prevent recognition by lectins (FIG. 12B). With the present method, GBP binding to the antibodies may be almost completely abolished by the conjugation of the antibody-associated carbohydrate groups with the di-peptide. With this step, glycans on the captured proteins will be detected rather than the glycans on the spotted capture antibodies.

In a preferred method, the antibodies are first spotted on the array, followed by the blocking steps. Alternatively, however, the antibodies to be spotted could be blocked while in solution, i.e., before the antibodies are spotted on the microarray. This alternate blocking procedure may be useful to pretreat the glycan-detection reagents in case it is desirable to detect more than one glycan in a single assay, using multiple lectins. Since lectins are glycoproteins, they may react with each other when they are used together. Blocking the glycan groups on the lectins would prevent those interactions.

Glycosylation alterations were found on the proteins haptoglobin, alpha-2-macroglobulin, MUC1, and CEA. Elevated fucosylation on haptoglobin previously has been observed in pancreatic cancer (Okuyama, N. et al. Fucosylated haptoglobin is a novel marker for pancreatic cancer: A detailed analysis of the oligosaccharide structure and a possible mechanism for fucosylation. *Int J Cancer* (2005)) and in diseases such as inflammatory joint disease (Thompson, S., Kelly, C. A., Griffiths, I. D. & Turner, G. A. Abnormally-fucosylated serum haptoglobins in patients with inflammatory joint disease. *Clin Chim Acta* 184, 251-8 (1989)), ovarian cancer (Thompson, S., Dargan, E. & Turner, G. A. Increased fucosylation and other carbohydrate changes in haptoglobin in ovarian cancer. *Cancer Lett* 66, 43-8 (1992)), and hepatocellular carcinoma (Naitoh, A., Aoyagi, Y. & Asakura, H. Highly enhanced fucosylation of serum glycoproteins in patients with hepatocellular carcinoma. *J Gastroenterol Hepatol* 14, 436-45 (1999)). Reduced fucosylation on alpha-2-macroglobulin was not before observed. Glycan alterations on MUC1 in cancer have been observed previously, including truncations in O-glycosylation that lead to the exposure of core carbohydrate structures such as the Thomsen-Friedenreich and sialyl Tn antigens (Reis, C. A., David, L., Seixas, M., Burchell, J. & Sobrinho-Simoes, M. Expression of fully and under-glycosylated forms of MUC1 mucin in gastric carcinoma. *Int J Cancer* 79, 402-10 (1998); Lloyd, K. O., Burchell, J., Kudryashov, V., Yin, B. W. & Taylor-Papadimitriou, J. Comparison of O-linked carbohydrate chains in MUC-1 mucin from normal breast epithelial cell lines and breast carcinoma cell lines. Demonstration of simpler and fewer glycan chains in tumor cells. *J Biol Chem* 271, 33325-34 (1996)). It was previously shown that biliary and pancreatic mucins carry the sialyl-Lewis$^x$ and sialyl-Lewis$^a$ (the CA19-9 epitope) structures (Ho, J. J., Siddiki, B. & Kim, Y. S. Association of sialyl-Lewis (a) and sialyl-Lewis(x) with MUC-1 apomucin in a pancreatic cancer cell line. *Cancer Res* 55, 3659-63 (1995); Kalthoff, H., Kreiker, C., Schmiegel, W. H., Greten, H. & Thiele, H. G. Characterization of CA 19-9 bearing mucins as physiological exocrine pancreatic secretion products. *Cancer Res* 46, 3605-7 (1986); von Ritter, C. et al. Biliary mucin secreted by cultured human gallbladder epithelial cells carries the epitope of CA 19-9. *Anticancer Res* 17, 2931-4 (1997)). This study provided fresh evidence that the CA 19-9 reactive structure is actually increased on MUC1 in cancer. CEA family members have been shown to carry Lewis$^x$ structures (Lucka, L. et al. Identification of Lewis x structures of the cell adhesion molecule CEACAM1 from human granulocytes. *Glycobiology* 15, 87-100 (2005); Stocks, S. C., Albrechtsen, M. & Kerr, M. A. Expression of the CD15 differentiation antigen (3-fucosyl-N-acetyl-lactosamine, LeX) on putative neutrophil adhesion molecules CR3 and NCA-160. *Biochem J* 268, 275-80 (1990); Stocks, S. C. & Kerr, M. A. Neutrophil NCA-160 (CD66) is the major protein carrier of selectin binding carbohydrate groups LewisX and sialyl lewisX. *Biochem Biophys Res Commun* 195, 478-83 (1993)), but cancer-associated elevations of the CA19-9-reactive structure were not demonstrated. Other proteins from the study may have elevated glycan levels in cancer, and further experiments will be required to characterize the relationships between protein and glycan levels. Further studies also could address the functional consequence of the observed glycan alterations. Lewis blood group structures are ligands that mediate binding to endothelial cells through E-selectin and endothelial leucocyte adhesion molecule 1 (ELAM-1), so a possible role of the CA 19-9-reactive elevations may be to modulate interactions with receptors or circulating proteins.

A glycan alteration in a protein in a diseased patient (e.g., a cancer patient) serum sample is present at a higher or lower level (i.e., at a different level) than in the protein in a healthy patient serum sample when the level of glycosylation of the particular protein in the diseased patient exceeds a threshold of one and one-half standard deviations above the mean of the concentration as compared to the healthy patient. More preferably, a glycan alteration in a protein in a diseased patient (e.g., a cancer patient) serum sample is present at a higher or lower level (i.e., at a different level) than in the protein in a healthy patient serum sample when the level of glycosylation of the particular protein in the diseased patient exceeds a threshold of two standard deviations above the mean of the concentration as compared to the healthy patient. Most preferably, a glycan alteration in a protein in a diseased patient (e.g., a cancer patient) serum sample is present at a higher or lower level (i.e., at a different level) than in the protein in a healthy patient serum sample when the level of glycosylation of the particular protein in the diseased patient exceeds a threshold of three standard deviations above the mean of the concentration as compared to the healthy patient. New markers could be discovered using this method to probe many different cancer-associated glycans and proteins, and the combined data from several different glycan measurements could form specific glycan profiles that are altered in cancer.

In some cases the data from these types of experiments could be affected by the existence of protein-protein complexes in the captured proteins, so that the GBPs detect glycans on proteins that are in complex with the captured proteins, rather than on the primary target of the capture antibody. That effect could be circumvented by first treating the sample to denature or digest proteins, or glycan alterations could be studied further using gel electrophoresis and blotting methods (as shown in FIG. 14). Blotting methods could be useful to follow up on particular proteins and glycans identified using the present inventions.

This novel method could be used for a variety of applications, such as to develop novel biomarkers, to characterize the glycans that are present of various proteins, or to investigate the coordinated regulation of different glycan structures. The value of the experiments will be enhanced by the better characterization of the specificities of the lectins and the development of new antibodies against cancer-associated glycotopes. Glycan microarrays could be a useful complementary method for that purpose (Blixt, O. et al. Printed covalent glycan array for ligand profiling of diverse glycan binding proteins. *Proc Natl Acad Sci USA* 101, 17033-17038 (2004); Manimala, J. C., Li, Z., Jain, A., VedBrat, S. & Gildersleeve, J. C. Carbohydrate array analysis of anti-Tn antibodies and lectins reveals unexpected specificities: implications for diagnostic and vaccine development. *Chembiochem* 6, 2229-41 (2005)). The use of highly-specific and well-characterized lectins and glycan-binding antibodies, combined with high-throughput sample processing methods, should lead to a better characterization of the variation of carbohydrate structures in health and disease.

EXAMPLES

The present invention is more particularly described in the following examples, which are intended as illustrative only, since modifications and variations therein will be apparent to those skilled in the art.

Example 1

Serum Samples

Serum samples were assembled from three sites. At Evanston Northwestern Healthcare (ENH, Evanston, Ill.), serum samples were collected from patients with pancreatic adenocarcinoma (stage I to stage IV), other gastro-intestinal malignancies (such as colon cancer, duodenal or esophageal cancer), or benign gastro-intestinal diseases (such as ampullary adenoma, pancreatitis, cystadenoma, pseudocyst or diverticulosis). The samples were collected prior to any invasive procedures, and the patient diagnoses were confirmed after subsequent procedures. Control samples also were collected at ENH from high-risk individuals from pancreatic cancer prone families undergoing surveillance with Endoscopic Ultrasound (EUS) or Endoscopic Retrograde Cholangiopancreatography (ERCP). The control subjects had no pancreatic lesions, and serum samples were collected using the same procedure as for the other patients at ENH. Additional samples from pancreatic cancer patients and healthy control subjects were collected in western Michigan (WM) and at the University of Michigan (UM) hospitals, respectively. The samples from WM were collected from seven different hospitals as part of a phase II clinical trial evaluating combination chemotherapeutic agents for the treatment of locally advanced or metastatic pancreatic adenocarcinoma (stage III or higher). Some of the patients had prior surgical or radiation treatment of the primary tumor, but not within four weeks of sample collection, and only after fully recovering from the effects of the treatment. No patients had prior systemic chemotherapeutic treatment. The control samples from UM were collected as part of a liver cancer biomarker study. The subjects were seen by their primary care doctor for their routine annual physical and were healthy with no symptoms of gastro-intestinal disease. The WM samples were sent on ice to the Van Andel Research Institute (VARI), where they were divided into aliquots and frozen at −80° C. within 12 hours of drawing. The other samples were stored at each site at −80° C. and were sent frozen on dry ice to the VARI, where they were stored at −80° C. Each aliquot had been thawed no more than two times prior to use. All samples were coded to protect patient anonymity and were collected under protocols approved by local Institutional Review Boards for human subjects research.

In experiment sets one & two, 32 samples from patients with pancreatic adenocarcinoma, 18 samples from patients with benign gastro-intestinal diseases, 22 samples from patients with other gastro-intestinal malignancies, and 33 healthy controls were used. In experiment sets three & four, 61 samples from patients with pancreatic adenocarcinoma, 31 samples from patients with benign diseases, and 50 healthy controls were used. Seventy-five of the samples were common between sets one & two and sets three & four. Table 1 presents a summary of the sources and associated demographic information of the samples used in sets three & four. The number of samples in each class, the median ages (standard deviation in parenthesis), and percent male are shown in Table 6.

TABLE 6

| Class | Number | Age | % Male |
|---|---|---|---|
| Healthy | 50 | 43.0 (13.0) | 33.3 |
| UM | 33 | 39.4 (12.1) | 21.2 |
| ENH | 17 | 49.4 (11.6) | 58.8 |
| Pancreatic cancer | 61 | 66.7 (11.9) | 50.8 |
| ENH | 39 | 71.4 (9.4) | 51.3 |
| WM | 22 | 58.2 (10.7) | 50.0 |
| Benign disease | 31 | 56.5 (16.8) | 50.9 |

Example 2

Antibodies and ELISA

Antibodies were purchased from various sources. Table 1 shows the complete list of antibodies used, and performance characteristics. The average CVs, correlations, and average S/Bs (543 channel only) were calculated. The "correlation overlap" column refers to the number of samples that both gave measurable data in both sets one and two (out of 89 possible) or in both sets three and four (out of 138 possible). The "Control S/B/" column gives the average S/B of each antibody in the negative control experiments, in which unlabeled sera were incubated on the arrays.

Antibodies that were supplied in ascites fluid, culture supernatant or antisera were purified using Protein A beads (Affi-gel Protein A MAPS kit, Bio-Rad) according to the manufacturer's protocol. The antibodies were prepared at concentrations of 200-2000 μg/ml (most at 500 μg/ml) in 10.1 mM Na2HPO4, 1.8 mM KH2PO4, 137 mM NaCl, 2.7 mM KCl, pH 7.5 (1×PBS) containing 0.02% NaN3. The integrity of each antibody preparation was examined by reducing and non-reducing gel electrophoresis. Nine of the antibodies that had been printed did not show bands at the sizes expected for IgG and were removed from the analyses. Enzyme-linked immunosorbent assays (ELISA) were performed using commercially available kits from Bethyl Corporation (Montgomery, Tex.) for the detection of hemoglobin and IgM.

Example 3

Fabrication Of Antibody Microarray

Microarrays were prepared as previously described by the inventor. Zhou, H., Bouwman, K., Schotanus, M., Verweij, C., Marrero, J. A., Dillon, D., Costa, J., Lizardi, P. M., and Haab, B. B. Two-color, rolling-circle amplification on antibody microarrays for sensitive, multiplexed serum-protein measurements. Genome Biology, 5: R28, 2004. The antibody solutions were assembled in polypropylene 384-well microtiter plates (MJ Research), using 20 μl in each well. A piezoelectric non-contact printer (Biochip Arrayer, PerkinElmer Life Sciences) spotted approximately 350 pl of each antibody solution on the surfaces of either hydrogel-coated (OptArray slides, Accelr8 Technology Corp.) or ultra-thin-nitrocellulose-coated microscope slides (PATH slides, GenTel Biosurfaces). Twelve identical arrays were printed on each slide, with each array consisting of 88-90 antibodies and control proteins spotted in triplicate in an 18×15 array. The printed hydrogel slides were rinsed three times in 1×PBS containing 0.5% Tween-20 (PBST0.5), placed in pH 8.0 50 mM phosphate buffer with 50 mM glycine to quench unreacted surface N-hydroxysuccinimide groups, and rinsed three more times in PBST0.5. The slides were assembled in a ProPlate multiarray slide module (Grace Bio-Labs) to define separate wells for each array on each slide. The printed PATH slides were imprinted with a wax border around each of the arrays to define hydrophobic boundaries, using a custom-built device. The slides were rinsed briefly in PBST0.5, blocked for one hour at room temperature in PBST0.5 containing 1% BSA and 0.3% CHAPS, and rinsed two more times with PBST0.5. Slides were dried by centrifugation at 150×g for 1 minute prior to sample application.

Example 4

Sample Labeling

The detection strategy was based two-color comparative fluorescence, as shown previously. Miller, J. C., Zhou, H., Kwekel, J., Cavallo, R., Burke, J., Butler, E. B., Teh, B. S., and Haab, B. B. Antibody microarray profiling of human prostate cancer sera: antibody screening and identification of potential biomarkers. Proteomics, 3: 56-63, 2003; Haab, B. B., Dunham, M. J., and Brown, P. O. Protein microarrays for highly parallel detection and quantitation of specific proteins and antibodies in complex solutions. Genome Biology, 2: 1-13, 2001. An aliquot from each of the serum samples was labeled with N-hydroxysuccinimide-biotin (NHS-biotin, Pierce), and another aliquot was labeled with N-hydroxysuccinimide-digoxigenin (NHS-DIG, Molecular Probes). Each 1 µl serum aliquot was diluted with 9 µl of a buffer consisting of 16.8 mM $Na_2HPO_4$, 3 mM $KH_2PO_4$, 230 mM NaCl, 4.5 mM KCl, pH 7.5 (1.7×PBS) which contained protease inhibitors (Complete Mini protease inhibitor cocktail tablet, Roche), at a dilution of 1 tablet in 5 ml of buffer. In experiments one & two the buffer also contained 4.4 µg/ml BSA labeled with 2,4-dinitrophenol (DNP) and 4.4 µg/ml of N-terminal FLAG-bacterial alkaline phosphatase fusion protein (Sigma), as normalization controls. The diluted serum was incubated for one hour on ice after the addition of 5 µl of 1.5 mM NHS-biotin or NHS-DIG in 15% DMSO. The reactions were quenched by the addition of 5 µl of 1 M Tris-HCl, pH 7.5 and incubated on ice for another 20 minutes. The remaining unreacted dye was removed by passing each sample mix through a size-exclusion chromatography spin column (Bio-Spin P6, Biorad) under centrifugation at 1000×g for two minutes. The spin columns had been pre-washed three times with 500 µl of 50 mM Tris, 150 mM NaCl, pH 7.5 (1×TBS) containing protease inhibitors. The DIG-labeled samples were combined to form a reference pool, and equal amounts (typically 15 µl) of the pool were transferred to each of the biotin-labeled samples. Each sample-reference mixture was brought to a final volume of 40 µl by the addition of 6 µl of 1×TBS and 4 µl of 1×TBS containing Super Block (Pierce, prepared according to manufacturer's instructions), 1.0% Brij-35, and 1.0% Tween-20.

Example 5

Processing Of Antibody Microarrays

Forty microliters of each labeled serum sample mix was incubated on a microarray with gentle rocking at room temperature for one hour. The slides were rinsed in 1×PBS with 0.1% Tween-20 (PBST0.1) to remove the unbound sample and subsequently washed three times for three minutes each in PBST0.1 at ambient temperature with gentle rocking. The slides were dried by centrifugation at 150×g for 1 minute (nitrocellulose slides) or by aspiration (hydrogel slides). The biotin- and digoxigenin-labeled bound proteins were detected by Two-Color, Rolling-Circle Amplification (TC-RCA) as described previously (Zhou, H., Bouwman, K., Schotanus, M., Verweij, C., Marrero, J. A., Dillon, D., Costa, J., Lizardi, P. M., and Haab, B. B. Two-color, rolling-circle amplification on antibody microarrays for sensitive, multiplexed serum-protein measurements. Genome Biology, 5: R28, 2004), with minor modifications. The microarrays were incubated for one hour at ambient temperature with 40 µl of a solution containing 75 nM Circle 1, 75 nM Circle 4.2, 1.0 µg/ml Primer 1-conjugated anti-Biotin, and 1.0 µg/ml Primer 4.2-conjugated anti-DIG in PBST0.1 with 1 mM EDTA and 5 mg/ml BSA. The microarrays were washed and dried as described above. Microarrays were then incubated with 40 µl of 1× Tango buffer (Fermentas, Hanover, MD) containing 0.36 units of phi29 DNA polymerase (New England Biolabs), 0.1% Tween-20 and 400 µM dNTPs for 30 minutes at 37° C. The microarrays were washed in 2×SSC (300 mM NaCl and 30 mM sodium citrate, dihydrate) with 0.1% Tween-20 (SSCT) as described above and dried. Cy3-labeled Decorator 1 and Cy5-labeled Decorator 4.2 were prepared at 0.1 µM each in SSCT and 0.5 mg/ml herring sperm DNA. Forty microliters of this solution was incubated on the microarrays for one hour at 37° C. The microarrays were washed in SSCT and dried as described above. Peak fluorescence emission was detected at 570 nm and 670 nm using a microarray scanner (ScanArray Express HT, PerkinElmer Life Sciences).

Example 6

Primary Data Analysis

The inventor used the software program GenePix Pro 5.0 (Axon Instruments) to quantify the image data. An intensity threshold for each antibody spot was calculated by the formula $3*B*CV_b$, where B is each spot's median local background, and $CV_b$ is the average coefficient of variation (standard deviation divided by the average) of all the local backgrounds on the array. Spots that either did not surpass the intensity threshold in both color channels, had a regression coefficient (calculated between the pixels of the two color channels) of less than 0.3, or had more than 50% of the pixels saturated in either color channel were excluded from analysis. The ratio of background-subtracted, median sample-specific fluorescence to background-subtracted, median reference-specific fluorescence was calculated, and the ratios from replicate antibody measurements within the same array were averaged using the geometric mean (log transformed prior to averaging). Normalization was applied to each array. The ratios from each array (averaged over the replicate spots) were multiplied by a normalization factor N for each array that was calculated by $N=(S_p/\mu_p)/A$, where $S_p$ is the protein concentration of the serum sample on that array, $\mu_p$ is the mean protein concentration of all the samples, and A is the array ratio average for that array. The array ratio average for each array was generated by taking the geometric mean of all the antibody ratios on that array. Serum protein concentrations were determined using a protein assay kit (BCA, Pierce) according to the manufacturers instructions, and two independent measurements were averaged for each sample. This normalization method, based on the premise that average protein binding to each array is proportional to the total protein concentration in the sample, was validated using previously-demonstrated methods. Hamelinck, D., Zhou, H., Li, L., Verweij, C., Dillon, D., Feng, Z., Costa, J., and Haab, B. B. Optimized normalization for antibody microarrays and application to serum-protein profiling. Mol Cell Proteomics, 2005.

Example 7

Immunoblotting

50 µg of serum protein in 20 µl of 1× non-reducing Laemmli sample buffer was loaded per lane onto pre-cast polyacrylamide gels (Criterion, Bio-Rad). The percentage acrylamide of the gel varied based on the known molecular weight of the protein that was to be probed. The serum samples were selected based on the data from the microarray experiments. For each protein to be probed, two serum samples were chosen that showed high binding to the respective antibody, and two serum samples were chosen that showed low binding to the respective antibody. Following electrophoresis, the separated proteins were transferred to 0.2 µm nitrocellulose. The nitrocellulose was rinsed briefly with PBST0.1 and then blocked overnight at 4° C. in PBST0.1 containing 2% ECL Advance blocking agent (Amersham). The nitrocellulose was washed two times, 5 minutes each, with PBST0.1 and incubated with 10 µg/ml biotinylated primary antibody in PBST0.1 containing 2% ECL Advance blocking agent blocking buffer for 60 minutes at ambient temperature while shaking. The primary antibodies had been labeled with NHS-biotin (Molecular Probes) according to the manufacturer's instructions. The nitrocellulose was washed three times, 5 minutes each, with PBST0.1 and incubated for 60 minutes with a $1:10^5$ dilution of peroxidase-conjugated streptavidin (Amersham) in blocking buffer. The blot was washed 5 times, 10 minutes each, with PBST0.1 and developed with the ECL Advance Western Blotting Detection Kit (Amersham) according to the manufacturers instructions. The developed blot was exposed to Hyperfilm (Amersham) for 10-60 seconds.

Example 8

Protein Dilution Series Analysis

The following protein standards were used: Purified IgG and IgM from Jackson Immunoresearch; purified complement C3 and cathepsin D and recombinant C-reactive protein (CRP) from Calbiochem; purified hemoglobin from Sigma; purified lipase, plasminogen and carcinoembryonic antigen (CEA) from Fitzgerald Industries; and purified alpha-1-antitrypsin from Research Diagnostics. For the proteins CEA, lipase, complement C3 and plasminogen, 5 µl of six different analyte concentrations were added individually to 10 µl of PBS containing 1 µl of human serum. The serum sample used for each analyte had a low endogenous level of that analyte, based on results from the antibody microarray profiling. Each dilution was labeled with biotin as described above, and another aliquot of each serum sample, without any analytes spiked in, was labeled with digoxigenin as a reference. Each biotin-labeled solution was mixed with an equal amount of digoxigenin-labeled reference, and the mixtures were analyzed on antibody microarrays using TC-RCA detection. The final analyte concentrations were 0, 0.2, 1, 5, 25 and 125 µg/ml, and the final serum dilutions were 1:40. Alternatively, purified proteins were spiked into a BSA background. Dilution series of complement C3, plasminogen, alpha-1-antitrypsin, cathepsin D, CRP, hemoglobin, IgG and IgM were spiked into 6 mg/ml bovine serum albumin (BSA) and labeled with biotin as described above. Other aliquots of each were labeled with digoxigenin, and the digoxigenin-labeled solutions from each analyte were pooled as a reference and mixed with the biotin-labeled solutions of that analyte. Six different analyte concentrations of complement C3 and plasminogen (0, 0.2, 1, 5, 25 and 125 µg/ml), eight different analyte concentrations of CRP, hemoglobin, IgG and IgM (0, 0.0008, 0.005, 0.028, 0.17, 1, 6 and 36 µg/ml), four different analyte concentrations of alpha-1-antitrypsin (0.1, 1, 10 and 100 µg/ml), and three different analyte concentrations of cathepsin D (0.1, 1 and 10 µg/ml) were incubated on the arrays and detected with TC-RCA or indirect detection. Zhou, H., Bouwman, K., Schotanus, M., Verweij, C., Marrero, J. A., Dillon, D., Costa, J., Lizardi, P. M., and Haab, B. B. Two-color, rolling-circle amplification on antibody microarrays for sensitive, multiplexed serum-protein measurements. Genome Biology, 5: R28, 2004). The digoxigenin-labeled analyte reference concentrations were the averages of the concentrations in each dilution series (since the solutions in a series were pooled to form the reference), and the final BSA concentration was 1.5 mg/ml in each color.

Example 9

Multiparametric Classification

The boosting decision tree method is a modification of the AdaBoost procedure (Freund, Y. and Schapire, R. A decision-theoretical generalization of on-line learning and an application to boosting. J Computer & Syst Sci, 55: 119-139, 1997), and the real boosting method (Yasui, Y., Pepe, M., Thompson, M. L., Adam, B. L., Wright, G. L., Jr., Qu, Y., Potter, J. D., Winget, M., Thornquist, M., and Feng, Z. A data-analytic strategy for protein biomarker discovery: profiling of high-dimensional proteomic data for cancer detection. Biostatistics, 4: 449-463, 2003) was developed to handle high-dimensional proteomic data. At each iteration, both boosting procedures update and assign weights to every sample in the classification based on the accuracy of the current selected classifier. The samples which are misclassified gain more weight in the next iteration. Therefore, the next classifier focuses on the samples misclassified by the previous classifier. In logistic regression with forward selection, samples are equally weighted, and at each iteration, the best classifier which has the lowest p-value among the remaining antibodies is selected into the linear combination of the previously selected classifiers. The coefficients of the classifiers are updated correspondingly. The inventor used a cross-validation process to determine the optimal number of antibodies in the final combined classifier for all three methods. For the boosting methods, a 10-fold cross-validation step is applied, where 90% of the samples are used as training set to define a best model for classification while 10% of the samples are reserved as testing set to determine the error rate of the model. This process is repeated ten times, each time using a different group of 90% for classification, and the cross-validation error is the average of the ten error rates. The classifier is considered final when the further addition of an antibody will not further decrease the cross-validation error. For logistic regression with forward selection, a 3-fold cross-validation step is applied similar to above. Although the empirical evidence supports the idea that the boosting may avoid over-fitting (Friedman, J. H., Hastie, T., and Tibshirani, R. Additive Logistice Regression: a Statistical View of Boosting. Annals of Statistics, 28: 337-407, 2000), there are counter examples, and no theoretical guidance exists as to when over-fitting may occur. The cross-validation process simulates the uncertainty in the classification algorithm and estimates the prediction error of the selected combined classifier. Therefore, this validation gives extra protection against the chance of over-fitting, or creating a classifier specifically for a particular sample set.

Example 10

Total DCP And Glycosylation Assays

The above-described antibody microarray method was used to measure both des-carboxy prothrombin (DCP) level and the level of glycosylated DCP in 23 serum samples from pancreatic cancer patients and 23 samples from healthy controls. An anti-DCP antibody was immobilized on a coated glass microscope slide, the proteins from each serum sample were labeled with digoxigenin and incubated on a glass slide. After washing off unbound protein, the digoxigenin label was detected by incubation with Cy5-labeled anti-digoxigenin and scanning for fluorescence at 635 nm (to detect Cy5). The Cy5 fluorescence reflects the total level of DCP in the serum, and the levels from each of the samples are shown by the line in the graphs (FIGS. 6 and 7). The levels in the cancer patients are significantly higher than the levels in the healthy subjects.

In addition, the inventor incubated a biotin-labeled lectin (Sambucus Nigra Lectin (SNA)) on the arrays after the serum samples had been incubated. SNA binds to sialic-acid-containing glycans on the proteins. The biotin was detected with streptavidin-phycoerythrin (SA-PE) and scanning at 532 nm. (The SA binds the biotin, and the PE fluoresces at 532 nm.) This signal reflects the amount of sialic-acid-containing glycans on the proteins that were captured by anti-DCP. This level is shown by the line (FIGS. 6 and 7). These levels are generally greater in the cancer patients than in the healthy controls, and the difference between the groups is greater than when measuring total protein. That observation means that the level of sialic acid on the DCP from cancer patients is greater than the level of sialic acid on normal DCP. The use of this glycosylation measurement could enhance the diagnostic performance of DCP.

Example 11

Detecting Glycans on Multiple Specific Proteins

Unlabeled serum samples are incubated on antibody microarrays, and after washing away unbound serum proteins, the glycan levels on the captured proteins are detected with a biotin-labeled lectin (FIG. 11A). A second version (FIG. 11B) is similar, except that the serum proteins are labeled with digoxigenin prior to application to an array, and the biotinylated lectin and digoxigenin-labeled proteins are detected with different color fluorescent dyes so that both protein levels and glycan levels can be measured in a single experiment. The detection of glycans on proteins captured by immobilized antibodies was confirmed after incubation of either buffer, unlabeled serum, or labeled serum on antibody arrays. The arrays were then incubated with biotinylated SNA lectin, followed by detection with Cy5-labeled anti-digoxigenin (red, 633 nm) and Cy3-labeled anti-biotin (green, 543 nm). The arrays were scanned at both 543 nm and 633 nm, and fluorescence from the spots are shown in both color channels from the indicated antibodies (FIG. 11C).

When no serum sample was incubated, very little binding from the SNA lectin or the anti-digoxigenin was detected at certain antibodies (FIG. 11C), although strong binding of certain lectins is observed on some other antibodies (not shown), meaning that the lectin bound to glycan groups on the capture antibodies.

Figure 12C:
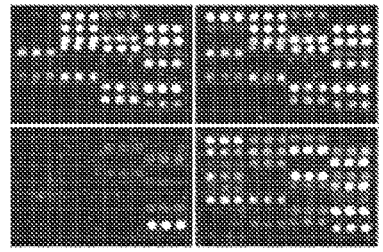
Figure 12D:
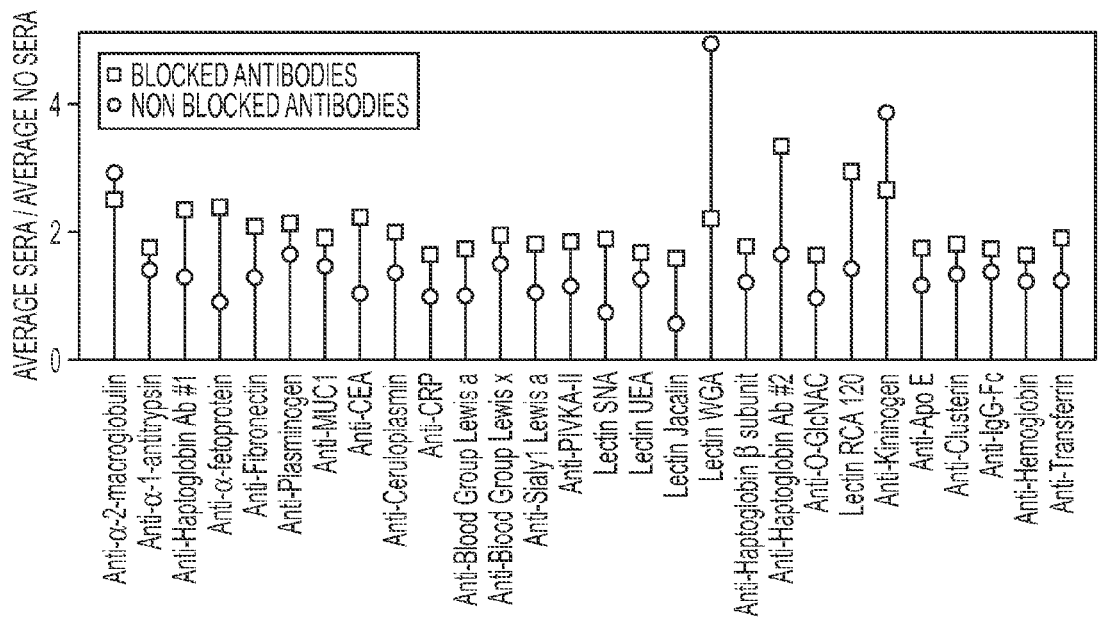

To prevent the GBPs from binding glycan groups on the spotted antibodies, the inventor developed a method to block such binding. Specifically, the method employs oxidation of the carbohydrate groups on the spotted antibodies, followed by derivatization with a hydrazide-maleimide bifunctional crosslinking reagent, followed by attachment of a cysteine-glycine dipeptide to the maleimide group (FIG. 12A). The inventor tested the ability of this method to block the binding of the lectin *Aleuria Aurantia* (AAL) to antibody arrays. The biotinylated AAL (from Vector Laboratories, Catalog No. B-1395) used by the inventor is isolated from *Aleuria aurantia* mushrooms. This lectin is a dimer of two identical subunits of about 36,000 daltons each with an isoelectric point of about pH 9. *Aleuria aurantia* lectin binds preferentially to fucose linked ($\alpha$-1,6) to N-acetylglucosamine or to fucose linked ($\alpha$-1,3) to N-acetyllactosamine related structures. The AAL used by the inventor bound strongly to many antibodies on arrays that had not been blocked (FIG. 12C, top left), with some addition binding to captured proteins after incubation of serum (FIG. 12C, top right). After blocking, very little AAL bound to the capture antibodies (FIG. 12C, bottom left), yet the blocked arrays still showed binding of the lectin after serum incubation (FIG. 12C, bottom right), indicating that the blocking procedure had not eliminated the antibody binding activities. The fluorescence intensity from incubated streptavidin-phycoerythrin is shown. The ratios of the AAL binding after serum incubation to the AAL binding after just buffer incubation showed that the blocking procedure significantly enhanced the detection of glycans on captured proteins relative to the undesired binding to the antibodies (FIG. 12D).

Figure 18:
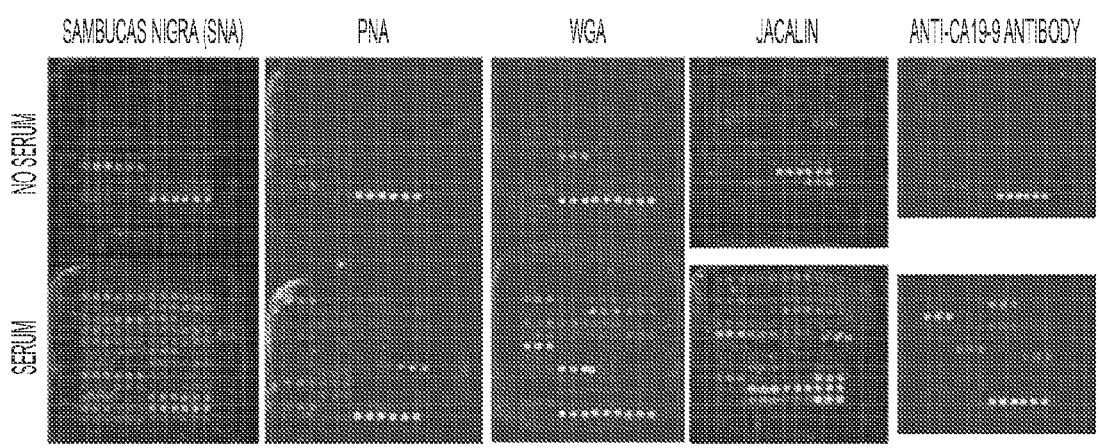
FIG. 18 shows images of antibody microarrays chemically blocked, and incubated with either a buffer solution (top arrays) or blood serum (bottom arrays).

Further establishing the effectiveness of the blocking method, the inventor chemically blocked arrays and incubated either with a buffer solution (top arrays) or blood serum (bottom arrays). The arrays were detected with the indicated lectins or the CA19-9 antibody (which binds a carbohydrate group) (FIG. 18). The spots lighting up in the top panels (FIG. 18) are positive controls and spotted lectins, which may bind the detection lectin. Binding of the detection lectins to the spotted antibodies is very weak. When serum is incubated, more signal at each antibody is detected FIG. 18, bottom panels), showing that the lectins are detecting captured proteins, not the spotted antibodies. The GBPs used in this work were SNA (Sambucus Nigra), PNA, WGA (Wheat Germ Agglutinin), Jacalin, and anti-CA19-9 antibody (FIG. 18).

Figure 13A:
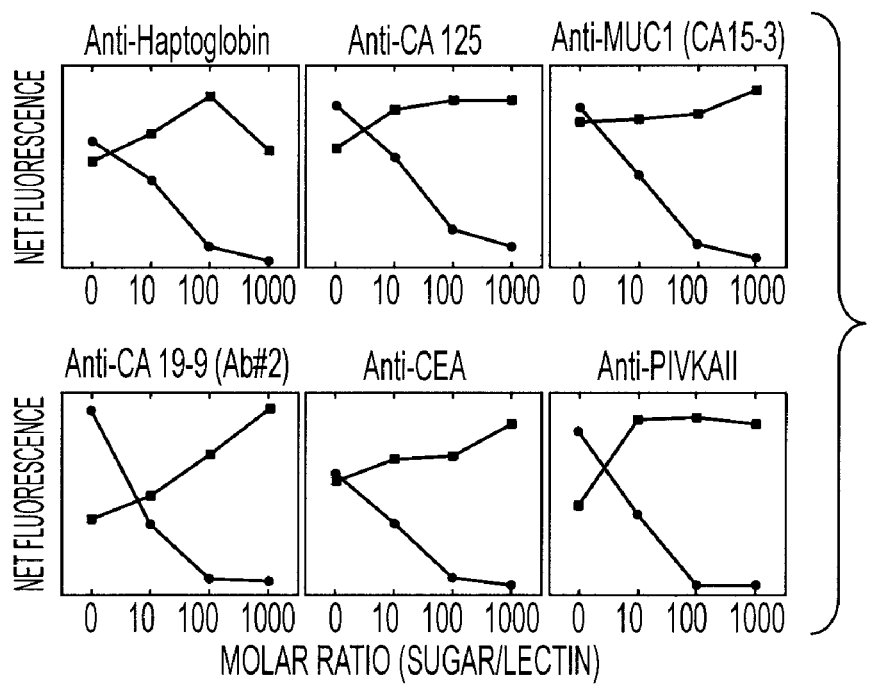
FIGS. 13A-B are graphs showing specificity of lectin binding to captured glycans.
Figure 13B:
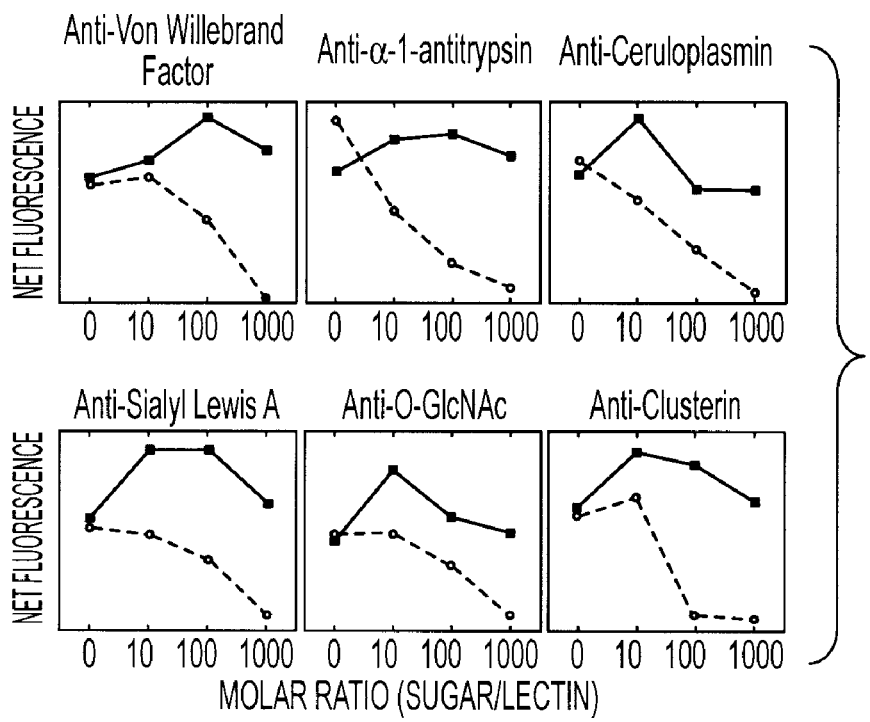

The binding of the lectin to glycan groups, rather than non-specific binding to the core protein, was confirmed through competitive binding with free sugars. The lectin AAL was pre-incubated with either L-fucose or sucrose (FIG. 13A), and the lectin Wheat Germ Agglutinin (WGA) was pre-incubated with either diacetyl chitobiose or sucrose (FIG. 13B), prior to application to arrays. The inventor also used biotinylated, succinylated WGA (from Vector Laboratories, Catalog No. B-1025S) isolated from *Triticum vulgaris* (wheat germ). This derivative has properties distinct from the native lectin. Evidence suggests that succinylated wheat germ agglutinin does not bind to sialic acid residues, unlike the native form, but retains its specificity toward N-acetylglucosamine (Eur. J. Biochem. 98, 39, 1979 and Eur. J. Biochem. 104, 147, 1980). Using conjugates of the native lectin and the succinylated form can provide a system to distinguish between sialylated glycoconjugates and those containing only N-acetylglucosamine structures.

Each lectin preparation was incubated on an antibody array that had been incubated with a serum sample (all arrays had the same sample). The lectin concentration was held constant at 10 µg/ml. The fluorescence intensity from streptavidin-phycorerythrin at the indicated antibodies is shown (FIG. 13). In each case, lectin binding to captured serum proteins was reduced by the L-fucose or diacetyl chitobiose, but not by the sucrose, indicating the lectins were binding to the captured proteins according to their particular glycan specificities. The antibodies shown here were of interest for associations with cancer (see below) and are representative of all antibodies on the arrays.

Example 12

Measuring Variation in Glycans on Serum Protein

The inventor tested the ability to measure changes in glycan levels across different serum samples using the method of FIG. 11B, which allows the detection of both protein level and glycan level in the same experiment. These initial tests were performed on arrays that were not chemically blocked, focusing on antibodies that showed low lectin binding and assessing the ability to detect glycan variation on top of non-specific binding to the antibodies. Twenty-three serum samples from pancreatic cancer patients and 23 serum samples from healthy controls were labeled with the digoxigenin tag, incubated on antibody microarrays, and detected with the lectin indicated (Table 7) and Cy-5-labeled antidigoxigenin. Six sets of the 46 samples were run, and each set was incubated with a different biotinylated lectin, using the lectins SNA (in duplicate), AAL (in duplicate), Maackia Amurensis (MAA), and wheat germ agglutinin (WGA).

T-tests were performed on data from the individual color channels and on the ratio between the two. Few glycan differences were revealed using the SNA and MAA lectins, but many differences were revealed using the AAL and WGA lectins (Table 7).

TABLE 7

| Name | p-value: set 1, set 2 |
|---|---|
| Detected with AAL | |
| *Net 633* | |
| Anti-PIVKA-II | 0.002, <0.001 |
| Anti-Von Willebrand Factor | 0.02, <0.001 |
| *Net 543* | |
| Anti-Alpha 2-macroglobulin | <0.001, <0.001 |
| Anti-Hemoglobin | <0.001, <0.001 |
| Anti-Alpha-1-antitrypsin | 0.001, <0.001 |
| Anti-von Willebrand Factor | 0.002, <0.001 |
| Anti-Haptoglobin beta subunit | 0.009, <0.001 |
| anti-Haptoglobin | 0.01, 0.002 |
| Lectin, Wheat germ agglutinin | 0.01, <0.001 |
| Lectin, Jacalin | 0.008, 0.004 |
| Lectin, Erythrina Cristagalli | 0.01, 0.003 |
| *Ratio 543/633* | |
| Anti-Alpha-1-antitrypsin | <0.001, <0.001 |
| anti-Haptoglobin | <0.001, <0.001 |
| Anti-Alpha 2-macroglobulin | <0.001, <0.001 |
| Anti-Hemoglobin | <0.001, 0.003 |
| anti-Albumin | <0.001, 0.01 |
| Anti-PIVKA-II | 0.02, 0.003 |
| Lectin, Wheat germ agglutinin | 0.02, 0.02 |
| Anti-Haptoglobin beta subunit | 0.04, 0.005 |

| Name | p-value |
|---|---|
| Detected with MAA | |
| *Net 633* | |
| Anti-Von Willebrand Factor | <0.001 |
| Anti-PIVKA II | 0.001 |
| Lectin, Wheat Germ Agglutinin (WGA) | 0.002 |
| Anti-CRP | 0.05 |
| *Net 543* | |
| Lectin, Wheat Germ Agglutinin (WGA) | 0.001 |
| Lectin, Aleuria Aurantia | 0.01 |
| Anti-IgA | 0.02 |
| IgG, Rabbit | 0.02 |
| Lectin, Dolichos Biflorus Agglutinin (DBA) | 0.04 |
| *Ratio 543/633* | |
| Anti-Von Willebrand Factor | <0.001 |
| Lectin, Wheat Germ Agglutinin (WGA) | <0.001 |
| Anti-PIVKA-II | 0.03 |

TABLE 7-continued

| Name | p-value |
|---|---|
| Detected with WGA | |
| *Net 633* | |
| Anti-Von Willebrand Factor | <0.001 |
| *Net 543* | |
| Anti-Von Willebrand Factor | <0.001 |
| Lectin, Wheat Germ Agglutinin (WGA) | <0.001 |
| Lectin, Erythrina Cristigalli | <0.001 |
| Lectin, Bauhinia Purpurea (BPL) | <0.001 |
| Anti-CRP | <0.001 |
| Anti-GLA | <0.001 |
| Anti-Sialyl Lewis A | <0.001 |
| Anti-MUC1 (CA15-3) | 0.001 |
| Anti-IgA | 0.006 |
| Lectin, Vicia Villosa (VVL) | 0.006 |
| Lectin, Aleuria Aurantia | 0.008 |
| Anti-CA 19-9 | 0.011 |
| Anti-CEA | 0.011 |
| Anti-Plasminogen | 0.022 |
| anti-Haptoglobin | 0.027 |
| anti-Haptoglobin b subunit | 0.029 |
| Lectin, Lotus Tetragonolobus (LTL) | 0.044 |
| anti-Blood group Lewis A | 0.048 |
| *Ratio 543/633* | |
| Anti-CA 19-9 | <0.001 |
| Anti-Blood group Lewis A | <0.001 |
| Lectin, Wheat Germ Agglutinin (WGA) | <0.001 |
| Lectin, Bauhinia Purpurea (BPL) | 0.02 |
| Lectin, Aleuria Aurantia | 0.03 |
| Anti-Lipase | 0.048 |

| Name | p-value: set 1, set 2 |
|---|---|
| Detected with SNA | |
| *Net 633* | |
| Anti-Von Willebrand Factor | <0.001, <0.001 |
| Anti-PIVKA-II | 0.003, <0.001 |
| Anti-CRP | 0.02, 0.03 |
| *Net 543* | |
| Anti-PIVKA-II | <0.001, <0.001 |
| Anti-Von Willebrand Factor | 0.001, <0.001 |
| *Ratio 543/633* | |
| None | |

P-values are shown just for the significant antibodies (p<0.05). For the AAL and SNA data, p-values are given for those that were significant in both of the replicates.

The antibodies and lectins were purchased from various sources. The antibodies used are summarized in Table 8. The antibodies were purified and prepared as described earlier (Orchekowski, R. P. et al. Antibody microarray profiling reveals individual and combined serum proteins associated with pancreatic cancer. *Cancer Research*, in press (2005)).

TABLE 8

| Name | Used In Set | Origin | Clonality | Source/Manufacturer | Catalog Number |
|---|---|---|---|---|---|
| Anti-Von Willebrand Factor | 1, 2, 3 | Rabbit | Polyclonal | DAKO | A0082 |
| Anti-α-1-antitrypsin | 1, 2, 3 | Mouse | Monoclonal | Biotrend | 0640-5507 |
| Anti-Haptoglobin (ab#1) | 1, 2, 3 | Sheep | Polyclonal | Biotrend | 4890-0004 |
| Anti-MUC1 (CA15-3) (Ab#1) | 1, 2, 3 | Mouse | Monoclonal | USBio | C0050-23 |
| Anti-Carcinoembryonic Antigen (CEA) | 1, 2, 3 | Mouse | Monoclonal | USBio | C1299-94 |
| Anti-Ceruloplasmin | 1, 2, 3 | Goat | Polyclonal | Sigma | C0912 |

TABLE 8-continued

| Name | Used In Set | Origin | Clonality | Source/Manufacturer | Catalog Number |
|---|---|---|---|---|---|
| Anti-C-reactve Protein (CRP) | 1, 2, 3 | Mouse | Monoclonal | USBio | C7907-10 |
| Anti-Blood Group Lewis a | 1, 2, 3 | Mouse | Monoclonal | AbCam | ab3967 |
| Anti-Sialyl Lewis a | 1, 2, 3 | Mouse | Monoclonal | AbCam | ab3982 |
| Anti-Des-Carboxy Prothrombin (DCP) | 1, 2, 3 | Mouse | Monoclonal | USBio | P4210-50 |
| *Sambusu Nigra* Lectin (SNA) | 1, 2, 3 | N/A | N/A | Calbiochem | 431792 |
| *Ulex Europaeus* Agglutinin (UEA I) | 1, 2, 3 | N/A | N/A | Vector Laboratories | L-1060 |
| Jacalin Lectin | 1, 2, 3 | N/A | N/A | Vector Laboratories | L-1150 |
| Wheat Germ Agglutinin (WGA) | 1, 2, 3 | N/A | N/A | Vector Laboratories | L-1020 |
| Anti-Haptoglobin β-subunit | 1, 2, 3 | Mouse | Monoclonal | Sigma | H 6395 |
| Anti-Haptoglobin (Ab#2) | 1, 2, 3 | Rabbit | Polyclonal | Sigma | H 8636 |
| Anti-O-linked N-Acetyl glucosamine | 1, 2, 3 | Mouse | Monoclonal | AbCam | ab2739 |
| Anti-IgG-Fc | 1, 2, 3 | Goat | Polyclonal | Bethyl | A80-104A |
| Anti-Hemoglobin | 1, 2, 3 | Sheep | Polyclonal | Bethyl | E80-135 (kit) |
| Anti-Transferrin | 1, 2, 3 | Goat | Polyclonal | Bethyl | E80-128 (kit) |
| Anti-α 2-macroglobulin | 1, 2 | Rabbit | Polyclonal | Sigma | M1893 |
| IgG, Goat | 1, 2 | Goat | N/A | Jackson ImmunoResearch | 005-000-003 |
| IgG, Rabbit | 1, 2 | Rabbit | N/A | Jackson ImmunoResearch | 011-000-003 |
| Anti-CA19-9 (Ab#2) | 1, 3 | Mouse | Monoclonal | USBio | C0075-27 |
| Anti-Gla | 1, 3 | Mouse | Monoclonal | American Diagnostica, Inc. | 3570 |
| *Aleuria Aurantia* Lectin (AAL) | 1, 3 | N/A | N/A | Vector Laboratories | L-1390 |
| *Bauhinia Purpurea* Lectin (BPL) | 1, 3 | N/A | N/A | Vector Laboratories | L-1280 |
| Erythrina Cristigalli Lectin (ECL) | 1, 3 | N/A | N/A | Vector Laboratories | L-1140 |
| Lectin, Vicia Villosa (VVL) | 1, 3 | N/A | N/A | Vector Laboratories | L-1230 |
| Anti-IgA | 1, 3 | Goat | Polyclonal | Bethyl | E80-102 (kit) |
| Anti-α-fetoprotein (Ab#1) | 2, 3 | Mouse | Monoclonal | Biotrend | 4F16 |
| anti-Thrombospondin-1 | 2, 3 | Mouse | Monoclonal | Lab Vision | MS-590-PABX |
| Ricinus communis Agglutinin I (RCA 120) | 2, 3 | N/A | N/A | Vector Laboratories | L-1080 |
| anti-Apolipoprotein E (Apo E) | 2, 3 | Mouse | Monoclonal | Chemicon International, Inc. | MAB1062 |
| Anti-Clusterin (apolipoprotein J, Apo J) | 2, 3 | Mouse | Monoclonal | Alexis (Axxora) | ALX-804-126-C100 |
| Anti-IgM | 1 | Goat | Polyclonal | Jackson Immunoresearch | 109-005-043 |
| Anti-alkaline phosphatase (AP) | 1 | Mouse | Monoclonal | Biotrend | 0300-0430 |
| Anti-beta lipoprotein (LDL) | 1 | Rabbit | Polyclonal | Biotrend | 5685-3010 |
| Anti-MUC1 (CA 15-3) (Ab#2) | 1 | Mouse | Monoclonal | Ilan/Jim Resau (VAI) | Unknown |
| Anti-Caveolin-1 | 1 | Rabbit | Polyclonal | Sigma | C3237 |
| Anti-Lipase | 1 | Mouse | Monoclonal | USBio | L2496-02 |
| Anti-Hemoglobin, glycated | 1 | Mouse | Monoclonal | USBio | H1850-21 |
| Dolichos Biflorus Agglutinin (DBA) | 1 | N/A | N/A | Vector Laboratories | L-1030 |
| Lotus Tetragonolobus Lectin (LTL) | 1 | N/A | N/A | Vector Laboratories | L-1320 |
| Anti-Albumin | 1 | Mouse | Monoclonal | Fitzgerald | 10-A75 |
| Anti-Fibronectin | 2 | Rabbit | Polyclonal | Sigma | F 3648 |
| Anti-Plasminogen | 2 | Mouse | Monoclonal | USBio | P4256-27A |
| Anti-Cathepsin B | 2 | Goat | Polyclonal | R&D Systems | AF953 |
| IgG, Mouse | 2 | Mouse | N/A | Jackson ImmunoResearch | 015-000-003 |
| IgG, Sheep | 2 | Sheep | N/A | Jackson ImmunoResearch | 013-000-003 |
| Anti-Blood Group Lewis x | 2 | Mouse | Monoclonal | AbCam | ab3358 |
| anti-Kininogen | 2 | Goat | Polyclonal | R & D Systems | AF1569 |
| Anti-IL-8 | 3 | Goat | Polyclonal | R & D Systems | AB-208-NA |
| Anti-Laminin | 3 | Mouse | Monoclonal | Sigma | L 8271 |
| Anti-CA125 | 3 | Mouse | Monoclonal | USBio | C0050-01 |
| Anti-CA19-9 (Ab#1) | 3 | Mouse | Monoclonal | USBio | C0075-07 |
| Anti-α-fetoprotein | 3 | Mouse | Monoclonal | Sigma | A8452 |
| Anti-Cathepsin D | 3 | Goat | Polyclonal | R&D Systems | AF1014 |
| anti-Protein S | 3 | Sheep | Polyclonal | USBio | P9108-09 |
| Peanut Agglutinin (PNA) | 3 | N/A | N/A | Vector Laboratories | L-1070 |
| anti-90K/Mac-2BP | 3 | Mouse | Monoclonal | Bender MedSystems | BMS146 |

Figure 14A:
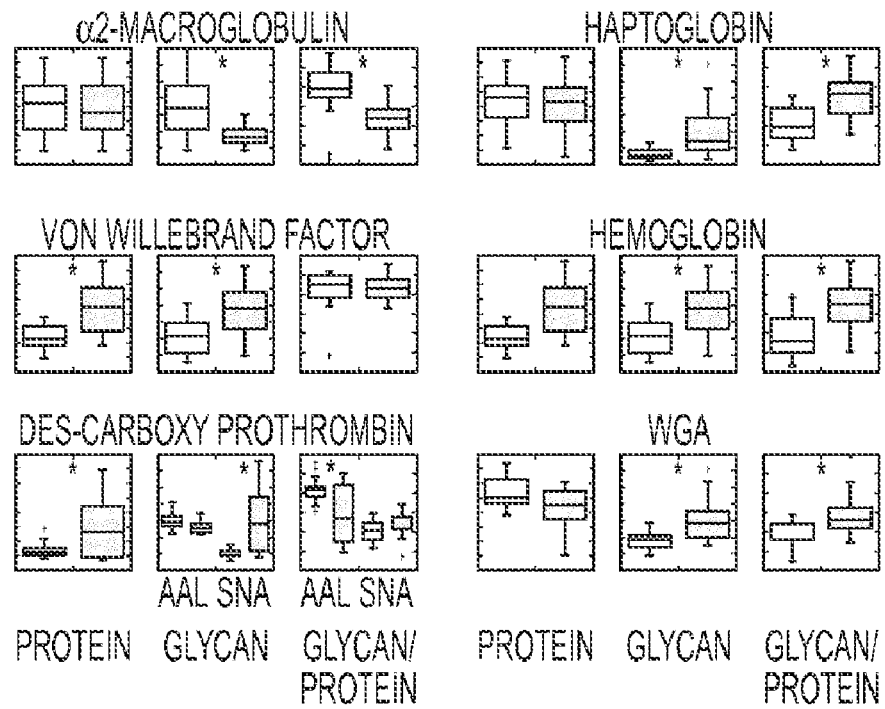
FIGS. 14A-B show distributions of protein and glycan levels and gel-based validation.

Several different behaviors of glycan and total protein variation were observed after detection with the AAL lectin (FIG. 14A). For each indicated antibody, the distributions of red fluorescence (indicating total protein binding), green fluorescence (indicating AAL lectin binding), and ratio of green-to-red (indicating amount of AAL binding relative to protein level) were found, using the average results from two replicate experiment sets. Results from both the AAL and SNA lectins are shown for des-carboxy prothrombin. The antibody to alpha-2-macroglobulin had similar captured protein levels (red signal) between the groups, but the lectin binding (green signal), and the ratio of lectin binding to captured protein (green:red ratio), were significantly lower in cancer. In contrast, the antibodies targeting haptoglobin and hemoglobin (which can be complexed together) showed similar captured protein levels but higher lectin binding in cancer. The von Willebrand factor antibody showed elevated lectin binding in cancer but also elevated captured protein, so the glycan-to-protein ratio did not change between the groups. The protein des-carboxy prothrombin (DCP) showed unique lectin binding patterns: both SNA and AAL binding were altered in cancer, but in different directions. The lectin SNA, which binds sialic acid, showed increased glycan:protein ratios in cancer, but the AAL lectin, which targets fucose, showed lower glycan:protein ratios in cancer. The final example (lower right in FIG. 14A) shows the use of a lectin as the capture agent, showing that total glycoprotein levels defined by the lectins WGA and AAL are elevated in pancreatic cancer.

Figure 14B:
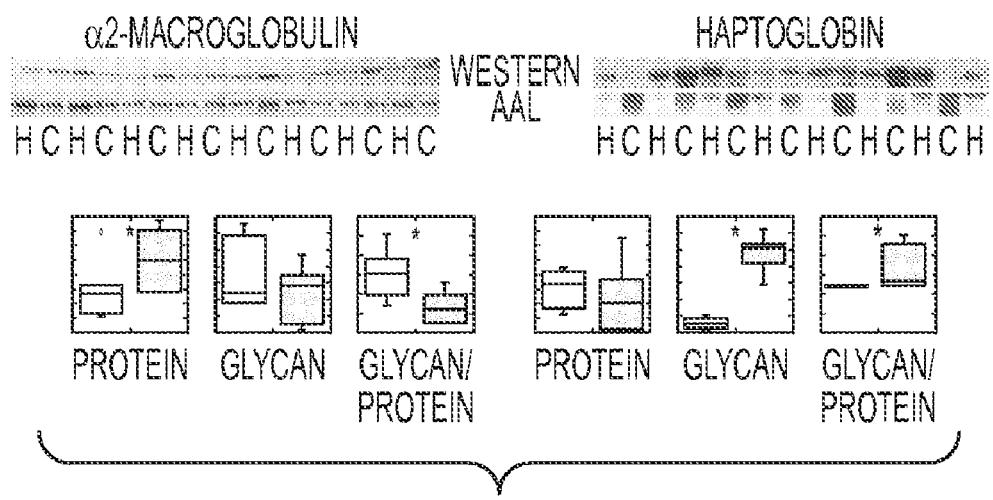

FIG. 14B shows Western blot studies used to confirm the trends in glycosylation alterations as measured by microarray. The relative levels of haptoglobin and alpha-2-macroglobulin were probed in 15 and 16 samples by immunoblot, respectively, and the same bands were again probed using the lectin AAL after stripping the blot (FIG. 14B, top). The intensities of the bands were quantified to obtain the distributions of protein levels (band intensities from the anti-haptoglobin or anti-alpha-2-macroglobulin blots), glycan levels (band intensities from the AAL blots), and the glycan-to-protein levels (ratios of the previous two band intensities) in the cancer (dark bars) and healthy control patient (white bars) samples (FIG. 14B, bottom). The boxes give the upper and lower quartiles of the measurements with respect to the median value (horizontal line in each box), and the lines give the ranges of the measurements, excluding outliers, which are represented by circles. The asterisk indicates a significant difference (p<0.05) between the groups. The distributions followed the same trends as observed in the microarray data; the level of AAL binding was increased on haptoglobin and decreased on alpha-2-macroglobulin in cancer, relative to the respective protein levels.

Example 13

Profiling Glycolsylation Alterations on Serum Proteins in Pancreatic Cancer

The inventor investigated the associations of multiple glycan and protein levels with cancer using a larger set of serum samples (Table 9) on chemically-blocked arrays. As discussed herein, the profiling of glycan variation, using the lectins AAL and WGA, over serum samples from pancreatic cancer patients and control subjects showed multiple proteins with potential cancer-associated glycan elevations or reductions. The patterns of reactivity from the two lectins were very different from each other, indicating distinct mechanisms of regulation for those glycans. Parallel glycan-detection and sandwich assays showed that glycans reactive with the CA19-9 monoclonal antibody were elevated on the proteins carcinoembryonic antigen and MUC1 in sera from pancreatic cancer patients, which could influence the binding and functional properties of those proteins. As demonstrated by these data, antibody arrays with glycan detection are highly effective for profiling variation in specific glycans on multiple proteins and should be useful in diverse areas of glycobiology research.

TABLE 9

| Class | Number | Age | % Male |
| --- | --- | --- | --- |
| Healthy Source | 110 | 46.9 (13.4) | 35.5 |
| ENH | 33 | 49.4 (11.9) | 54.5 |
| UM | 77 | 45.9 (14.0) | 27.2 |
| Pancreatic Cancer | 119 | 68.1 (11.4) | 49.6 |
| ENH | 89 | 70.0 (11.4) | 51.7 |
| UM | 30 | 62.4 (9.9) | 50.0 |
| Benign Disease | 104 | 57.0 (15.0) | 49.0 |
| ENH | 89 | 58.3 (14.9) | 51.7 |
| UM | 15 | 49.3 (13.6) | 33.3 |

ENH: Evanston Northwestern Healthcare;
UM: University of Michigan.
The mean and % male are given, with the standard deviation of the ages in parentheses.

ENH: Evanston Northwestern Healthcare; UM: University of Michigan. The mean and %male are given, with the standard deviation of the ages in parentheses.

The one-color method (FIG. 11A) was chosen for these experiments to eliminate the possibility of interaction between the lectin and the anti-digoxigenin. The sample set was run three times: twice detected with the lectin AAL and once with the lectin WGA.

Many antibodies showed significantly different lectin binding levels (p<0.05) between the patient groups using both the AAL and WGA lectins. Table 10 describes antibodies showing discrimination between patient classes, with p-values.

TABLE 10

| AAL | | | | WGA | | | |
| --- | --- | --- | --- | --- | --- | --- | --- |
| Antibodies/Lectins | Cancer vs Healthy | Cancer vs Benign | Benign vs Healthy | Antibodies/Lectins | Cancer vs Healthy | Cancer vs Benign | Benign vs Healthy |
| Anti-Haptoglobin β-subunit | 3.7E−05 | 4.4E−03 | >0.05 | Anti-CA 19-9 (Ab#1) | 4.3E−11 | 7.2E−09 | >0.05 |
| Anti-O-linked N-acetyl glucosamine | 8.2E−04 | 0.037 | >0.05 | Anti-CA 19-9(Ab#2) | 3.5E−06 | 1.8E−04 | >0.05 |
| Anti-Blood Group Lewis x | 1.6E−03 | 2.5E−03 | >0.05 | Anti-Blood group Lewis a | 2.2E−05 | 1.1E−03 | >0.05 |
| Sambucus Nigro Lectin | 2.6E−07 | >0.05 | 2.0E−04 | Anti-α-fetoprotein (Ab#2) | 1.5E−04 | 0.032 | >0.05 |
| Anti-Apolipoprotein E | 7.4E−05 | >0.05 | 0.017 | Ulex Europaeus Agglutinin I | 4.5E−04 | 7.2E−03 | >0.05 |
| Jacalin Lectin | 1.7E−04 | >0.05 | 4.6E−03 | Anti-O-linked N-acetyl glucosamine | 8.0E−03 | 4.0E−03 | >0.05 |
| Ulex Europaeus Agglutinin I | 1.1E−06 | 0.02 | 0.014 | Anti-Protein S | 1.1E−03 | 0.037 | >0.05 |
| Anti-Von Willebrand Factor | 3.6E−09 | 0.046 | 2.6E−04 | Anti-Sialyl Lewis a | 8.9E−03 | 0.043 | >0.05 |
| Anti-Haptoglobin (Ab#2) | 3.1E−15 | 4.2E−5 | 5.7E−6 | Anti-GLA | 0.011 | 0.028 | >0.05 |
| Anti-Clusterin | 9.6E−15 | 3.9E−05 | 1.0E−04 | Anti-90K | 0.040 | 0.030 | >0.05 |
| Anti-Kininogen | 4.6E−11 | 7.4E−04 | 1.9E−03 | Anti-Laminin | 4.6E−06 | >0.05 | 0.017 |
| Anti-Ceruloplasmin | 4.8E−11 | 2.7E−04 | 7.2E−03 | Anti-IL-8 | 1.8E−05 | >0.05 | 4.9E−03 |
| Ricinus Communis Agglutinin I | 8.5E−10 | 0.009 | 7.5E−04 | Anti-Des-Carboxy Prothrombin | 2.9E−05 | >0.05 | 0.021 |
| Anti-C-reactive Protein | 1.2E−09 | 0.009 | 3.46E−05 | Anti-C-reactive Protein | 3.5E−05 | >0.05 | 1.5E−03 |
| Ant-α-fetoprotein (Ab#1) | 7.5E−09 | 0.004 | 5.7E−03 | Anti-Carcinoembryonic Antigen | 5.0E−05 | >0.05 | 0.022 |
| Anti-α-1-antitrypsin | 3.6E−07 | 0.019 | 6.9E−03 | Erythrina Cristagalli Lectin | 0.041 | >0.05 | 0.021 |
| Anti-Sialyl Lewis a | 1.8E−06 | 0.046 | 4.3E−03 | Vicia Villosa Lectin | 5.3E−06 | 0.013 | 0.045 |
| Wheat Germ Agglutinin | 2.2E−06 | 0.009 | 0.026 | Anti-Von Willebrand Factor | 7.8E−06 | 0.039 | 0.011 |
| Anti-α-2-macroglobuline | 0.026 | >0.05 | >0.05 | Anti-Haptoglobin (Ab#1) | 8.0E−06 | 0.049 | 0.015 |
| Anti-Plasminogen | 6.0E−04 | >0.05 | >0.05 | Anti-CA125 | 1.2E−05 | 0.035 | 6.4E−03 |

TABLE 10-continued

| | AAL | | | | WGA | | |
| --- | --- | --- | --- | --- | --- | --- | --- |
| Antibodies/Lectins | Cancer vs Healthy | Cancer vs Benign | Benign vs Healthy | Antibodies/Lectins | Cancer vs Healthy | Cancer vs Benign | Benign vs Healthy |
| Anti-MUC1 (CA15-3)(Ab#2) | 5.4E−03 | >0.05 | >0.05 | Anti-MUC1 (CA15-3)(Ab#2) | 6.1E−04 | >0.05 | >0.05 |
| Anti-Carcinoembryonic Antigen | 9.9E−03 | >0.05 | >0.05 | Anti-α-1-antitrypsin | 6.3E−04 | >0.05 | >0.05 |
| Anti-Fibronectin | 0.016 | >0.05 | >0.05 | Wheat Germ Agglutinin | 4.3E−03 | >0.05 | >0.05 |
| | | | | Anti-α-fetoprotein (Ab#1) | 5.6E−03 | >0.05 | >0.05 |
| | | | | Anti-Cathepsin D | 6.2E−03 | >0.05 | >0.05 |
| | | | | Anti-Transferrin | 8.9E−03 | >0.05 | >0.05 |
| | | | | *Bouhinia Purpurea* Lectin | 0.018 | >0.03 | >0.05 |
| | | | | Anti-Ceruloplasmin | 0.021 | >0.05 | >0.05 |
| | | | | Anti-Clusterin | >0.05 | 0.032 | >0.05 |
| | | | | *Aleuria Aurantia* Lectin | >0.05 | 0.033 | >0.05 |
| | | | | Peanut Agglutinin | >0.05 | 0.043 | >0.05 |
| | | | | *Jacalin* Lectin | >0.05 | >0.05 | 0.037 |

All of the differences were higher in cancer relative to healthy and benign disease and higher in benign disease relative to healthy, except for alpha-2-macroglobulin, which was lower in cancer when detected with AAL, consistent with the data of FIG. 14. The agreement between these data, collected using chemically-blocked antibodies, and the data collected with unmodified antibodies (FIG. 4 and Table 8) provided further indication that the blocking procedure did not affect the binding activities of the antibodies. The duplicate AAL sets showed that the data are reproducibile. The correlations between the duplicate experiment sets ranged from 0.36 to 0.76 for the antibodies of Table 9, with the best discriminators above 0.70, which is good correlation over 333 samples. In addition, of the 23 antibodies that discriminated the patient groups in AAL set two (presented in Table 10), 21 also discriminated the patient groups in set one.

The unmatched age distributions between the different groups could be a source of bias in the comparisons. The inventor tested that source of bias by comparing the glycan levels between the older third and younger third of subjects within each patient group. Detection with WGA revealed only one antibody with different levels (p<0.05) between any of the groups (von Willebrand factor higher in older subjects with benign disease), and detection with AAL showed no reproducible (p<0.05 in both sets one and two) differences between the groups. This analysis indicates that age differences are likely not major contributors to the observed differences between the patient groups.

The inventor investigated whether any of the antibody-lectin pairs, or combinations of pairs, could possibly be used as a biomarker for pancreatic cancer. The highest discrimination between cancer and the other classes was given by anti-CA19-9 detected with WGA. The area-under-the-curve (AUC) in receiver-operator characteristic analysis was 0.92 (81% sensitivity and 90% specificity) in the comparison of the cancer to healthy classes, and 0.86 (77% sensitivity and 81% specificity) in the comparison of the cancer and benign classes. The next best discriminators were CA125 detected with WGA (0.78 and 0.65 AUC comparing cancer to healthy and cancer to benign, respectively) and haptoglobin detected with AAL (0.81 and 0.66 AUC comparing cancer to healthy and cancer to benign, respectively). Since CA19-9 detected with WGA was much stronger than the other markers, the use of logistic regression and boosting algorithms to classify the samples based on combinations of multiple markers provided no statistical improvement in classification accuracy over the use of that marker alone, which has similar performance to the standard CA19-9 assay.

The inventor compared profiles between the data sets to gain insights into the coordinated regulation of the WGA-reactive and AAL-reactive glycan structures. Some antibodies strongly discriminated the patient groups with one lectin but not the other, which indicated cancer-related, differential regulation of the structures. Table 11 describes antibodies used in both AAL and WGA detection experiments, with p-values for each class comparison.

TABLE 11

| | AAL | | | WGA | | |
| --- | --- | --- | --- | --- | --- | --- |
| Antibodies/Lectins | Cancer vs Healthy | Cancer vs Benign | Benign vs Healthy | Cancer vs Healthy | Cancer vs Benign | Benign vs Healthy |
| Anti-Haptoglobin β-subunit | 3.7E−05 | 4.4E−03 | 0.175 | 0.095 | 0.645 | 0.631 |
| Anti-O-linked N-acetyl glucosamine | 8.2E−04 | 0.037 | 0.099 | 8.0E−03 | 4.0E−03 | 0.913 |
| Anti-Von Willebrand Factor | 3.6E−09 | 0.046 | 2.6E−04 | 7.8E−06 | 0.039 | 0.011 |
| *Sambucus Nigra* Lectin | 2.6E−07 | 0.140 | 2.0E−04 | 0.092 | 0.422 | 0.410 |
| *Ulex Europaeus* Agglutinin I | 1.1E−06 | 0.020 | 0.014 | 4.5E−04 | 7.2E−03 | 0.344 |
| Anti-Apolipoprotein E | 7.4E−05 | 0.31 | 0.017 | 0.156 | 0.363 | 0.310 |
| *Jacalin* Lectin | 1.7E−04 | 0.726 | 4.6E−03 | 0.750 | 0.088 | 0.037 |
| Anti-Haptoglobin (Ab#2) | 3.1E−15 | 4.2E−5 | 5.7E−6 | 0.092 | 0.095 | 0.936 |
| Anti-Clusterin | 9.6E−15 | 3.9E−05 | 1.0E−04 | 0.421 | 0.032 | 0.323 |
| Anti-Ceruloplasmin | 4.8E−11 | 2.7E−04 | 7.2E−03 | 0.021 | 0.466 | 0.095 |
| *Ricinus Communis* Agglutinin I | 8.5E−10 | 0.009 | 7.5E−04 | 0.552 | 0.820 | 0.614 |
| Anti-C-reactive Protein | 1.2E−09 | 0.009 | 3.46E−05 | 3.5E−05 | 0.210 | 1.5E−03 |
| Ant α-fetoprotein (Ab#1) | 7.5E−09 | 0.004 | 5.7E−03 | 5.6E−03 | 0.065 | 0.588 |
| Anti-α-1-antitrypsin | 3.6E−07 | 0.019 | 6.9E−03 | 6.3E−04 | 0.058 | 0.104 |

TABLE 11-continued

|  | AAL | | | WGA | | |
| --- | --- | --- | --- | --- | --- | --- |
| Antibodies/Lectins | Cancer vs Healthy | Cancer vs Benign | Benign vs Healthy | Cancer vs Healthy | Cancer vs Benign | Benign vs Healthy |
| Anti-Sialyl Lewis a | 1.8E−06 | 0.046 | 4.3E−03 | 8.9E−03 | 0.043 | 0.464 |
| Wheat Grem Agglutinin | 2.2E−06 | 0.009 | 0.026 | 4.3E−03 | 0.249 | 0.084 |
| Anti-MUC1 (CA15-3)(Ab#2) | 5.4E−03 | 0.192 | 0.243 | 6.1E−04 | 0.140 | 0.076 |
| Anti-Carcinoembryonic Antigen | 9.9E−03 | 0.256 | 0.177 | 5.0E−05 | 0.212 | 0.022 |
| Anti-Haptoglobin(Ab#1) | 0.272 | 0.290 | 0.981 | 8.0E−06 | 0.049 | 0.015 |
| Anti-Blood Group Lewis A | 0.784 | 0.441 | 0.276 | 2.2E−05 | 1.1E−03 | 0.224 |
| Anti-Des-Carboxy Prothrombin | 0.196 | 0.535 | 0.552 | 2.9E−05 | 0.181 | 0.021 |
| Anti-IgG Fc | 0.097 | 0.598 | 0.607 | 0.121 | 0.734 | 0.397 |
| Anti-Hemoglobin | 0.289 | 0.319 | 0.950 | 0.312 | 0.572 | 0.829 |
| Anti-Transferrin | 0.704 | 0.321 | 0.151 | 8.9E−03 | 0.970 | 0.055 |

Figure 16:
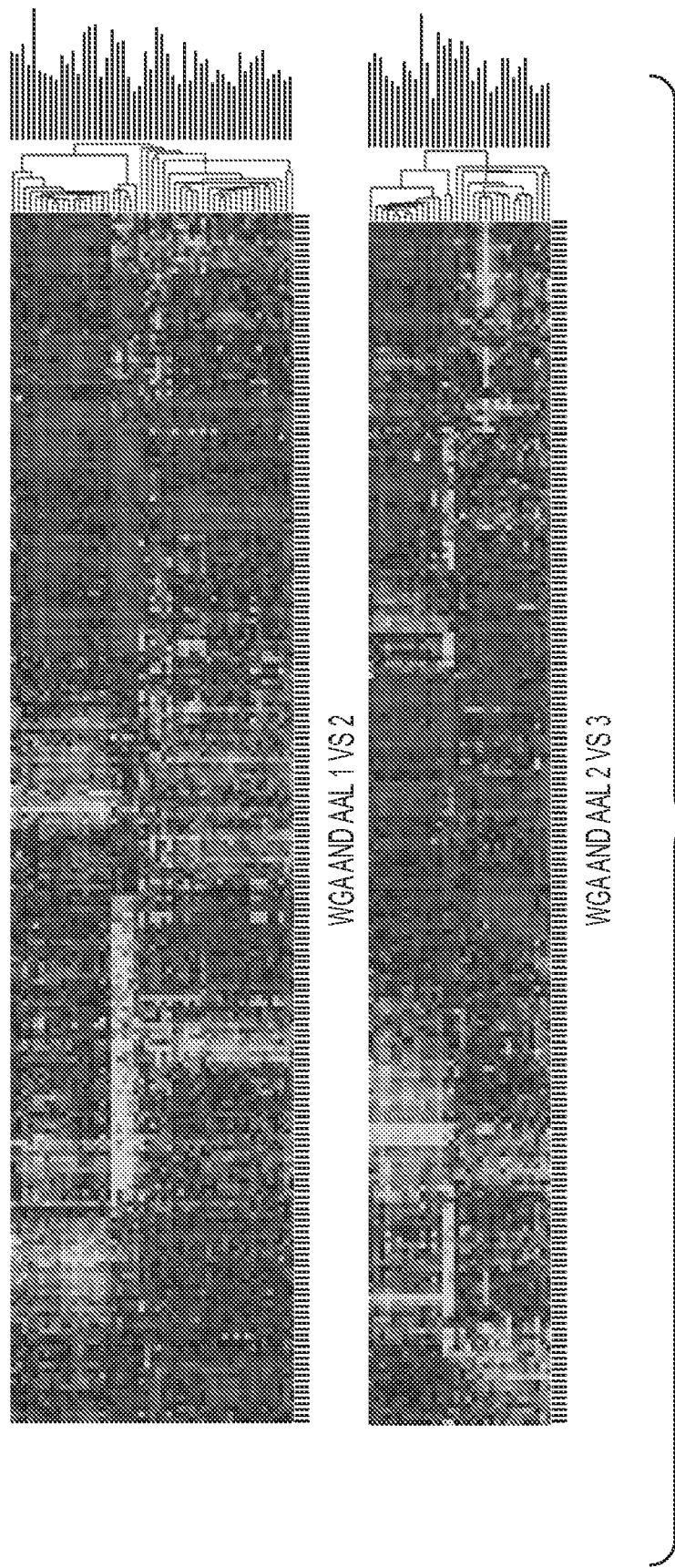
FIG. 16 shows clusters of glycan measurements using only antibodies that discriminated the classes.
Figure 17:
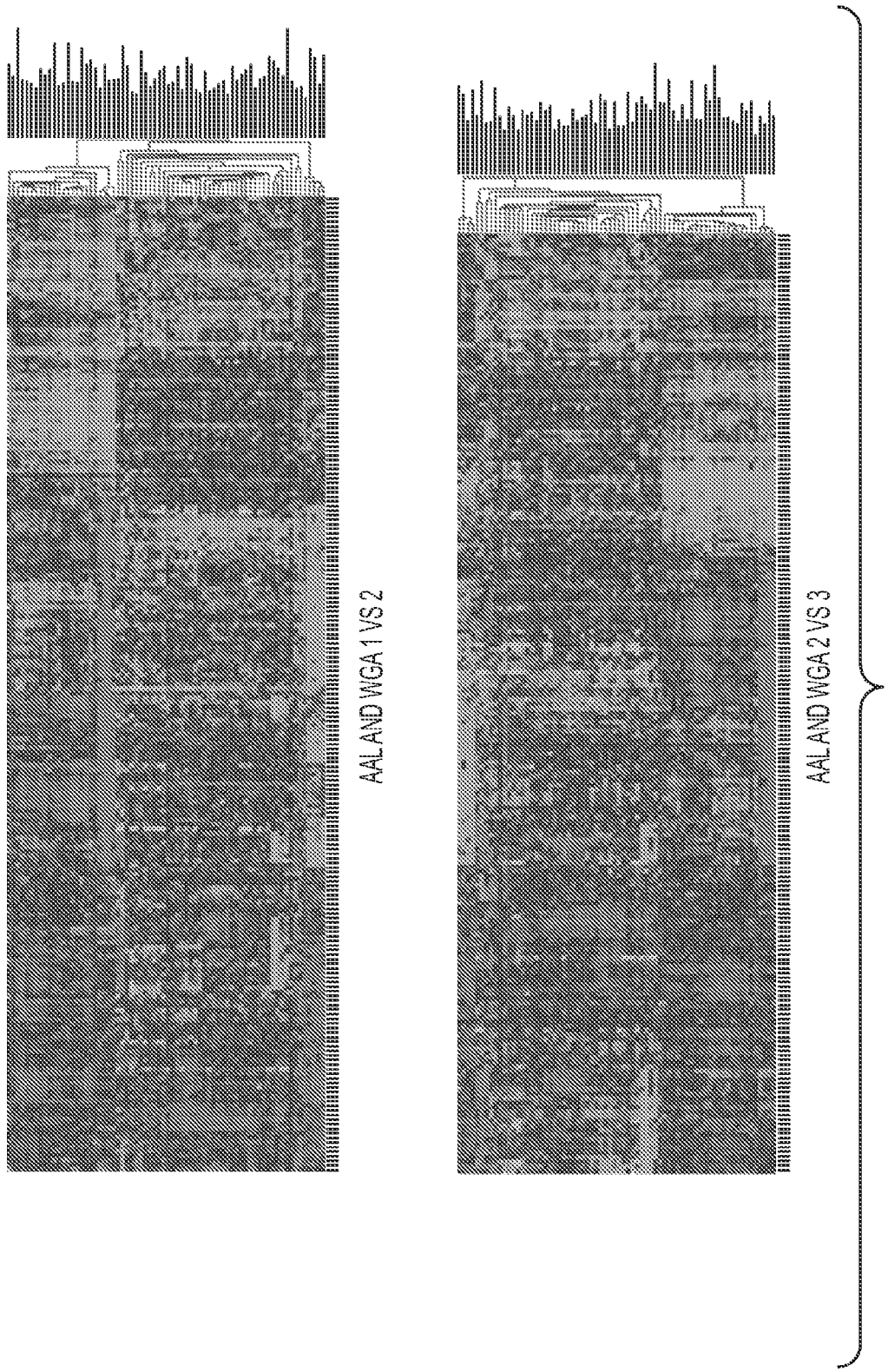
FIG. 17 shows clusters of glycan measurement using all antibodies.

For example, anti-haptoglobin B-subunit was significantly elevated in cancer relative to healthy when detected with AAL (p=3.7 E-5) but statistically equivalent between cancer and healthy when detected with WGA (p=0.99). In contrast, anti-DCP was significantly elevated in cancer when detected with WGA (p=2.9 E-5) but not when detected with AAL (p=0.20). Correlations between the AAL measurements and the WGA measurements for each antibody were very weak, ranging from −0.05 to 0.3. Clusters of the data (FIGS. 16 and 17) also revealed little agreement between the AAL and WGA profiles. However, the clusters also showed that groups of antibodies had similar profiles within each set. That observation may indication that many AAL-specific structures are similarly regulated and many WGA-specific structures are similarly regulated, for the proteins measured here, but the two lectins are measuring glycans with different regulation. As to FIGS. 16 and 17, the samples are ordered on the vertical axis, and the antibodies on the horizontal axis. The left cluster shows the cancer and healthy classes (red and green labels respectively), and the right cluster shows the cancer and benign classes (red and blue labels, respectively). Red squares indicate high binding, and green is low.

An important question in measuring changes in glycans is whether the underlying protein concentration is changing or whether the amount of glycan per protein is changing. The inventor investigated this question using parallel sandwich and lectin-detection assays to look at variation in protein and glycan levels, respectively. Serum samples (23 from cancer and 23 from control patients) were incubated on replicate sets of arrays, and each set of arrays was detected either with a detection antibody to measure protein levels or with a lectin (AAL or WGA) to measure glycan levels (FIG. 15B). The inventor also detected a set of arrays with the glycan-binding antibody anti-CA19-9 (FIG. 15B). The specificities and potential cross-reactivities between detection antibodies for carcinoembryonic antigen (CEA) and MUC1 were checked (FIG. 15B, left panels), and the detection antibodies were pooled to provide multiplexed detection of both proteins. Representative images of the arrays showed that the proteins were present in both cancer and control sera (FIG. 15A, middle panels), but detection with the anti-CA19-9 antibody showed an elevation in cancer (FIG. 15B, right panels). One set of 46 arrays was detected with antibodies against CEA and MUC1 to obtain the variation in protein levels of these two proteins, and other sets of arrays were detected with the lectin AAL, the lectin WGA, or the glycan-binding antibody anti-CA19-9. In FIG. 15B, the distributions of the levels of the control samples (white bars) and the cancer samples (dark bars) are shown, in which the boxes give the upper and lower quartiles of the measurements with respect to the median value (horizontal line in each box), and the lines give the ranges of the measurements, excluding outliers, which are represented by circles. The number of outliers not shown is given in the upper right corner of each plot (FIG. 15B). The asterisks indicates the measurements that were statistically different (p<0.05) between the two classes. The right three panels show the ratios of glycan levels to total protein levels for each of the three glycans measured.

Comparisons of the distributions of protein levels, glycan levels, and the ratio of glycan-to-protein indicated which levels were altered in cancer (FIG. 15B). CEA protein levels were increased in cancer, and the WGA-reactive and CA19-9-reactive glycans on CEA also showed an increase in cancer. MUC1 protein levels did not change between cancer and control, but all three glycans showed elevations in cancer. For both CEA and MUC1, the ratios of CA19-9 levels to total protein levels were increased in cancer relative to control (FIG. 15B, right panels), meaning that the carbohydrate structure targeted by the anti-CA19-9 antibody was present at a higher level, per molecule, on these molecules in the cancer sera. A comparative view of the MUC1 and CEA protein levels and CA19-9 detection levels for each sample also showed the elevation in the CA19-9-reactive structure on those molecules (FIG. 15C).

Figure 15A:
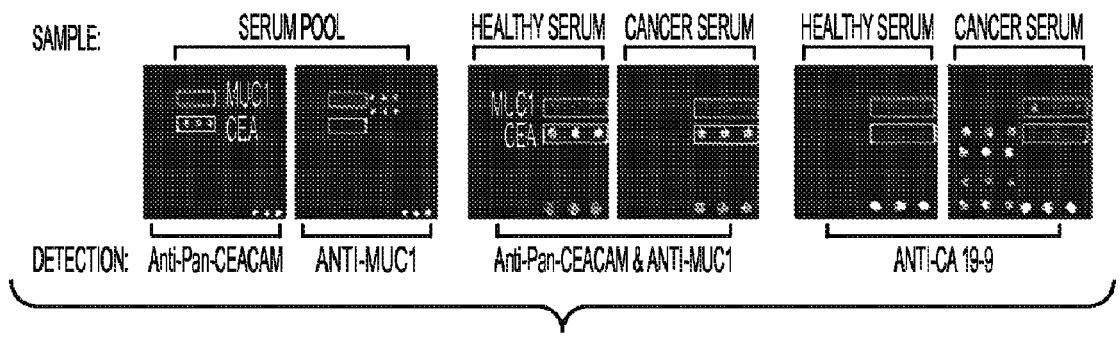
FIGS. 15A-C show comparison of protein and glycan levels using parallel sandwich and glycan-detection assays.
Figure 15B:
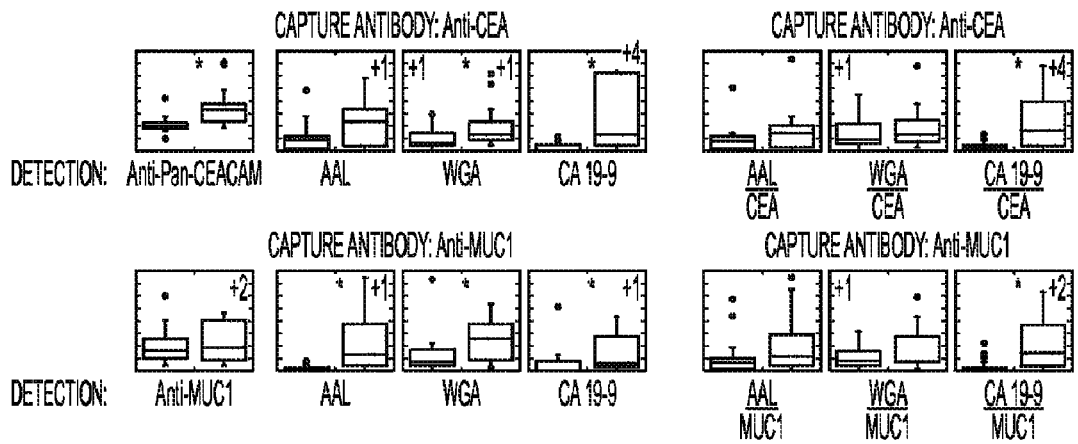
Figure 15C:
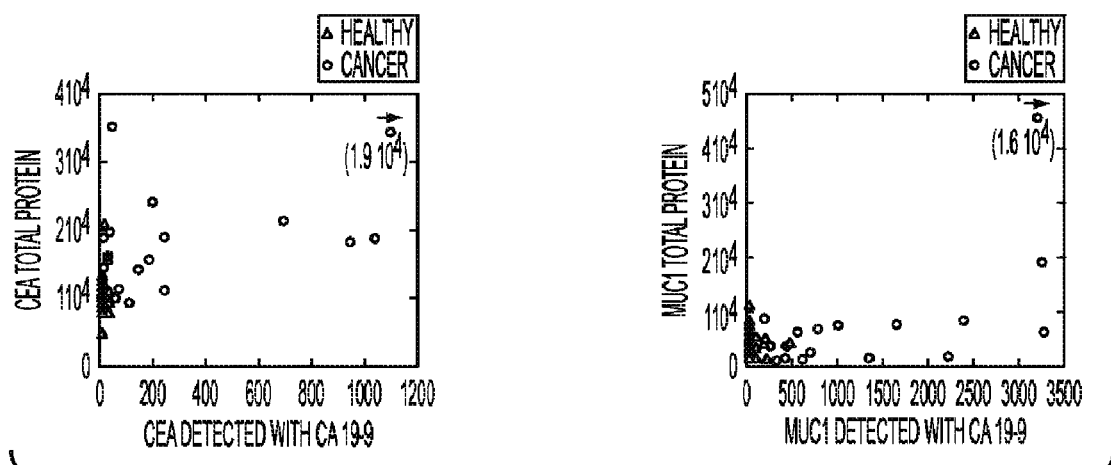

As to FIG. 15A, the spots appearing at the lower right of each array were biotinylated control proteins. The other spots that showed signals were anti-haptoglobin in the array detected with anti-MUC1 (second image from left) and anti-CA19-9, anti-pan CEACAM, and the WGA lectin in the array detected with anti-CA19-9 (rightmost image).

Example 14

Microarray Fabrication and Use (for Examples 11-13)

A piezoelectric non-contact printer (Biochip Arrayer, PerkinElmer Life Sciences) spotted approximately 350 pl of each antibody solution on the surfaces of ultra-thin-nitrocellulose-coated microscope slides (PATH slides, GenTel Biosurfaces). Forty-eight identical arrays were printed on each slide, with each array consisting of 36-48 antibodies and control proteins spotted in triplicate. A wax border was imprinted around each of the arrays to define hydrophobic boundaries, using a custom-built device.

For the experiments not using chemical blocking of the antibodies, the slides were rinsed briefly in PBST0.5, blocked for one hour at room temperature in PBST0.5 containing 1% BSA and 0.3% CHAPS, rinsed twice more with PBST0.5, and dried by centrifugation prior to sample application. For the experiments using chemical blocking, the blocking procedure was performed as follows. The slides were incubated in a coupling buffer (1M sodium acetate, pH 5.5, with 0.1% Tween-20) for 30 minutes, and 50 mM $NaIO_4$ was applied to the slides at 4° C. for 30 minutes in the dark to oxidize the sugar groups. The slides were rinsed in coupling buffer and incubated with 15 mM glycerol in coupling buffer for 5 minutes. One mM 4(4-N-maleimidophenyl)butyric acid hydrazide hydrochloride (MPBH) was incubated on the slides for two hours at room temperature to derivatize the carbonyl groups. The slides were rinsed briefly with 1× phosphate-buffered saline with 0.1% Tween-20 (PBST0.1), incubated with 1 mM Cystein-Glycein dipeptide in PBST0.1 overnight at 4° C., then rinsed thoroughly and dried.

For the experiments using labeled serum proteins, the labeling procedure followed previously-established protocols (Haab, B. B., Dunham, M. J. & Brown, P. O. Protein microarrays for highly parallel detection and quantitation of specific proteins and antibodies in complex solutions. Genome Biology 2, 1-13 (2001); Haab, B. B. & Zhou, H. Multiplexed protein analysis using spotted antibody microarrays. Methods Mol Biol 264, 33-45 (2004)). An aliquot of each sample was reacted with NHS-digoxigenin (Molecular Probes), the unincorporated tag was removed by gel filtration (Bio-spin P6 column, Bio-Rad), and the labeled sample was brought to a final 1:20 dilution in sample buffer (PTBST0.1 containing 100 µg/ml mouse, goat, and sheep IgG, 100 µg/ml chicken IgY, 200 µg/ml rabbit IgG, 0.08% Tween-20, 0.08% Brij-35 and protease inhibitors (Roche Biosciences, one tablet per 5 ml buffer). For experiments using unlabeled sera, an aliquot of each serum sample was brought to a final 1:20 dilution in the above sample buffer. Each serum sample was incubated on a microarray with gentle rocking at room temperature for one hour, and the slides were rinsed once and washed three times for three minutes each in PBST0.1. Fluorescence emission was detected at 570 nm and 670 nm using a microarray scanner (ScanArray Express HT, PerkinElmer Life Sciences). All arrays within an experiment set were scanned in one sitting at a single laser power and detector gain setting. The software program GenePix Pro 5.0 (Axon Instruments) was used to quantify the image data. Median local backgrounds were subtracted from the median intensity of each spot, and data from replicate spots were averaged (geometric mean). The data were not normalized.

Example 15

Serum Samples (or Examples 11-13)

Serum samples were assembled from two sites. At Evanston Northwestern Healthcare (ENH, Evanston, Ill.), serum samples were collected from patients with pancreatic adenocarcinoma (stage I to stage IV) or benign gastro-intestinal diseases (such as ampullary adenoma, pancreatitis, cystadenoma, or pseudocyst). Control samples also were collected at ENH from high-risk individuals from pancreatic cancer prone families undergoing surveillance with Endoscopic Ultrasound (EUS) or Endoscopic Retrograde Cholangiopancreatography (ERCP). The control subjects had no pancreatic lesions, and serum samples were collected using the same procedure as for the other patients at ENH. At the Multidisciplinary Pancreatic Tumor Clinic at the University of Michigan (UM) Comprehensive Cancer Center, serum samples were obtained from patients with a confirmed diagnosis of pancreatic adenocarcinoma. Sera also were obtained from patients with chronic pancreatitis who were seen in the Gastroenterology Clinic at University of Michigan Medical Center and from control healthy individuals collected at University of Michigan under the auspices of the Early Detection Research Network (EDRN). The samples were stored at each site at −80° C. and were sent frozen on dry ice to the VARI, where they were stored at −80° C. Each aliquot had been thawed no more than two times prior to use. All samples were coded to protect patient anonymity and were collected under protocols approved by local Institutional Review Boards for human subjects research.

What is claimed is:

1. A microarray slide comprising a solid support and at least two different antibodies having carbohydrate groups; which different antibodies bind specifically to target proteins, are spotted at particular addresses on the solid support, and are randomly oriented with respect to the solid support; and which carbohydrate groups of the different antibodies are oxidized and derivatized by a hydrazide-maleimide bifunctional crosslinking reagent so that recognition of the carbohydrate groups by a glycan binding protein is reduced without eliminating the binding activities of the different antibodies to their specific target proteins.

2. The microarray slide of claim 1 wherein the carbohydrate groups of the different antibodies are oxidized by $NaIO_4$.

3. The microarray slide of claim 1 wherein a cysteine-glycine dipeptide is attached to the crosslinking reagent.

4. A kit comprising the microarray slide of claim 1 and a glycan binding protein.

5. The kit of claim 4 wherein the glycan binding protein is lectin.

6. The kit of claim 4 wherein the glycan binding protein is tagged with a tag.

7. The kit of claim 6 wherein the tag is radioactive, fluorescent, fluorogenic, chromogenic, or is biotin.

8. A method of measuring the glycan level of a protein comprising detecting the glycan level of a protein in a sample using the microarray slide of claim 1.

9. A method of measuring the glycan level of a protein comprising detecting the glycan level of a protein in a sample using the kit of claim 4.

* * * * *